United States Patent [19]

Stache et al.

[11] 4,242,334
[45] Dec. 30, 1980

[54] CORTICOID 17-(ALKYL CARBONATES) AND PROCESSES FOR THEIR PREPARATION

[75] Inventors: Ulrich Stache, Hofheim am Taunus; Werner Fritsch, Bad Soden am Taunus; Hans G. Alpermann, Königstein all of Fed. Rep. of Germany

[73] Assignee: Hoechst Aktiengesellschaft, Frankfurt am Main, Fed. Rep. of Germany

[21] Appl. No.: 930,194

[22] Filed: Aug. 2, 1978

[30] Foreign Application Priority Data

Aug. 4, 1977 [DE] Fed. Rep. of Germany ....... 2735110

[51] Int. Cl.$^3$ .......................... A61K 31/56; C07J 7/00
[52] U.S. Cl. .......................... 424/243; 260/239.55 D; 260/239.55 R; 260/397.45; 260/239.5; 260/397.47
[58] Field of Search ................. 260/239.55 D, 397.45; 424/243

[56] References Cited

U.S. PATENT DOCUMENTS

| | | | |
|---|---|---|---|
| 3,152,154 | 10/1964 | Ercoli et al. ..................... | 260/397.45 |
| 3,422,193 | 1/1969 | Shapiro et al. ................. | 260/239.55 D |
| 3,558,675 | 1/1971 | Sarett et al. ...................... | 260/397.47 |
| 3,621,014 | 11/1971 | Stache et al. ................ | 260/239.55 D |
| 3,891,631 | 6/1975 | Phillipps et al. ................ | 260/397.45 |

OTHER PUBLICATIONS

Chem. Abstracts, vol. 72 (1970), Par. 12,998f.

*Primary Examiner*—Elbert L. Roberts
*Attorney, Agent, or Firm*—Curtis, Morris & Safford

[57] ABSTRACT

What is disclosed is corticoid 17-(alkyl carbonates) of the formula

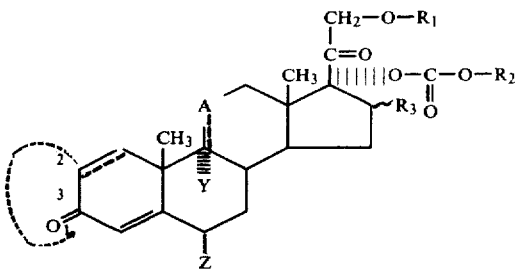

as defined in the specification, which compounds can be used in veterinary therapy and human therapy, in the form of suspensions, ointments, creams, sprays and the like, for the treatment of inflammatory dermatoses of very diverse cause.

22 Claims, No Drawings

CORTICOID 17-(ALKYL CARBONATES) AND PROCESSES FOR THEIR PREPARATION

The invention relates to novel steroid 17-(alkyl carbonates) of the formula I

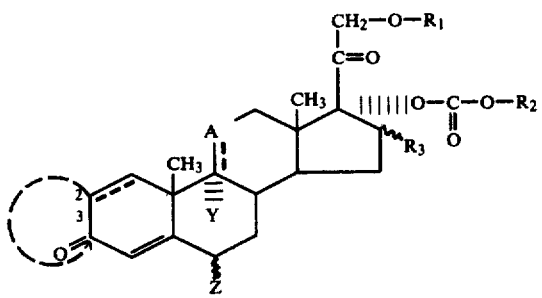

in which A denotes the groupings

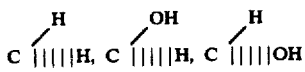

or C=O or, if a double bond is present in the 9,11-position, C—H, Y denotes hydrogen, fluorine or chlorine, Z denotes hydrogen, chlorine, fluorine or a methyl group, $R^1$ denotes hydrogen, an acyl radical of the formula II

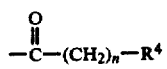

in which $R^4$ denotes hydrogen or a straight-chain or branched aliphatic hydrocarbon radical having 1–10 C atoms or a cycloaliphatic hydrocarbon radical having 3–8 C atoms and n represents the numbers 0–4, or, if n≠0, $R^4$ represents halogen or a radical of the formula

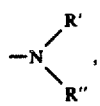

in which R' and R" are identical or different and denote hydrogen or alkyl radicals having 1–4 C atoms, or R' and R" together with the nitrogen atom represent a saturated heterocyclic structure having 5–7 members, or $R^1$ denotes a carbonyloxyalkyl radical of the formula III

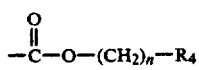

in which n and $R^4$ have the indicated meaning and $R^4 \neq H$ when n is 0 and can denote only halogen when n is 2–4, or an aliphatic or aromatic sulfonic acid ester of the formula IV

in which $R_5$ denotes $C_1$–$C_4$-alkyl, phenyl, methylphenyl, ethylphenyl, fluorophenyl, bromophenyl or chlorophenyl, $R_2$ denotes a branched or unbranched alkyl radical having 1 to 8 C atoms and $R_3$ denotes hydrogen, methyl in the α- or β-position, fluorine or a methyl group which is optionally substituted by one or two fluorine atoms, and in which additional double bonds can be present in the 1,2- and/or 2,3- and/or 6,7- and/or 9,11-position, and in which

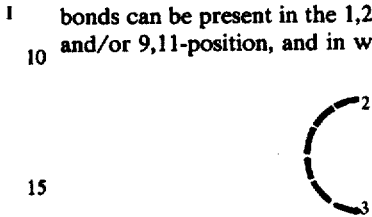

denotes a pyrazole ring which is fused to the 2- and 3-positions of the 3-deoxo-steroid skeleton and can optionally carry a $C_1$–$C_4$-alkyl group or an optionally halogen-substituted phenyl group on one of the two N atoms.

The invention also relates to a process for the preparation of compounds of the formula I, which comprises hydrolyzing corticosteroid 17,21-(dialkyl orthocarbonates) of the formula

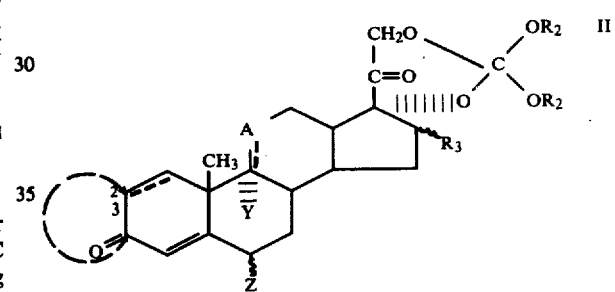

in which A, Y, Z,

$R_2$ and $R_3$ have the meaning indicated under formula I and in which additional double bonds can be present in the 1,2- and/or 2,3- and/or 6,7- and/or 9,11-position, to steroid 17-(monoalkyl carbonates) of the formula III

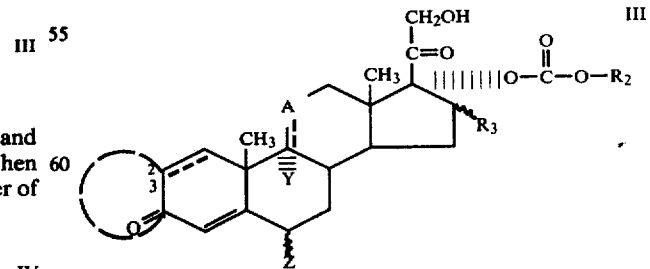

and then reacting these, in the 21-position, with carboxylic acid halides or carboxylic acid anhydrides containing the radical

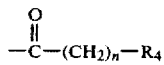

or with halogenoformates containing the radical

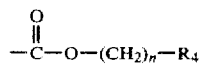

or with aliphatic or aromatic sulfonic acid halides containing the radical

in which formulae $R_4$ and $R_5$ have the abovementioned meanings, to give steroid 17-(alkyl carbonates) of the formula I and, if $R_1 \neq H$, optionally oxidizing a OH group in the 11-position to a keto group by conventional methods.

Amongst the meanings indicated for the radicals $R_2$, $R_4$ and $R_5$, the following are preferred:

For $R_2$: alkyl having 1-5 C atoms,

For $R_4$: hydrogen, alkyl having 1-10 C atoms, cycloalkyl having 3-6 C atoms or, if $n \neq 0$, fluorine, chlorine, bromine or a piperidine radical, and For $R_5$: methyl, ethyl, propyl, phenyl and the other substituted phenyl radicals mentioned for $R_5$, the substituents in each case being in the p-position.

Especially preferred are compounds of formula I in which Y and Z do not represent halogen.

The steroid 17α,21-(dialkyl orthocarbonates) of the formula II required as starting substances are known and can be prepared, for example, according to German Pat. No. 1,668,079. Starting materials which can be used are in particular the 17α,21-(dialkyl orthocarbonates) of the following 17α,21-dihydroxy-steroids and -corticoids: cortisone, hydrocortisone, Reichstein's substance S, prednisone, prednisolone, 6α-methylprednisolone, 16α- or 16β-methylprednisolone, 9α-fluoro- or 9α-chloro-prednisolone, 16-methyleneprednisolone, 6α,9α-difluoroprednisolone, 6α-methyl-9α-fluoro-prednisolone, 6α-fluoro-prednisolone, 9α-fluoro-16α-methyl-prednisolone, 9α-fluoro-prednisolone, 9α-fluoro-16α-methyl-prednisolone, 9α-fluoro-prednisolone, 9α-fluoro-16-methyl-prednisolone, 6α-fluoro-16α-methyl-prednisolone, 6α-fluoro-16β-methyl-prednisolone, 6α-fluoro-16-methylene-prednisolone, 6α,9α-difluoro-16α-methyl-prednisolone, 6α,9α-difluoro-16β-methyl-prednisolone, 6α,9α-difluoro-16-methylene-prednisolone, 9α-fluoro-6α,16α-dimethylprednisolone, 9α,16α-difluoro-prednisolone, 17α,21-dihydroxy-$\Delta^{4(5),9(11)}$-pregnadiene-3,20-dione, 17α,21-dihydroxy-9β,11β-oxido-$\Delta^4$-pregnene-3,20-dione, 17α,21-dihydroxy-9α,11β-dichloro-$\Delta^{1,4}$-pregnadiene-3,20-dione, 17α,21-dihydroxy-$\Delta^{4(5),6(7)}$-pregnadiene-3,20-dione, deoxycorticosterone, corticosterone, 16α-methyl-corticosterone, 9α-fluoro-16α-methyl-corticosterone, 6α,9α-difluoro-16α-methylcorticosterone, 6α-fluoro-16α-methyl-corticosterone, 6,16α-dimethyl-4,6-pregnadiene-11β,17α,21-triol-[3,2-c]-2'-phenylpyrazole and -2'-p-fluorophenylpyrazole and their analogs substituted by fluorine in the 9α-position. Furthermore, those of the said corticoids which contain, in place of a 6α-fluoro and/or 9α-fluoro and/or 11β-hydroxy group, a chlorine atom oriented in the corresponding configuration can be used.

In the first reaction stage of the process, that is to say the proton-catalyzed hydrolysis of the steroid 17α,21-(dialkyl orthocarbonate) to a corresponding steroid 17α-(monoalkyl carbonate)-21-hydroxy compound, preferably a carboxylic acid, such as, for example, formic acid, acetic acid, propionic acid, butyric acid, valeric acid, oxalic acid, maleic acid, fumaric acid, succinic acid or adipic acid, or an organic sulfonic acid, such as, for example, p-toluenesulfonic acid, benzenesulfonic acid or p- or o- or m-chloro- or -bromo-benzenesulfonic acid, or an inorganic acid, such as, for example, hydrochloric acid, sulfuric acid, carbonic acid or nitric acid, is used. The course of the reaction to give the desired steroid 17α-(monoalkyl carbonate)-21-hydroxy compounds is the more specific the weaker the acid, that is to say the closer the pH vaue approaches a value of 7. This is the more surprising since both of the alkoxy ligands linked to the carbon atom of the orthocarbonic acid grouping are equivalent, that is to say are not unequivalent as, for example, in the case of the formally similarly structured 17α,21-steroid-carboxylic acid orthoesters, and are thus not able to develop or induce the regiospecificity associated with the latter ligands with respect to a preferred splitting of the orthoester. In order to adjust the pH to the desired value with the said acids, it is frequently appropriate to add water and/or inert organic solvents, such as, for example, alcohols, linear or cyclic ethers, esters, dialkylformamides, dialkylsulfoxides or hexamethylphosphoric acid triamide, for dilution and, in addition to the dilution effect, a catalytic or regioselective effect in the direction of the desired course of reaction is frequently produced.

The course of reaction in the desired direction is appropriately followed by thin layer chromatography. It is advantageous to discontinue the reaction, by neutralizing, for example with dilute ammonia, or adjusting the pH to values above 7, when the thin layer diagram indicates, after optimum formation of the desired steroid 17α-(monoalkyl carbonate)-21-hydroxy compounds, that these are being isomerized to the steroid 17α-hydroxy-21-(monoalkyl carbonate) compounds which are not desired.

Preferably, the corticoid 17,21-(orthoalkyl carbonate) is dissolved in a carboxylic acid, such as, for example, in acetic acid or propionic acid, preferably about 0.1 to 1% of water is added and the mixture is allowed to react for up to about 8 hours at a temperature of 0° up to the boiling point of the acid or solvent used. When optimum formation of the desired product has been determined in the thin layer chromatography diagram, the reaction mixture is stirred into water or sodium chloride solution, the resulting mixture is neutralized, for example with aqueous ammonia or another weak base, and either the precipitate is filtered off or the mixture is extracted in a conventional manner with organic solvents, the extract is evaporated and the resulting products are recrystallized and chromatographed, if starting material is still detectable, or 21-(alkyl carbonate) is already detectable, in the thin layer chromatography diagram, if necessary on silica gel or aluminum oxide.

Depending on whether a 21-(alkyl carbonate), a 21-(carboxylic acid ester) or a 21-(alkyl- or aryl-sulfonic acid ester) of the basic corticoid 17-(alkyl carbonates) is to be prepared, the 21-hydroxy group can be reacted with the acylating agents customary for this purpose:

(a) In order to prepare 21-(alkyl carbonates), alkyl chloroformates of the formula

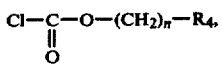

in which $R_4$ has the meaning indicated under formula I, are preferably used. Preferably, methyl chloroformate, ethyl chloroformate, propyl chloroformate or butyl chloroformate is used.

(b) In order to prepare 21-(carboxylic acid esters), either carboxylic acid halides of the formula

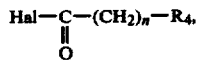

in which Hal represents Cl, Br or I and $R_4$ has the meaning indicated under formula I, or carboxylic acid anhydrides of the formula $(OC-(CH_2)_n-R_4)_2O$, in which $R_4$ has the meaning indicated under formula I, are preferably used. For example, acetyl chloride or acetic anhydride, propionyl chloride or propionic anhydride, butyryl chloride or butyric anhydride, valeryl chloride or valeric anhydride, cyclopropanecarboxylic acid chloride, cyclopentylpropionyl chloride or oenanthyl chloride can be used.

(c) In order to prepare 21-(sulfonic acid esters), sulfonic acid halides of the formula $Cl-SO_2-R_5$, in which $R_5$ has the meaning indicated under formula I, can be used. Preferably, methanesulfonyl chloride and o-, m- or p-toluenesulfonyl chloride are employed.

For the second process stage, the steroid component is dissolved in an inert solvent, such as, for example, in an ether, such as dioxane, tetrahydrofurane or diglyme, or an optionally halogenated hydrocarbon, such as benzene, toluene, cyclohexane, methylene chloride or chloroform, or in a mixture of these solvents. In order to remove the hydrogen halide acid formed during the reaction, 1-1,000 mole equivalents of a tertiary base, such as, for example, pyridine, quinoline, triethylamine or dimethylaniline, are added. However, an inorganic base, such as sodium bicarbonate or calcium carbonate, can also be used to remove the acid. Subsequently, 1-200 mole equivalents, preferably 1-3 mole equivalents, of one of the abovementioned acylating agents, optionally dissolved in one of the abovementioned solvents, is added dropwise at a temperature between $-40°$ C. and the boiling point of the solvent used, preferably between $0°$ C. and $25°$ C. The reaction mixture is then left to stand for one to 120 hours at a temperature between $-40°$ C. and the boiling point of the solvent, preferably between $0°$ C. and $25°$ C.

When carboxylic acid anhydrides are used as the acylating agents, it is frequently advantageous to carry out the reaction without the addition of solvents. As a rule it suffices merely to add the organic base, preferably pyridine, to the acid anhydride used in excess.

For working up, the reaction mixture is poured into water, to which sodium bicarbonate has optionally been added, whereupon the reaction products precipitate, generally in crystalline form, frequently only after prolonged standing. Reaction products which have remained oily are concentrated by extraction by shaking with a suitable extracting agent and evaporating the extract. If necessary, the reaction product can be separated or purified by recrystallization or by chromatography. Frequently, intensive digestion in an organic solvent which dissolves the reaction product as little as possible or does not dissolve it at all, such as diethyl ether or cyclohexane or a mixture of these components, also suffices for further purification of the reaction products.

A hydroxyl group in the 11-position can optionally be oxidized to a keto group by conventional methods. Preferably, this oxidation is carried out with chromium trioxide in an acid medium and in an inert organic solvent.

The products of the process possess valuable pharmacological properties. In particular they have a very powerful local and topical antiphlogistic action and with some of them the ratio of the local to the systemic anti-inflammatory action is advantageous as can be deduced from pharmacological standard tests.

The products can be used in veterinary therapy and human therapy, in the form of suspensions, ointments, creams, sprays and the like, for the treatment of inflammatory dermatoses of very diverse cause. For topical application, they can be administered in the form of crystal suspensions—for example in the case of intraarticular injection. It is to be emphasized that it is particular advantageous for the local and topical therapy form that the products, because of their advantageous ratio of the local to the systemic antiphlogistic action, are able to give rise to virtually only slight systemic side effects even in the case of high dosage and long term therapy. In addition, the products employed have a significantly better stability to acid than do the cyclic corticoid 17,21-orthocarbonates on which they are based. This fact is of decisive importance for a reliable use, in accordance with therapy, of the products according to the invention.

For external treatment ointments, creams, suspensions and the like containing 0.01 to 2% by weight of active ingredient are used. In the case of topical administration in the form of local (non systemic) injections doses of 0.1 to 100 mg are used.

The following general remarks should be made in respect of the Examples given below.

The melting points were determined in a Tottoli apparatus (Messrs. Büchi) and are not corrected.

The IR spectra (in KBr) were recorded using a Perkin-Elmer 521 grating spectrophotometer. In each case only the characteristic bands are given. The UV spectra (in methanol) were recorded using a Beckman DK 1 A spectrophotometer. The investigations by mass spectroscopy (MS) were carried out using the MS 9 apparatus (Messrs. AEI).

Ready-to-use silica gel $F_{254}$ plates (Messrs. Merck) were used for thin layer chromatography (TLC).

Unless otherwise stated, the solvent used was methylene chloride: methanol = 19:1. In each case, developing was carried out once. The spots were rendered visible by spraying with 10% strength methanolic sulfuric acid and by heating to $100°$ C. The $R_f$ values are always to be understood as only relative values. Silica gel 60, particle size 0.063–0.2 mm (Messrs. Merck), was used for column chromatography.

EXAMPLE 1

(a) A solution of 3 g of dexamethasone 17,21-(diethyl orthocarbonate) in 120 ml of glacial acetic acid and 0.6 ml of water is left to stand for 5 hours at $22°$ C. Monitoring by TLC showed that an optimum amount of the desired dexamethasone 17-(ethyl carbonate) was present after this time. The reaction mixture is poured into 1.5 l of water, the pH of which had been brought to 5 with ammonia solution, and a crystalline precipitate separates out. After filtering off, washing with water and drying, 1.8 g of dexamethasone 17-(ethyl carbonate) with a melting point of 154° (Tottoli) are obtained after digesting. The residual aqueous filtrate is extracted with methylene chloride. After distilling off the solvent, a foamy residue remains and this is made to crystallize from diisopropyl ether and gives a further 1.2 g of dexamethasone 17-(ethyl carbonate) with a melting point of 152° C. The two preparations of 1.8 and 1.2 g are combined and recrystallized from ethanol.

Melting point 156° C. (Tottoli)

Characteristic IR bands: 3,440, 2,940, 2,880, 1,735, 1,720, 1,660, 1,610 and 1,265 cm$^{-1}$ Mass spectrum: molecular weight peak at M$^{\oplus}$: 464

TLC: R$_f$=0.43

(CH$_2$Cl$_2$: CH$_3$OH = 19:1)

(b) A solution of 4 g of dexamethasone 17,21-(dimethyl orthocarbonate) in 250 ml of glacial acetic acid and 1 ml of water is left to stand for 15 minutes at 20° C. and then stirred into 2.5 l of half-saturated sodium chloride solution. After analogous working-up and further treatment as indicated under Example (1) (a), 3.2 g of dexamethasone 17-(methyl carbonate) are obtained.

Mass spectrum: M$^+$: 450

TLC: R$_f$=0.42

(c) A solution of 4.5 g of dexamethasone 17,21-(di-(n-propyl) orthocarbonate) in 280 ml of glacial acetic acid and 1.2 ml of water is left to stand for 5 hours at 20° C. and poured into 4 l of half-saturated sodium chloride solution. The supernatant liquor is decanted from the oily precipitate and the oil is taken up in methylene chloride and washed with water. After distilling off the solvent, 3.3 g of dexamethasone 17-(n-propyl carbonate) are obtained in the form of an amorphous foam which is employed in the subsequent reactions without further treatment.

Characteristic IR bands: 3,440, 1,730, 1,655, 1,610 and 1,240 cm$^{-1}$

Mass spectrum: M$^+$=476

TLC: R$_f$=0.42

(d) 4.5 g of dexamethasone 17,21-(di-(n-butyl) orthocarbonate) are reacted, and the product is worked up, in the same way as described in Example (1) (c). After digesting with diisopropyl ether, 2.9 g of dexamethasone 17-(n-butyl carbonate) with a melting point of 92° C. are obtained.

IR: 3,430, 1,730, 1,655, 1,605 and 1,270 cm$^{-1}$ (e) 4.5 g of dexamethasone 17,21-(di-(n-pentyl) orthocarbonate) (melting point 106° C.), prepared from dexamethasone and tetra-n-pentyl orthocarbonate according to German Pat. No. 1,668,079, are reacted, and the product is worked up, in the same way as described in Example (1) (c). 3.4 g of amorphous dexamethasone 17-(n-pentyl carbonate) are obtained.

IR: 3,440, 1,735, 1,660, 1,610 and 1,275 cm$^{-1}$

EXAMPLE 2

(a) A solution of 1.1 g of ethyl chloroformate in 9 ml of dioxane is added dropwise at about 0° C. to a solution of 1.4 g of dexamethasone 17-(ethyl carbonate) in 3 ml of absolute dioxane and 4.5 ml of pyridine. After stirring for 5 hours at 0° C., the mixture is poured into about 300 ml of half-saturated aqueous sodium chloride solution, the resulting mixture is extracted with methylene chloride, the organic phase is washed with water, the solvent is evaporated in vacuo and 1.4 g of dexamethasone 17,21-bis-[ethyl carbonate] with a melting point of 202°-204° C. are obtained.

In TLC, the product still shows weak secondary spots at R$_f$=0.47 and 0.33, in addition to the strong main spot at R$_f$=0.57. In order to prepare the product in a very pure form, the reaction product is therefore fractionated by chromatography on silica gel (3×10 cm column) using acid-free methylene chloride as the absorbent and eluting agent. The fractions in which exclusively the desired process product is identified on the basis of the TLC diagram (R$_f$=0.57) are combined and crystallized from ethanol/ether.

1.2 g of dexamethasone 17,21-bis-(ethyl carbonate) with a melting point of 210° C. are obtained.

TLC: R$_f$=0.57 (no secondary spots!)

IR: 3,420, 1,735, 1,660, 1,610 and 1,260 cm$^{-1}$ (b) 1.4 g of dexamethasone 17-(ethyl carbonate) are reacted with 1.1 g of methyl chloroformate instead of ethyl chloroformate, and the product is worked up, in the same way as described under Example 2(a).

Dexamethasone 17-(ethyl carbonate)-21-(methyl carbonate) is obtained.

IR: 3,420, 1,740, 1,665, 1,615 and 1,260 cm$^{-1}$ (c) 1.4 g of dexamethasone 17-(ethyl carbonate) are reacted with 1.2 g of propyl chloroformate instead of ethyl chloroformate, and the product is worked up, in the same way as described under Example 2(b).

Dexamethasone 17-(ethyl carbonate)-21-(n-propyl carbonate) is obtained.

IR: 3,420, 1,735, 1,660, 1,615 and 1,265 cm$^{-1}$ (d) 1.4 g of dexamethasone 17-(ethyl carbonate) are reacted with 1.3 g of n-butyl chloroformate instead of ethyl chloroformate, and the product is worked up, in the same way as described under Example 2(b).

Dexamethasone 17-(ethyl carbonate)-21-(n-butyl carbonate) is obtained.

IR: 3,420, 1,735, 1,660, 1,610 and 1,265 cm$^{-1}$ (e) 1.4 g of dexamethasone 17-(ethyl carbonate) are reacted with 1.2 g of iso-propyl chloroformate instead of ethyl chloroformate, and the product is worked up, in the same way as described under Example 2(b).

Dexamethasone 17-(ethyl carbonate)-21-(isopropyl carbonate) is obtained.

IR: 3,420, 1,735, 1,665, 1,615 and 1,265 cm$^{-1}$ (f) 5 ml of methanesulfonyl chloride are added dropwise at 0° C. to a solution of 3 g of dexamethasone 17-(ethyl carbonate) in 35 ml of absolute acetone and 12 ml of absolute pyridine. After stirring for 20 hours at 0° to 22° C. (the temperature is allowed to rise gradually), the mixture is poured into water and the resulting mixture is extracted with methylene chloride, the organic phase is washed and the extraction agent is concentrated in vacuo. The residue is chromatographed on silica gel (4×14 cm column) using methylene chloride as the eluting agent. The fractions which are pure according to TLC and have R$_f$=0.62 are combined and crystallized from ethanol/ether.

2.6 g of dexamethasone 17-(ethyl carbonate)-21-methanesulfonate with a melting point of 193° C. are obtained.

Mass spectrum: M$^+$=542

IR: 3,430, 1,730, 1,655, 1,610, 1,600, 1,350, 1,265, 1,170 and 1,030 cm$^{-1}$ (g) 0.3 ml of cyclopropanecarboxylic acid chloride is added dropwise to a solution of 1 g of dexamethasone 17-(ethyl carbonate) in 12 ml of absolute pyridine. After stirring for 24 hours at 20° C., the mixture is poured into water/NaCl solution and the precipitate is filtered off. Yield 1 g. After chromatography on silica gel (2×10 cm column) with methylene chloride, optionally with the addition of 2% of methanol, the fractions having only one spot at $R_f=0.6$ are combined and crystallized from ethanol/ether.

730 mg of dexamethasone 17-(ethyl carbonate)-21-cyclopropanecarboxylate with a melting point of 219° C. are obtained.

IR: 3,440, 1,730, 1,660, 1,610 and 1,260 cm$^{-1}$
MS spectrum: M$^+$ = 532

(h) 0.26 ml of propionyl chloride is added dropwise at 0° C. to a solution of 1 g of dexamethasone 17-(ethyl carbonate) in 12 ml of pyridine and the mixture is then stirred for 3 hours at 20° C. It is poured into water and neutralized with dilute hydrochloric acid, the oil which has precipitated is separated off and taken up in methylene chloride, the resulting solution is washed with water, concentrated in vacuo and chromatographed as indicated in Example 2 g and the residue is recrystallized from ether.

817 mg of dexamethasone 17-(ethyl carbonate)-21-n-propionate with a melting point of 220°-222° C. are obtained;

TLC: $R_f=0.6$
IR: 3,450, 1,730, 1,660, 1,610, 1,600 and 1,260 cm$^{-1}$
MS spectrum: M$^+$ = 520

(i) 1 g of dexamethasone 17-(ethyl carbonate) are reacted with acetyl chloride instead of propionyl chloride, and the product is worked up, in the same way as described under Example 2(h). Dexamethasone 17-(ethyl carbonate)-21-acetate with a melting point of 236°-240° C. is obtained.

IR: 3,460, 1,740, 1,660, 1,610 and 1,265 cm$^{-1}$

The same product is obtained when 4 ml of acetic anhydride are chosen instead of acetyl chloride and the reaction mixture is worked up in an analogous manner after standing for 16 hours at 20° C.

(j) 1 g of dexamethasone 17-(ethyl carbonate) is reacted with 0.3 ml of butyryl chloride instead of propionyl chloride, and the product is worked up, in the same way as described under Example 2(h).

Dexamethasone 17-(ethyl carbonate)-21-butyrate with a melting point of 202°-205° C. is obtained.

(k) 1 g of dexamethasone 17-(ethyl carbonate) is reacted with 0.4 ml of valeryl chloride instead of propionyl chloride, and the product is worked up, in the same way as described under Example 2(h).

Dexamethasone 17-(ethyl carbonate)-21-valerate is obtained.

IR: 3,460, 1,735, 1,660, 1,610 and 1,260 cm$^{-1}$ (l) 1 g of dexamethasone 17-(ethyl carbonate) is reacted with 1.28 g of cyclopentylpropionyl chloride, dissolved in 3 ml of absolute dioxane, instead of cyclopropanecarboxylic acid chloride, and the product is worked up, in the same way as described under Example 2(g).

645 mg of dexamethasone 17-(ethyl carbonate)-21-cyclopentyl-propionate with a melting point of 202° C. are obtained.

IR: 3,440, 1,735, 1,660, 1,600 and 1,265 cm$^{-1}$
MS spectrum: M$^+$ = 588

EXAMPLE 3

(a) A solution of 0.32 ml of methyl chloroformate in 2 ml of absolute dioxane is added dropwise at 0° C. to a solution of 1 g of dexamethasone 17-(methyl carbonate) in 6 ml of absolute dioxane and 4 ml of absolute pyridine, while stirring. After stirring for 5 hours at room temperature, the mixture is poured into 300 ml of half-saturated aqueous sodium chloride solution and the crystalline product which has precipitated out is filtered off, washed with water and dried. 1.2 g of crude dexamethasone 17,21-bis-[methyl carbonate] are obtained and this is chromatographed on silica gel (3×13 cm column) with methylene chloride. The fractions which show only one point at $R_f= \sim 0.55$ in TLC are combined and crystallized from alcohol/ether. Dexamethasone 17,21-bis-(methyl carbonate) with a melting point of 250° C. is obtained.

TLC: $R_f=0.55$
IR: 3,460, 1,740, 1,655, 1,610, 1,440 and 1,275 cm$^{-1}$
MS spectrum: M$^+$ = 508

(b) A solution of 550 mg of ethyl chloroformate in 2.7 ml of dioxane is added dropwise to a solution of 700 mg of dexamethasone 17-(methyl carbonate), which according to TLC is a single compound, in 4.5 ml of dioxane and 2.8 ml of pyridine, at 0° and while stirring. After stirring for a further 16 hours at 0° C., the mixture is stirred into aqueous sodium chloride solution and the crystalline product which has precipitated out is filtered off, dried (710 mg) and recrystallized from acetone/ether. 630 mg of dexamethasone 17-(methyl carbonate)-21-(ethyl carbonate) with a melting point of 249° C., which according to TLC is a single compound ($R_f=0.53$), are obtained.

IR: 3,460, 1,740, 1,655, 1,610, 1,440 and 1,265 cm$^{-1}$
Mass spectrum: M$^+$ = 522

(c) 700 mg of dexamethasone 17-(methyl carbonate) are reacted (1) with 600 mg of n-propyl chloroformate, (2) with 650 mg of n-butyl chloroformate, (3) with 600 mg of iso-propyl chloroformate and (4) with 650 mg of iso-butyl chloroformate, instead of with ethyl chloroformate, and the product is worked up, in the same way as described in Example 3 (b).

The corresponding (1) dexamethasone 17-(methyl carbonate)-21-(n-propyl carbonate), (2) dexamethasone 17-(methyl carbonate)-21-(n-butyl carbonate), (3) dexamethasone 17-(methyl carbonate)-21-(iso-propyl carbonate) and (4) dexamethasone 17-(methyl carbonate)-21-(iso-butyl carbonate) is thus obtained in each case.

(d) 3 g of dexamethasone 17-(methyl carbonate) are reacted with methanesulfonyl chloride, and the product is worked up, in the same way as described in Example 2 (f).

2.4 g of dexamethasone 17-(methyl carbonate)-21-methanesulfonate with a melting point of 210°-214° C. (decomposition) are obtained.

MS spectrum: M$^+$ = 528

(e) 0.5 ml of cyclopropanecarboxylic acid chloride, dissolved in 1 ml of dioxane, is added dropwise to a solution of 600 mg of dexamethasone 17-(methyl carbonate) in 3 ml of pyridine and 5 ml of dioxane, at 0° C. and while stirring. After stirring for 5 hours at 20° C., the mixture is poured into water/sodium chloride solution and the precipitate is filtered off. Yield 510 mg. After chromatography analogous to that indicated in Example 2 (g), dexamethasone 17-(methyl carbonate)-21-cyclopropanecarboxylate with a melting point of 274° C. is obtained from acetone/ether.

IR: 3,460, 1,735, 1,655, 1,610, 1,435 and 1,270 cm$^{-1}$
MS spectrum: M$^+$ = 518

(f) 0.2 ml of propionyl chloride in 1 ml of dioxane is added dropwise at 0° to a solution of 700 mg of dexamethasone 17-(methyl carbonate) in 8.4 ml of pyridine and the mixture is then stirred for 3 hours at 22° C. It is poured into water and neutralized with dilute hydrochloric acid and the precipitate is filtered off, washed with water and dried. In the case of a further batch, with which the reaction product has precipitated as an oil, the oil is separated off and taken up in methylene chloride and the solution is washed with water and concentrated in vacuo. The reaction product obtained in each case is chromatographed as indicated in Example 2 g. After recrystallization from acetone/ether, 550 mg of dexamethasone 17-(methyl carbonate)-21-n-propionate with a melting point of 260° C. are obtained.

IR: 3,460, 1,735, 1,655, 1,610, 1,435 and 1,270 cm$^{-1}$
MS spectrum: M$^+$ = 506

(g) 700 mg of dexamethasone 17-(methyl carbonate) are reacted (1) with 0.2 ml of acetyl chloride, (2) with 0.3 ml of butyryl chloride, (3) with 0.4 ml of valeryl chloride and (4) with 1 ml of cyclopentylpropionyl chloride, instead of with propionyl chloride, and the product is worked up, in the same way as described in Example 3 (f).

The corresponding (1) dexamethasone 17-(methyl carbonate)-21-acetate, (2) dexamethasone 17-(methyl carbonate)-21-butyrate, (3) dexamethasone 17-(methyl carbonate)-21-valerate and (4) dexamethasone 17-(methyl carbonate)-21-cyclopentylpropionate is obtained in each case.

EXAMPLE 4

(a) A solution of 0.8 ml of methyl chloroformate in 1 ml of dioxane is added dropwise to a solution of 1 g of dexamethasone 17-(n-propyl carbonate) in 8 ml of dioxane and 4 ml of pyridine, at 0° C. and while stirring, and the reaction mixture is stirred for 16 hours at 22° C. It is then poured into 250 ml of half-saturated aqueous sodium chloride solution and the precipitate which has separated out is filtered off, washed and dried; TLC: $R_f$ = 0.60. In a further analogous batch, the precipitate is taken up in, or extracted with, methylene chloride. The methylene chloride solution is washed with water and the solvent is distilled off in vacuo, whereupon a residue remains. TLC: $R_f$ = 0.60. The yield is 900 mg in each case. In order to prepare the product in the pure form, the crude reaction product is chromatographed on silica gel (3 × 7 cm column) with methylene chloride. The fractions in which exclusively the desired reaction product is detected on the basis of the TLC diagram (TLC: $R_f$ = 0.60) are combined and crystallized from acetone/ether. 720 mg of dexamethasone 17-(n-propyl carbonate)-21-(methyl carbonate) with a melting point of 167° C. are obtained.

IR: 3,440, 1,730, 1,655, 1,610, 1,440 and 1,265 cm$^{-1}$
MS spectrum: M$^+$ = 536

(b) 1 g of dexamethasone 17-(n-propyl carbonate) is reacted (1) with 0.9 ml of ethyl chloroformate, (2) with 1.0 ml of n-propyl chloroformate, (3) with 1.1 ml of n-butyl chloroformate, (4) with 1.0 ml of isopropyl chloroformate, (5) with 1.1 ml of isobutyl chloroformate, (6) with 0.8 ml of acetyl chloride, (7) with 0.8 ml of propionyl chloride, (8) with 0.9 ml of butyryl chloride, (9) with 1 ml of valeryl chloride, (10) with 1 ml of cyclopropanecarboxylic acid chloride and (11) with 1.3 ml of cyclopentylpropionyl chloride, instead of with methyl chloroformate, and the product is worked up, in the same way as described in Example 4 (a).

The corresponding (1) dexamethasone 17-(n-propyl carbonate)-21-(ethyl carbonate), (2) dexamethasone 17-(n-propyl carbonate)-21-(n-propyl carbonate), (3) dexamethasone 17-(n-propyl carbonate)-21-(n-butyl carbonate), (4) dexamethasone 17-(n-propyl carbonate)-21-(isopropyl carbonate), (5) dexamethasone (17-(n-propyl carbonate)-21-(isobutyl carbonate), (6) dexamethasone 17-(n-propyl carbonate)-21-acetate, (7) dexamethasone 17-(n-propyl carbonate)-21-propionate, (8) dexamethasone 17-(n-propyl carbonate)-21-butyrate, (9) dexamethasone 17-(n-propyl carbonate)-21-valerate, (10) dexamethasone 17-(n-propyl carbonate)-21-cyclopropanecarboxylate and 11) dexamethasone 17-(n-propyl carbonate)-21-cyclopentylpropionate is obtained in each case.

(c) 3 g of dexamethasone 17-(n-propyl carbonate) are reacted with methanesulfonyl chloride, and the product is worked up, in the same way as described in Example 2 (f). After crystallization from acetone/ether, dexamethasone 17-(n-propyl carbonate)-21-methanesulfonate is obtained.

EXAMPLE 5

(a) 1 g of dexamethasone 17-(n-butyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of burtyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) dexamethasone 17-(n-butyl carbonate)-21-(methyl carbonate), (2) dexamethasone 17-(n-butyl carbonate)-21-(ethyl carbonate), (3) dexamethasone 17 (n-butyl carbonate)-21-(n-propyl carbonate), (4) dexamethasone 17-(n-butyl carbonate)-21-(n-butyl carbonate), (5) dexamethasone 17-(n-butyl carbonate)-21-(isopropyl carbonate), (6) dexamethasone 17-(n-butyl carbonate)-21-(isobutyl carbonate), (7) dexamethasone 17-(n-butyl carbonate)-21-acetate, (8) dexamethasone 17-(n-butyl carbonate)-21-propionate, (9) dexamethasone 17-(n-butyl carbonate)-21-butyrate, (10) dexamethasone 17-(n-butyl carbonate)-21-valerate, (11) dexamethasone 17-(n-butyl carbonate)-21-cyclopropanecarboxylate and (12) dexamethasone 17-(n-butyl carbonate)-21-cyclopentylpropionate is obtained in each case.

(b) 3 g of dexamethasone 17-(n-butyl carbonate) are reacted with methanesulfonyl chloride, and the product is worked up, in the same way as described in Example 2 (f). After crystallization from ether, dexamethasone 17-(n-butyl carbonate)-21-methanesulfonate is obtained.

EXAMPLE 6

(a) 1 g of dexamethasone 17-(n-pentyl carbonate) is reacted (1) with 0.8 ml of methyl chloroformate and (2) with 0.9 ml of ethyl chloroformate, (3) with 1.0 ml of n-propyl chloroformate, (4) with 1.0 ml of n-butyl chloroformate, (5) with 1.0 ml of n-pentyl chloroformate, (6) with 0.8 ml of acetyl chloride, (7) with 0.8 ml of propionyl chloride, (8) with 0.9 ml of valeryl chloride and (9) with 1 ml of cyclopropanecarboxylic acid chloride, instead of with methyl chloroformate, and the product is worked up, in the same way as described in Example 4 (a).

The corresponding (1) dexamethasone 17-(n-pentyl carbonate)-21-(methyl carbonate), (2) dexamethasone 17-(valeryl carbonate)-21-(ethyl carbonate), (3) dexamethasone 17-(valeryl carbonate)-21-(n-propyl carbonate), (4) dexamethasone 17-(n-pentyl carbonate)-21-(n-butyl carbonate), (5) dexamethasone 17-(n-pentylcarbonate)-21-(n-pentyl carbonate), (6) dexamethasone 17-(n-pentylcarbonate)-21-acetate, (7) dexamethasone 17-(n-pentylcarbonate)-21-propionate, (8) dexamethasone 17-(n-pentyl carbonate)-21-valerate and (9) dexamethasone 17-(n-pentyl carbonate)-21-cyclopropanecarboxylate is obtained in each case.

(b) 3 g of dexamethasone 17-(n-pentyl carbonate) are reacted with methanesulfonyl chloride, and the product is worked up, in the same way as described in Example 2 (f). Dexamethasone 17-(n-pentyl carbonate)-21-methanesulfonate is thus obtained.

EXAMPLE 7

6α-Fluoro-prednisolone 17α-(ethyl carbonate)-21-propionate 5.4 g of 6α-fluoro-prednisolone 17α,21-(diethyl orthocarbonate) are stirred in 200 ml of glacial acetic acid and 2 ml of water for 5 hours at 20° C. The reaction mixture is then stirred into 1.5 l of half-saturated sodium chloride solution. The precipitate which then separates out is filtered off, washed with water and dried.

The 4.45 g of 6α-fluoro-prednisolone 17α-(ethyl carbonate) with a melting point of 133°-136° C., which are thus obtained can immediately be further reacted as follows, without further purification.

For this purpose, the above substance is dissolved in 60 ml of absolute pyridine and, after cooling the solution to 0° C., 2.3 ml of propionyl chloride are added. After 1 hour at 0° C. and a further hour at 20° C., the reaction mixture is stirred into 500 ml of half-saturated aqueous sodium chloride solution. The mixture is then extracted with methylene chloride and the organic phase is washed with water, with dilute hydrochloric acid and with water until neutral, dried and evaporated to dryness in vacuo. The resulting 4.95 g of crude 6α-fluoroprednisolone 17α-(ethyl carbonate)-21-propionate can be purified as follows.

For this purpose, the product is chromatographed on a column of 250 g of silica gel, and worked up, as described in Example 2 a. In this case the product is finally recrystallized from ether/petroleum ether and 2.55 g of 6α-fluoroprednisolone 17α-(ethyl carbonate)-21-propionate with a melting point of 147°-148° C. are obtained.

The 6α-fluoro-prednisolone 17α,21-(diethyl orthocarbonate) used as the starting material is obtained analogously in accordance with German Pat. No. 1,668,079, as follows.

After adding 13 ml of tetraethyl orthocarbonate and 0.29 g of p-toluenesulfonic acid, a solution of 4.75 g of 6α-fluoro-prednisolone in 180 ml of anhydrous dioxane is stirred at room temperature for 15 hours. The reaction mixture is then poured into a solution of 1.5 g of sodium bicarbonate in 950 ml of water. The crystals which have precipitated out are collected, washed with water, dried and recrystallized from acetone.

4.1 g of 6α-fluoro-prednisolone 17α,21-(diethyl orthocarbonate) with a melting point of 178°-180° C. are obtained.

EXAMPLE 8

6α-Fluoro-prednisolone 17α-(ethyl carbonate)-21-chloroacetate 4 g of 6α-fluoro-prednisolone 17α-(ethyl carbonate) are dissolved in 110 ml of absolute tetrahydrofuran, 1.69 g of chloroacetic anhydride and 0.65 ml of absolute pyridine are added and the mixture is stirred at room temperature for 28 hours.

20 ml of water are then added and the resulting mixture is evaporated to dryness in a rotary evaporator, in vacuo and under a high vacuum at a bath temperature of 40° C. The residue is taken up in 150 ml of ethyl acetate, the solution is washed with 12 ml of 2 N hydrochloric acid, with water, with dilute sodium bicarbonate solution and with water until neutral and the organic phase is dried over sodium sulfate and again evaporated to dryness in vacuo. The residue is recrystallized from diisopropyl ether/petroleum ether.

3.9 g of 6α-fluoro-prednisolone 17α-(ethyl carbonate)-21-chloroacetate with a melting pont of 134°-138° are obtained.

EXAMPLE 9

6α-Fluoro-prednisolone 17α-(ethyl carbonate)-21-(morpholinoacetate hydrochloride)

0.5 g of 6α-fluoro-prednisolone 17α-(ethyl carbonate)-21-chloroacetate and 0.4 ml of morpholine in 16 ml of acetone are heated to boiling under reflux for 3 hours. The reaction mixture is then evaporated in vacuo, the residue is dissolved in 10 ml of ethyl acetate and the solution is extracted by shaking 3 times with, in each case, 15.5 ml of 0.10 N hydrochloric acid. The combined aqueous phases are then rendered weakly alkaline with sodium bicarbonate solution. The precipitate which has separated out is collected, washed with a little water and dissolved in ethyl acetate and the solution is dried over sodium sulfate and evaporated to dryness in vacuo. The residue is taken up in 5 ml of absolute ethanol and 3.2 ml of 0.30 N hydrogen chloride in absolute ethanol are added. The mixture is then again concentrated to dryness in vacuo and the residue is made to crystallize with hexane.

290 mg of 6α-fluoro-prednisolone 17α-(ethyl carbonate)-21-(morpholinoacetate hydrochloride) with a melting point of 185°-188° C. are obtained.

EXAMPLE 10

6α-Methyl-prednisolone 17α-(ethyl carbonate)

21.0 g of 6α-methyl-prednisolone 17α,21-(diethyl orthocarbonate) are stirred in a mixture of 700 ml of glacial acetic acid and 1.0 ml of water for 2 hours at room temperature. The mixture is then poured into 3.0 l of ice-water, the resulting mixture is neutralized with 875 ml of concentrated aqueous ammonia solution and the precipitate which has separated out is filtered off and washed with a little water. The combined filtrates are extracted with methylene chloride and the above filter residue is dissolved in the organic phase and the latter is dried over sodium sulfate and evaporated to dryness in vacuo. After recrystallization from a little methylene chloride and ether, 16.7 g of 6α-methyl-prednisolone 17α-(ethyl carbonate) with a melting point of 188°-190° C. are obtained.

6α-Methyl-prednisolone 17α,21-(diethyl carbonate), which is used as the starting material, is obtained analogously according to German Pat. No. 1,668,079, as follows. After adding 47.0 ml of tetraethyl orthocarbonate and 1.05 g of p-toluenesulfonic acid, a solution of 17 g of urbasone in 600 ml of anhydrous dioxane is stirred for 5 hours at room temperature. The reaction mixture is then poured into a solution of 6.0 g of sodium bicarbonate in 4.0 l of water. The mixture is then worked up as described under Example 7. 21.1 g of 6α-methyl-prednisolone 17α,21-(diethyl carbonate) with a melting point of 109°–112° C. are obtained.

EXAMPLE 11

6α-Methyl-prednisolone 17α-(ethyl carbonate)-21-(methyl carbonate)

8.5 g of 6α-methyl-prednisolone 17α-(ethyl carbonate) are dissolved in a mixture of 85 ml of anhydrous dioxane and 42 ml of anhydrous pyridine. 7.2 ml of methyl chloroformate are then added dropwise at 0° C., with ice-cooling and whilst stirring. After standing for 15 hours at 0° C., the mixture is stirred into 800 ml of half-concentrated aqueous sodium chloride solution. After standing for 3 hours, the crystals which have precipitated out are collected, washed with water and dried in vacuo at 60° C.

After recrystallization from diisopropyl ether/hexane, 8.2 g of 6α-methyl-prednisolone 17α-(ethyl carbonate)-21-(methyl carbonate) with a melting point of 121°–123° C. are obtained.

EXAMPLE 12

6α-Methyl-prednisolone 17α,21-bis-(ethyl carbonate)

A solution of 2.3 g (=2 ml) of ethyl chloroformate in 18 ml of absolute dioxane was added dropwise to an ice-cold solution of 3.2 g of 6α-methyl-prednisolone 17α-(ethyl carbonate) in 10.5 ml of anhydrous pyridine, with ice-cooling and whilst stirring. After 4½ hours at 0° C., the reaction mixture was stirred into 200 ml of half-saturated sodium chloride solution. The resulting mixture was then extracted 3 times by shaking with, in each case, 100 ml of methylene chloride. The combined organic phases were washed with 0.5 N hydrochloric acid and with water until neutral, dried over sodium sulfate and concentrated to dryness in vacuo. 3.15 g of crude 6α-methyl-prednisolone 17α,21-bis-(ethyl carbonate) with a melting point of 136°–140° C. are obtained. For further purification, the product is subjected to fractional chromatography in a 4×10 cm column of silica gel using methylene chloride as the eluting agent. The fractions which are a single compound according to thin layer chromatography were combined and evaporated to dryness in vacuo. After digesting with diisopropyl ether, 2.3 g of 6α-methyl-prednisolone 17α,21-bis-(ethyl carbonate) with a melting point of 142°–143° C. are obtained.

EXAMPLE 13

6α-Methyl-prednisolone 17α-(ethyl carbonate)-21-propionate 0.78 ml of propionyl chloride are stirred into a solution of 3.0 g of 6α-methyl-prednisolone 17α-(ethyl carbonate) in 36 ml of pyridine, with ice-cooling.

Subsequently, the reaction mixture was stirred for 30 minutes at 0° C. and then for 1 hour at room temperature and was finally poured into 200 ml of aqueous sodium chloride solution. Further working-up of the reaction mixture was as described in Example 12.

After chromatography and crystallization with diisopropyl ether, 2.4 g of 6α-methyl-prednisolone 17α-(ethyl carbonate)-21-propionate with a melting point of 156°–158° C. were obtained.

EXAMPLE 14

6α-Methyl-prednisolone 17α-(ethyl carbonate)-21-cyclopropanecarboxylate 1.0 ml of cyclopropanecarboxylic acid chloride is stirred into a solution of 5.23 g of 6α-methyl-prednisolone 17α-(ethyl carbonate) in 60 ml of absolute pyridine, with ice-cooling. The mixture was stirred for 30 minutes at 0° C. and then left to stand for a further 16 hours at room temperature. After stirring into 350 ml of water, the reaction mixture is worked up and chromatographed (on 180 g of silica gel) as described in Example 12. After recrystallization from diisopropyl ether/hexane, 3.93 g of 6α-methyl-prednisolone 17α-(ethyl carbonate)-21-cyclopropanecarboxylate with a melting point of 167°–170° C. are obtained.

EXAMPLE 15

6α-Methyl-prednisolone 17α-(ethyl carbonate)-21-(1-adamantoate)

1.73 g of adamantanecarboxylic acid chloride and 1.0 ml of absolute pyridine are added to a solution of 2.0 g of 6α-methyl-prednisolone in 130 ml of toluene and the mixture is then heated to boiling under reflux for 15 hours. It is cooled to room temperature and washed with sodium bicarbonate solution and then with water until neutral, dried over sodium sulfate and concentrated to dryness in vacuo.

The residue is chromatographed on 100 g of silica gel by means of toluene/ethyl acetate, 3:1 (compare Example 12). After digesting with ether, 1.1 g of 6α-methyl-prednisolone 17α-(ethyl carbonate)-21-(1-adamantoate) with a melting point of 265°–266° C. are obtained.

EXAMPLE 16

6α-Methyl-prednisolone 17α-(ethyl carbonate)-21-cyclopentylpropionate 6.4 g of cyclopentylpropionyl chloride are added dropwise, under nitrogen, in the course of 30 minutes to a solution, at 30° C., of 5.0 g of 6α-methyl-prednisolone 17α-(ethyl carbonate) in a mixture of 23 ml of anhydrous pyridine and 25 ml of anhydrous acetone, while stirring. The mixture is then stirred for a further one hour at 46°–48° C. 2.17 ml of diethylaminoethanol were then added dropwise at this temperature in the course of 5 minutes, while stirring, and the mixture was stirred for a further 20 minutes. It is then cooled to 20° C. and 30 ml of water are stirred in in the course of 20 minutes. After stirring for a further 20 minutes, the organic solvent is evaporated off in vacuo and the residue is then worked up, and chromatographed, as described in Example 12.

2.6 g of 6α-methyl-prednisolone 17α-(ethyl carbonate)-21-cyclopentylpropionate with a melting point of 175°–176° C. are obtained.

EXAMPLE 17

(a) 1 g of prednisolone 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of iso-butyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) prednisolone 17-(methyl carbonate)-21-(methyl carbonate), (2) prednisolone 17-(methyl carbonate)-21-(ethyl carbonate), (3) prednisolone 17-(methyl carbonate)-21-(n-propyl carbonate), (4) prednisolone 17-(methyl carbonate)-21-(n-butyl carbonate), (5) prednisolone 17-(methyl carbonate)-21-(isopropyl carbonate), (6) prednisolone 17-(methyl carbonate)-21-(isobutyl carbonate), (7) prednisolone 17-(methyl carbonate)-21-acetate, (8) prednisolone 17-(methyl carbonate)-21-propionate, (9) prednisolone 17-(methyl carbonate)-21-butyrate, (10) prednisolone 17-(methyl carbonate)-21-valerate, (11) prednisolone 17-(methyl carbonate)-21-cyclopropanecarboxylate and (12) prednisolone 17-(methyl carbonate)-21-cyclopentylpropionate is obtained in each case.

(b) 3 g of prednisolone 17-(methyl carbonate) are reacted with methanesulfonyl chloride, and the product is worked up, in the same way as described in Example 2 (f). After crystallization from ether, prednisolone 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding prednisolone 17-(methyl carbonate)-21-p-toluenesulfonate and, respectively, prednisolone 17-(methyl carbonate)-21-p-chlorobenzenesulfonate are obtained.

(c) The prednisolone dimethyl orthocarbonate ($R_f \approx 0.6$), first required for the reaction, is prepared according to German Pat. No. 1,668,079 from prednisolone and tetramethyl orthocarbonate.

Subsequently the first-mentioned compound is hydrolyzed to prednisolone 17-(methyl carbonate) ($R_f \approx 0.4$) in the same way as described in Example 1 (c).

EXAMPLE 18

(a) 1 g of prednisone 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) prednisone 17-(methyl carbonate)-21-(methyl carbonate), (2) prednisone 17-(methyl carbonate)-21-(ethyl carbonate), (3) prednisone 17-(methyl carbonate)-21-(n-propyl carbonate), (4) prednisone 17-(methyl carbonate)-21-(n-butyl carbonate), (5) prednisone 17-(methyl carbonate)-21-(isopropyl carbonate), (6) prednisone 17-(methyl carbonate)-21-(isobutyl carbonate), (7) prednisone 17-(methyl carbonate)-21-acetate, (8) prednisone 17-(methyl carbonate)-21-propionate, (9) prednisone 17-(methyll carbonate)-21-butyrate, (10) prednisone 17-(methyl carbonate)-21-valerate, (11) prednisone 17-(methyl carbonate)-21-cyclopropanecarboxylate and (12) prednisone 17-(methyl carbonate)-21-cyclopentylpropionate is obtained in each case.

(b) 3 g of prednisone 17-(methyl carbonate) are reacted with methanesulfonyl chloride, and the product is worked up, in the same way as described in Example 2 (f). After crystallization from ether, prednisone 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding prednisone 17-(methyl carbonate)-21-p-toluenesulfonate or, respectively, prednisone 17-(methyl carbonate)-21-p-chlorobenzenesulfonate is obtained.

(c) The prednisone dimethyl orthocarbonate ($R_f \approx 0.6$), first required for the reaction, is prepared according to German Pat. No. 1,668,079 from prednisone and tetramethyl orthocarbonate.

Subsequently, the first-mentioned compound is hydrolyzed to prednisone 17-(methyl carbonate) ($R_f \approx 0.4$) in the same way as described in Example 1 (c).

EXAMPLE 19

(a) 1 g of cortisone 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) cortisone 17-(methyl carbonate)-21-(methyl carbonate), (2) cortisone 17-(methyl carbonate)-21-(ethyl carbonate), (3) cortisone 17-(methyl carbonate)-21-(n-propyl carbonate), (4) cortisone 17-(methyl carbonate)-21-(n-butyl carbonate), (5) cortisone 17-(methyl carbonate)-21-(isopropyl carbonate), (6) cortisone 17-(methyl carbonate)-21-(isobutyl carbonate), (7) cortisone 17-(methyl carbonate)-21-acetate, (8) cortisone 17-(methyl carbonate)-21-propionate, (9) cortisone 17-(methyl carbonate)-21-butyrate, (10) cortisone 17-(methylcarbonate)-21-valerate, (11) coritisone 17-(methyl carbonate)-21-cyclopropanecarboxylate and (12) cortisone 17-(methyl carbonate)-21-cyclopentylpropionate is obtained in each case.

(b) 3 g of cortisone 17-(methyl carbonate) are reacted with methanesulfonyl chloride, and the product is worked up, in the same way as described in Example 2 (f). After crystallization from ether, cortisone 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding cortisone 17-(methyl carbonate)-21-p-toluenesulfonate or, respectively, cortisone 17-(methyl carbonate)-21-p-chlorobenzenesulfonate is obtained.

(c) The cortisone dimethyl orthocarbonate ($R_f \approx 0.6$), first required for the reaction, is prepared according to German Pat. No. 1,668,079 from cortisone and tetramethyl orthocarbonate.

Subsequently, the first-mentioned compound is hydrolyzed to cortisone 17-(methyl carbonate) ($R_f \approx 0.4$) in the same way as described in Example 1 (c).

EXAMPLE 20

(a) 1 g of cortisol 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) cortisol 17-(methyl carbonate)-21-(methyl carbonate), (2) cortisol 17-(methyl carbonate)-21-(ethyl carbonate), (3) cortisol 17-(methyl carbonate)-21-(n-propyl carbonate), (4) cortisol 17-(methyl carbonate)-21-(n-butyl carbonate), (5) cortisol 17-(methyl carbonate)-21-(isopropyl carbonate), (6) cortisol 17-(methyl carbonate)-21-(isobutyl carbonate), (7) cortisol 17-(methyl carbonate)-21-acetate, (8) cortisol 17-(methyl carbonate)-21-propionate, (9) cortisol 17-(methyl carbonate)-21-butyrate, (10) cortisol 17-(methyl carbonate)-21-valerate, (11) cortisol 17-(methyl carbonate)-21-cyclopropanecarboxylate and (12) cortisol 17-(methyl carbonate)-21-cyclopentylpropionate is obtained in each case.

(b) 3 g of cortisol 17-(methyl carbonate) are reacted with methanesulfonyl chloride, and the product is worked up, in the same way as described in Example 2 (f). After crystallization from ether, cortisol 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding cortisol 17-(methyl carbonate)-21-p-toluenesulfonate or, respectively, cortisol 17-(methyl carbonate)-21-p-chlorobenzenesulfonate is obtained.

(c) The cortisol dimethyl orthocarbonate ($R_f \approx 0.6$) first required for the reaction is prepared according to German Pat. No. 1,668,079 from cortisol and tetramethyl orthocarbonate.

Subsequently, the first-mentioned compound is hydrolyzed to cortisol 17-(methyl carbonate) ($R_f \approx 0.4$) in the same way as described in Example 1 (c).

EXAMPLE 21

(a) 1 g of beclomethasone 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) beclomethasone 17-(methyl carbonate)-21-(methyl carbonate), (2) beclomethasone 17-(methyl carbonate)-21-(ethyl carbonate), (3) beclomethasone 17-(methyl carbonate)-21-(n-propyl carbonate), (4) beclomethasone 17-(methyl carbonate)-21-(n-butyl carbonate), (5) beclomethasone 17-(methyl carbonate)-21-(isopropyl carbonate), (6) becomethasone 17-(methyl carbonate)-21-(isobutyl carbonate), (7) beclomethasone 17-(methyl carbonate)-21-acetate, (8) beclomethasone 17-(methyl carbonate)-21-propionate, (9) beclomethasone 17-(methyl carbonate)-21-butyrate, (10) beclomethasone 17-(methyl carbonate)-21-valerate, (11) beclomethasone 17-(methyl carbonate)-21-cyclopropanecarboxylate and (12) beclomethasone 17-(methyl carbonate)-21-cyclopentylpropionate is obtained in each case.

(b) 3 g of beclomethasone 17-(methyl carbonate) are reacted with methanesulfonyl chloride, and the product is worked up, in the same way as described in Example 2 (f). After crystallization from ether, beclomethasone 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding beclomethasone 17-(methyl carbonate)-21-p-toluenesulfonate or, respectively, beclomethasone 17-(methyl carbonate)-21-p-chlorobenzenesulfonate is obtained.

(c) The beclomethasone dimethyl orthocarbonate ($R_f \approx 0.6$) first required for the reaction is prepared according to German Pat. No. 1,668,079 from beclomethasone and tetramethyl orthocarbonate. Subsequently, the first-mentioned compound is hydrolyzed to beclomethasone 17-(methyl carbonate) ($R_f \approx 0.4$) in the same way as described in Example 1 (c).

EXAMPLE 22

(a) 1 g of 6α-fluorodexamethasone 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 6α-fluorodexamethasone 17-(methyl carbonate)-21-(methyl carbonate), (2) 6α-fluorodexamethasone 17-(methyl carbonate)-21-(ethyl carbonate), (3) 6α-fluorodexamethasone 17-(methyl carbonate)-21-(n-propyl carbonate), (4) 6α-fluorodexamethasone 17-(methyl carbonate)-21-(n-butyl carbonate), (5) 6α-fluorodexamethasone 17-(methyl carbonate)-21-(isopropyl carbonate), (6) 6α-fluorodexamethasone 17-(methyl carbonate)-21-(isobutyl carbonate), (7) 6α-fluorodexamethasone 17-(methyl carbonate)-21-acetate, (8) 6α-fluorodexamethasone 17-(methyl carbonate)-21-propionate, (9) 6α-fluorodexamethasone 17-(methyl carbonate)-21-butyrate, (10) 6α-fluorodexamethasone 17-(methyl carbonate)-21-valerate, (11) 6α-fluorodexamethasone 17-(methyl carbonate)-21-cyclopropanecarboxylate and (12) 6α-fluorodexamethasone 17-(methyl carbonate)-21-cyclopentylpropionate is obtained in each case.

(b) 3 g of 6α-fluorodexamethasone 17-(methyl carbonate) are reacted with methanesulfonyl chloride, and the product is worked up, in the same way as described in Example 2 (f). After crystallization from ether, 6α-fluorodexamethasone 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α-fluorodexamethylsone 17-(methyl carbonate)-21-p-toluenesulfonate or, respectively, 6α-fluorodexamethasone 17-(methyl carbonate)-21-p-chlorobenzenesulfonate is obtained.

(c) The 6α-fluorodexamethasone dimethyl orthocarbonate ($R_f \approx 0.6$) first required for the reaction is prepared according to German Pat. No. 1,668,079 from 6α-fluorodexamethasone and tetramethyl orthocarbonate.

Subsequently, the first-mentioned compound is hydrolyzed to 6α-fluorodexamethasone 17-(methyl carbonate) ($R_f \approx 0.4$) in the same way as described in Example 1 (c).

EXAMPLE 23

(a) 1 g of betamethasone 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of iso-butyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) betamethasone 17-(methyl carbonate)-21-(methyl carbonate), (2) betamethasone 17-(methyl carbonate)-21-(ethyl carbonate), (3) betamethasone 17-(methyl carbonate)-21-(n-propyl carbonate), (4) betamethasone 17-(methyl carbonate)-21-(n-butyl carbonate), (5) betamethasone 17-(methyl carbonate)-21-(isopropyl carbonate), (6) betamethasone 17-(methyl carbonate)-21-(isobutyl carbonate), (7) betamethasone 17-(methyl carbonate)-21-acetate, (8) betamethasone 17-(methyl carbonate)-21-propionate, (9) betamethasone 17-(methyl carbonate)-21-butyrate, (10) betamethasone 17-(methyl carbonate)-21-valerate, (11) betamethasone 17-(methyl carbonate)-21-cyclopropanecarboxylate and (12) betamethasone 17-(methyl carbonate)-21-cyclopentylpropionate is obtained in each case.

(b) 3 g of betamethasone 17-(methyl carbonate) are reacted with methanesulfonyl chloride, and the product is worked up, in the same way as described in Example 2 (f). After crystallization from ether, betamethasone 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding betamethasone 17-(methyl carbonate)-21-p-toluenesulfonate or, respectively, betamethasone 17-(methyl carbonate)-21-p-chlorobenzenesulfonate is obtained.

(c) The betamethasone dimethyl orthocarbonate ($R_f \approx 0.6$) first required for the reaction is prepared according to German Pat. No. 1,668,079 from betamethasone and tetramethyl orthocarbonate. Subsequently, the first-mentioned compound is hydrolyzed to betamethasone 17-(methyl carbonate) ($R_f \approx 0.4$) in the same way as described in Example 1(c).

EXAMPLE 24

(a) 1 g of 6α-fluoro-prednisolone 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 6α-fluoro-prednisolone 17-(methyl carbonate)-21-(methyl carbonate), (2) 6α-fluoro-prednisolone 17-(methyl carbonate)-21-(ethyl carbonate), (3) 6α-fluoro-prednisolone 17-(methyl carbonate)-21-(n-propyl carbonate), (4) 6α-fluoro-prednisolone 17-(methyl carbonate)-21-(n-butyl carbonate), (5) 6α-fluoro-prednisolone 17-(methyl carbonate)-21-(isopropyl carbonate), (6) 6α-fluoro-prednisolone 17-(methyl carbonate)-21-(isobutyl carbonate), (7) 6α-fluoro-prednisolone 17-(methyl carbonate)-21-acetate, (8) 6α-fluoro-prednisolone 17-(methyl carbonate)-21-propionate, (9) 6α-fluoro-prednisolone 17-(methyl carbonate)-21-butyrate, (10) 6α-fluoro-prednisolone 17-(methyl carbonate)-21-valerate, (11) 6α-fluoro-prednisolone 17-(methyl carbonate)-21-cyclopropanecarboxylate and (12) 6α-fluoro-prednisolone 17-(methyl carbonate)-21-cyclopentylpropionate is obtained in each case.

(b) 3 g of 6α-fluoro-prednisolone 17-(methyl carbonate) are reacted with methanesulfonyl chloride, and the product is worked up, in the same way as described in Example 2 (f). After crystallization from ether, 6α-fluoro-prednisolone 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α-fluoro-prednisolone 17-(methyl carbonate)-21-p-toluenesulfonate or, respectively, 6α-fluoro-prednisolone 17-(methyl carbonate)-21-p-chlorobenzenesulfonate is obtained.

(c) The 6α-fluoro-prednisolone dimethyl orthocarbonate ($R_f \approx 0.6$) first required for the reaction is prepared according to German Pat. No. 1,668,079 from 6α-fluoro-prednisolone and tetramethyl orthocarbonate.

Subsequently, the first-mentioned compound is hydrolyzed to 6α-fluoro-prednisolone 17-(methyl carbonate) ($R_f \approx 0.4$) in the same way as described in Example 1 (c).

EXAMPLE 25

(a) 1 g of 16α- or β-methylprednisolone 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 16α- or β-methylprednisolone 17-(methyl carbonate)-21-(methyl carbonate), (2) 16α- or β-methylprednisolone 17-(methyl carbonate)-21-(ethyl carbonate), (3) 16α- or β-methylprednisolone 17-(methyl carbonate)-21-(n-propyl carbonate), (4) 16α- or β-methylprednisolone 17-(methyl carbonate)-21-(n-butyl carbonate), (5) 16α- or β-methylprednisolone 17-(methyl carbonate)-21-(isopropyl carbonate), (6) 16α- or β-methylprednisolone 17-(methyl carbonate)-21-(isobutyl carbonate), (7) 16α- or β-methylprednisolone 17-(methyl carbonate)-21-acetate, (8) 16α- or β-methylprednisolone 17-(methyl carbonate)-21-propionate, (9) 16α- or β-methylprednisolone 17-(methyl carbonate)-21-butyrate, (10) 16α- or β-methylprednisolone 17-(methyl carbonate)-21-valerate, (11) 16α- or β-methyl-prednisolone 17-(methyl carbonate)-21-cyclopropanecarboxylate and (12) 16α- or β-methylprednisolone 17-(methyl carbonate)-21-cyclopentylpropionate is obtained in each case.

(b) 3 g of 16α- or β-methylprednisolone 17-(methyl carbonate) are reacted with methanesulfonyl chloride, and the product is worked up, in the same way as described in Example 2 (f). After crystallization from ether, 16α- or β-methylprednisolone 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 16α- or β-methylprednisolone 17-(methyl carbonate)-21-p-toluenesulfonate or, respectively, 16α- or β-methylprednisolone 17-(methyl carbonate)-21-p-chlorobenzenesulfonate is obtained.

(c) The 16α- or β-methylprednisolone dimethyl orthocarbonate (R$_f$≃0.6) first required for the reaction is prepared according to German Pat. No. 1,668,079 from 16α- or β-methyl-prednisolone and tetramethyl orthocarbonate.

Subsequently, the first-mentioned compound is hydrolyzed to 16α- or β-methylprednisolone 17-(methyl carbonate) (R$_f$≃0.4) in the same way as described in Example 1 (c).

EXAMPLE 26

(a) 1 g of 6α,16α- or β-dimethyl-prednisolone 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 6α,16α- or β-dimethyl-prednisolone 17-(methyl carbonate)-21-(methyl carbonate), (2) 6α,16α- or β-dimethyl-prednisolone 17-(methyl carbonate)-21-(ethyl carbonate), (3) 6α,16α- or β-dimethyl-prednisolone 17-(methyl carbonate)-21-(n-propyl carbonate), (4) 6α,16α- or β-dimethyl-prednisolone 17-(methyl carbonate)-21-(n-butyl carbonate), (5) 6α,16α-or β-dimethyl-prednisolone 17-(methyl carbonate)-21-(isopropyl carbonate), (6) 6α,16α- or β-dimethyl-prednisolone 17-(methyl carbonate)-21-(isobutyl carbonate), (7) 6α,16α- or β-dimethylprednisolone 17-(methyl carbonate)-21-acetate, (8) 6α,16α- or β-dimethyl-prednisolone 17-(methyl carbonate)-21-propionate, (9) 6α,16α- or β-dimethyl-prednisolone 17-(methyl carbonate)-21-butyrate, (10) 6α,16α- or β-dimethyl-prednisolone 17-(methyl carbonate)-21-valerate, (11) 6α,16α- or β-dimethyl-prednisolone 17-(methyl carbonate)-21-cyclopropanecarboxylate and (12) 6α,16α- or β-dimethyl-prednisolone 17-(methyl carbonate)-21-cyclopentylpropionate is obtained in each case.

(b) 3 g of 6α,16α- or β-dimethyl-prednisolone 17-(methyl carbonate) are reacted with methanesulfonyl chloride, and the product is worked up, in the same way as described in Example 2 (f). After crystallization from ether, 6α,16α- or β-dimethyl-prednisolone 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α,16α- or β-dimethyl-prednisolone 17-(methyl carbonate)-21-p-toluenesulfonate or, respectively, 6α,16α- or β-dimethyl-prednisolone 17-(methyl carbonate)-21-p-chlorobenzenesulfonate is obtained.

(c) The 6α,16α- or β-dimethyl-prednisolone dimethyl orthocarbonate (R$_f$≃0.6) first required for the reaction is prepared according to German Pat. No. 1,668,079 from 6α,16α- or β-dimethyl-prednisolone and tetramethyl orthocarbonate.

Subsequently, the first-mentioned compound is hydrolyzed to 6α,16α- or β-dimethyl-prednisolone 17-(methyl carbonate) (R$_f$≃0.4) in the same way as described in Example 1 (c).

EXAMPLE 27

(a) 1 g of 9α-chloro-16α-methyl-prednisolone 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 9α-chloro-16α-methyl-prednisolone 17-(methyl carbonate)-21-(methyl carbonate), (2) 9α-chloro-16α-methyl-prednisolone 17-(methyl carbonate)-21-(ethyl carbonate), (3) 9α-chloro-16α-methyl-prednisolone 17-(methyl carbonate)-21-(n-propyl carbonate), (4) 9α-chloro-16α-methyl-prednisolone 17-(methyl carbonate)-21-(n-butyl carbonate), (5) 9α-chloro-16α-methyl-prednisolone 17-(methyl carbonate)-21-(isopropyl carbonate), (6) 9α-chloro-16α-methyl-prednisolone 17-(methyl carbonate)-21-(isobutyl carbonate), (7) 9α-chloro-16α-methyl-prednisolone 17-(methyl carbonate)-21-acetate, (8) 9α-chloro-16α-methyl-prednisolone 17-(methyl carbonate)-21-propionate, (9) 9α-chloro-16α-methyl-prednisolone 17-(methyl carbonate)-21-butyrate, (10) 9α-chloro-16α-methyl-prednisolone 17-(methyl carbonate)-21-valerate, (11) 9α-chloro-16α-methyl-prednisolone 17-(methyl carbonate)-21-cyclopropanecarboxylate and (12) 9α-chloro-16α-methyl-prednisolone 17-(methyl carbonate)-21-cyclopentylpropionate is obtained in each case.

(b) 3 g of 9α-chloro-16α-methyl-prednisolone 17-(methyl carbonate) are reacted with methanesulfonyl chloride, and the product is worked up, in the same way as described in Example 2 (f). After crystallization from ether, 9α-chloro-16α-methyl-prednisolone 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 9α-chloro-16α-methyl-prednisolone 17-(methyl carbonate)-21-p-toluenesulfonate or, respectively, 9α-chloro-16α-methyl-prednisolone 17-(methyl carbonate)-21-p-chlorobenzenesulfonate is obtained.

(c) The 9α-chloro-16α-methyl-prednisolone dimethyl orthocarbonate ($R_f \approx 0.6$) first required for the reaction is prepared according to German Pat. No. 1,668,079 from 9α-chloro-16α-methyl-prednisolone and tetramethyl orthocarbonate.

Subsequently, the first-mentioned compound is hydrolyzed to 9α-chloro-16α-methyl-prednisolone 17-(methyl carbonate) ($R_f \approx 0.4$) in the same way as described in Example 1 (c).

EXAMPLE 28

(a) 1 g of 9α-chloro-prednisolone 17-(methyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 9α-chloro-prednisolone 17-(methyl carbonate)-21-(methyl carbonate), (2) 9α-chloro-prednisolone 17-(methyl carbonate)-21-(ethyl carbonate), (3) 9α-chloro-prednisolone 17-(methyl carbonate)-21-(n-propyl carbonate), (4) 9α-chloro-prednisolone 17-(methyl carbonate)-21-(n-butyl carbonate), (5) 9α-chloro-prednisolone 17-(methyl carbonate)-21-(isopropyl carbonate), (6) 9α-chloro-prednisolone 17-(methyl carbonate)-21-(isobutyl carbonate), (7) 9α-chloro-prednisolone 17-(methyl carbonate)-21-acetate, (8) 9α-chloro-prednisolone 17-(methyl carbonate)-21-propionate, (9) 9α-chloro-prednisolone 17-(methyl carbonate)-21-butyrate, (10) 9α-chloro-prednisolone 17-(methyl carbonate)-21-valerate, (11) 9α-chloro-prednisolone 17-(methyl carbonate)-21-cyclopropanecarboxylate and (12) 9α-chloro-prednisolone 17-(methyl carbonate)-21-cyclopentylpropionate is obtained in each case.

(b) 3 g of 9α-chloro-prednisolone 17-(methyl carbonate) are reacted with methanesulfonyl chloride, and the product is worked up, in the same way as described in Example 2(f). After crystallization from ether, 9α-chloro-prednisolone 17-(methyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 9α-chloro-prednisolone 17-(methyl carbonate)-21-p-toluenesulfonate or, respectively, 9α-chloro-prednisolone 17-(methyl carbonate)-21-p-chlorobenzenesulfonate is obtained.

(c) The 9α-chloro-prednisolone dimethyl orthocarbonate ($R_f \approx 0.6$) first required for the reaction is prepared according to German Pat. No. 1,668,079 from 9α-chloro-prednisolone and tetramethyl orthocarbonate.

Subsequently, the first-mentioned compound is hydrolyzed to 9α-chloro-prednisolone 17-(methyl carbonate) ($R_f \approx 0.4$) in the same way as described in Example 1(c).

EXAMPLE 29

(a) 1 g of prednisolone 17-(ethyl carbonate) is reacted (1) with 0.8 ml of methyl chloroformate and (2) with 0.8 ml of ethyl chloroformate, (3) with 0.9 ml of n-propyl chloroformate, (4), with 0.9 ml of n-butyl chloroformate, (5) with 1.0 ml of isopropyl chloroformate, (6) with 1.0 ml of isobutyl chloroformate, (7) with 0.9 ml of butyryl chloride, (8) with 1 ml of valeryl chloride, (9) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) prednisolone 17-(ethyl carbonate)-21-(methyl carbonate), (2) prednisolone 17-(ethyl carbonate)-21-(ethyl carbonate), (3) prednisolone 17-(ethyl carbonate)-21-(n-propyl carbonate), (4) prednisolone 17-(ethyl carbonate)-21-(n-butyl carbonate), (5) prednisolone 17-(ethyl carbonate)-21-(isopropyl carbonate), (6) prednisolone 17-(ethyl carbonate)-21-(isobutyl carbonate), (7) prednisolone 17-(ethyl carbonate)-21-butyrate, (8) prednisolone 17-(ethyl carbonate)-21-valerate, (9) prednisolone 17-(ethyl carbonate)-21-cyclopropanecarboxylate and (10) prednisolone 17-(ethyl carbonate)-21-cyclopentylpropionate is obtained in each case.

(b) 3 g of prednisolone 17-(ethyl carbonate) are reacted with methanesulfonyl chloride, and the product is worked up, in the same way as described in Example 2(f). After crystallization from ether, prednisolone 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding prednisolone 17-(ethyl carbonate)-21-p-toluenesulfonate or, respectively, prednisolone 17-(ethyl carbonate)-21-p-chlorobenzenesulfonate is obtained.

(c) The prednisolone diethyl orthocarbonate ($R_f \approx 0.6$) first required for the reaction is prepared according to German Pat. No. 1,668,079 from prednisolone and tetraethyl orthocarbonate. Subsequently, the first-mentioned compound is hydrolyzed to prednisolone 17-(ethyl carbonate) ($R_f \approx 0.4$) in the same way as described in Example 1(c).

EXAMPLE 30

(a) 1 g of prednisone 17-(ethyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) prednisone 17-(ethyl carbonate)-21-(methyl carbonate), (2) prednisone 17-(ethyl carbonate)-21-(ethyl carbonate), (3) prednisone 17-(ethyl carbonate)-21-(n-propyl carbonate), (4) prednisone 17-(ethyl carbonate)-21-(n-butyl carbonate), (5) prednisone 17-(ethyl carbonate)-21-(isopropyl carbonate), (6) prednisone 17-(ethyl carbonate)-21-(isobutyl carbonate), (7) prednisone 17-(ethyl carbonate)-21-acetate, (8) prednisone 17-(ethyl carbonate)-21-propionate, (9) prednisone 17-(ethyl carbonate)-21-butyrate, (10) prednisone 17-(ethyl carbonate)-21-valerate, (11) prednisone 17-(ethyl carbonate)-21-cyclopropanecarboxylate and (12) prednisone 17-(ethyl carbonate)-21-cyclopentylpropionate is obtained in each case.

(b) 3 g of prednisone 17-(ethyl carbonate) are reacted with methanesulfonyl chloride, and the product is worked up, in the same way as described in Example 2(f). After crystallization from ether, prednisone 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding prednisone 17-(ethyl carbonate)-21-p-toluenesulfonate or, respectively, prednisone 17-(ethyl carbonate)-21-p-chlorobenzenesulfonate is obtained.

(c) The prednisone diethyl orthocarbonate ($R_f \approx 0.6$), first required for the reaction, is prepared according to German Pat. No. 1,668,079 from prednisone and tetraethyl orthocarbonate. Subsequently, the first-mentioned compound is hydrolyzed to prednisone 17-(ethyl carbonate) ($R_f \approx 0.4$) in the same way as described in Example 1(c).

EXAMPLE 31

(a) 1 g of cortisone 17-(ethyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) cortisone 17-(ethyl carbonate)-21-(methyl carbonate), (2) cortisone 17-(ethyl carbonate)-21-(ethyl carbonate), (3) cortisone 17-(ethyl carbonate)-21-(n-propyl carbonate), (4) cortisone 17-(ethyl carbonate)-21-(n-butyl carbonate), (5) cortisone 17-(ethyl carbonate)-21-(isopropyl carbonate), (6) cortisone 17-(ethyl carbonate)-21-(isobutyl carbonate), (7) cortisone 17-(ethyl carbonate)-21-acetate,(8) cortisone 17-(ethyl carbonate)-21-propionate, (9) cortisone 17-(ethyl carbonate)-21-butyrate, (10) cortisone 17-(ethyl carbonate)-21-valerate, (11) cortisone 17-(ethyl carbonate)-21-cyclopropanecarboxylate and (12) cortisone 17-(ethyl carbonate)-21-cyclopentylpropionate is obtained in each case.

(b) 3 g of cortisone 17-(ethyl carbonate) are reacted with methanesulfonyl chloride, and the product is worked up, in the same way as described in Example 2(f). After crystallization from ether, cortisone 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding cortisone 17-(ethyl carbonate)-21-p-toluenesulfonate or, respectively, cortisone 17-(ethyl carbonate)-21-p-chlorobenzenesulfonate is obtained.

(c) The cortisone diethyl orthocarbonate ($R_f \approx 0.6$) first required for the reaction is prepared according to German Pat. No. 1,668,079 from cortisone and tetraethyl orthocarbonate. Subsequently, the first-mentioned compound is hydrolyzed to cortisone 17-(ethyl carbonate) ($R_f \approx 0.4$) in the same way as described in Example 1(c).

EXAMPLE 32

(a) 1 g of cortisol 17-(ethyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.9 ml of butyryl chloride, (9) with 1 ml of valeryl chloride, (10) with 1 ml of cyclopropanecarboxylic acid chloride and (11) with 1.3 ml of cyclopentylpropionyl chloride, instead of with methyl chloroformate, and the product is worked up, in the same way as described in Example 4(a).

The corresponding (1) cortisol 17-(ethyl carbonate)-21-(methyl carbonate), (2) cortisol 17-(ethyl carbonate)-21-(ethyl carbonate), (3) cortisol 17-(ethyl carbonate)-21-n-propyl carbonate), (4) cortisol 17-(ethyl carbonate)-21-(n-butyl carbonate), (5) cortisol 17-(ethyl carbonate)-21-(isopropyl carbonate), (6) cortisol 17-(ethyl carbonate)-21-(isobutyl carbonate), (7) cortisol 17-(ethyl carbonate)-21-acetate, (8) cortisol 17-(ethyl carbonate)-21-butyrate, (9) cortisol 17-(ethyl carbonate)-21-valerate, (10) cortisol 17-(ethyl carbonate)-21-cyclopropanecarboxylate and (11) cortisol 17-(ethyl carbonate)-21-cyclopentylpropionate is obtained in each case.

(b) 3 g of cortisol 17-(ethyl carbonate) are reacted with methanesulfonyl chloride, and the product is worked up, in the same way as described in Example 2(f). After crystallization from ether, cortisol 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding cortisol 17-(ethyl carbonate)-21-p-toluenesulfonate or, respectively, cortisol 17-(ethyl carbonate)-21-p-chlorobenzenesulfonate is obtained.

(c) The cortisol diethyl orthocarbonate ($R_f \approx 0.6$) first required for the reaction is prepared according to German Pat. No. 1,668,079 from cortisol and tetraethyl orthocarbonate. Subsequently, the first-mentioned compound is hydrolyzed to cortisol 17-(ethyl carbonate) ($R_f \approx 0.4$) in the same way as described in Example 1(c).

EXAMPLE 33

(a) 1 g of beclomethasone 17-(ethyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) beclomethasone 17-(ethyl carbonate)-21-(methyl carbonate), (2) beclomethasone 17-(ethyl carbonate)-21-(ethyl carbonate), (3) beclomethasone 17-(ethyl carbonate)-21-(n-propyl carbonate), (4) beclomethasone 17-(ethyl carbonate)-21-(n-butyl carbonate), (5) beclomethasone 17-(ethyl carbonate)-21-(isopropyl carbonate), (6) beclomethasone 17-(ethyl carbonate)-21-(isobutyl carbonate), (7) beclomethasone 17-(ethyl carbonate)-21-acetate, (8) beclomethasone 17-(ethyl carbonate)-21-propionate, (9) beclomethasone 17-(ethyl carbonate)-21-butyrate, (10) beclomethasone 17-(ethyl carbonate)-21-valerate, (11) beclomethasone (17-(ethyl carbonate)-21-cyclopropanecarboxylate and (12)-beclomethasone 17-(ethyl carbonate)-21-cyclopentylpropionate is obtained in each case.

(b) 3 g of beclomethasone 17-(ethyl carbonate) are reacted with methanesulfonyl chloride, and the product is worked up, in the same way as described in Example 2(f). After crystallization from ether, beclomethasone 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding beclomethasone 17-(ethyl carbonate)-21-p-toluenesulfonate or, respectively, beclomethasone 17-(ethyl carbonate)-21-p-chlorobenzenesulfonate is obtained.

(c) The beclomethasone diethyl orthocarbonate ($R_f \approx 0.6$) first required for the reaction is prepared according to German Pat. No. 1,668,079 from beclomethasone and tetraethyl orthocarbonate. Subsequently, the first-mentioned compound is hydrolyzed to beclomethasone 17-(ethyl carbonate) ($R_f \approx 0.4$) in the same way as described in Example 1(c).

EXAMPLE 34

(a) 1 g of 6α-fluorodexamethasone 17-(ethyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) 6α-fluorodexamethasone 17-(ethyl carbonate)-21-(methyl carbonate), (2) 6α-fluorodexamethasone 17-(ethyl carbonate)-21-(ethyl carbonate), (3) 6α-fluorodexamethasone 17-(ethyl carbonate)-21-(n-propyl carbonate), (4) 6α-fluorodexamethasone 17-(ethyl carbonate)-21-(n-butyl carbonate), (5) 6α-fluorodexamethasone 17-(ethyl carbonate)-21-(isopropyl carbonate), (6) 6α-fluorodexamethasone 17-(ethyl carbonate)-21-(isobutyl carbonate), (7) 6α-fluorodexamethasone 17-(ethyl carbonate)-21-acetate, (8) 6α-fluorodexamethasone 17-(ethyl carbonate)-21-propionate, (9) 6α-fluorodexamethasone 17-(ethyl carbonate)-21-butyrate, (10) 6α-fluorodexamethasone 17-(ethyl carbonate)-21-valerate, (11) 6α-fluorodexamethasone 17-(ethyl carbonate)-21-cyclopropanecarboxylate and (12) 6α-fluorodexamethasone 17-(ethyl carbonate)-21-cyclopentylpropionate is obtained in each case.

(b) 3 g of 6α-fluorodexamethasone 17-(ethyl carbonate) are reacted with methanesulfonyl chloride, and the product is worked up, in the same way as described in Example 2(f). After crystallization from ether, 6α-fluorodexamethasone 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α-fluorodexamethasone 17-(ethyl carbonate)-21-p-toluenesulfonate or, respectively, 6α-fluorodexamethasone 17-(ethyl carbonate)-21-p-chlorobenzenesulfonate is obtained.

(c) The 6α-fluorodexamethasone diethyl orthocarbonate ($R_f \approx 0.6$) first required for the reaction is prepared according to German Pat. No. 1,668,079 from 6α-fluorodexamethasone and tetraethyl orthocarbonate.

Subsequently, the first-mentioned compound is hydrolyzed to 6α-fluorodexamethasone 17-(ethyl carbonate) ($R_f \approx 0.4$) in the same way as described in Example 1(c).

EXAMPLE 35

(a) 1 g of betamethasone 17-(ethyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) betamethasone 17-(ethyl carbonate)-21-(methyl carbonate), (2) betamethasone 17-(ethyl carbonate)-21-(ethyl carbonate), (3) betamethasone 17-(ethyl carbonate)-21-(n-propyl carbonate), (4) betamethasone 17-(ethyl carbonate)-21-(n-butyl carbonate), (5) betamethasone 17-(ethyl carbonate)-21-(isopropyl carbonate), (6) betamethasone 17-(ethyl carbonate)-21-(isobutyl carbonate), (7) betamethasone 17-(ethyl carbonate)-21-acetate, (8) betamethasone 17-(ethyl carbonate)-21-propionate, (9) betamethasone 17-(ethyl carbonate)-21-butyrate, (10) betamethasone 17-(ethyl carbonate)-21-valerate, (11) betamethasone 17-(ethyl carbonate)-21-cyclopropanecarboxylate and (12) betamethasone 17-(ethyl carbonate)-21-cyclopentylpropionate is obtained in each case.

(b) 3 g of betamethasone 17-(ethyl carbonate) are reacted with methanesulfonyl chloride, and the product is worked up, in the same way as described in Example 2(f). After crystallization from ether, betamethasone 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding betamethasone 17-(ethyl carbonate)-21-p-toluenesulfonate or, respectively, betamethasone 17-(ethyl carbonate)-21-p-chlorobenzenesulfonate is obtained.

(c) The betamethasone diethyl orthocarbonate ($R_f \approx 0.6$) first required for the reaction is prepared according to German Pat. No. 1,668,079 from betamethasone and tetraethyl orthocarbonate. Subsequently, the first-mentioned compound is hydrolyzed to betamethasone 17-(ethyl carbonate) ($R_f$≈0.4) in the same way as described in Example 1(c).

EXAMPLE 36

(a) 1 g of 6α-fluoro-prednisolone 17-(ethyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) 6α-fluoroprednisolone 17-(ethyl carbonate)-21-(methyl carbonate), (2) 6α-fluoroprednisolone 17-(ethyl carbonate)-21-(ethyl carbonate), (3) 6α-fluoroprednisolone 17-(ethyl carbonate)-21-(n-propyl carbonate), (4) 6α-fluoroprednisolone 17-(ethyl carbonate)-21-(n-butyl carbonate), (5) 6α-fluoroprednisolone 17-(ethyl carbonate)-21-(isopropyl carbonate), (6) 6α-fluoroprednisolone 17-(ethyl carbonate)-21-(isobutyl carbonate), (7) 6α-fluoroprednisolone 17-(ethyl carbonate)-21-acetate, (8), 6α-fluoroprednisolone 17-(ethyl carbonate)-21-propionate, (9) 6α-fluoroprednisolone 17-(ethyl carbonate)-21-butyrate, (10) 6α-fluoroprednisolone 17-(ethyl carbonate)-21-valerate, (11) 6α-fluoroprednisolone 17-(ethyl carbonate)-21-cyclopropanecarboxylate and (12) 6α-fluoroprednisolone 17-(ethyl carbonate)-21-cyclopentylpropionate is obtained in each case.

(b) 3 g of 6α-fluoroprednisolone 17-(ethyl carbonate) are reacted with methanesulfonyl chloride, and the product is worked up, in the same was as described in Example 2(f). After crystallization from ether, 6α-fluoro-prednisolone 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α-fluoroprednisolone 17-(ethyl carbonate)-21-p-toluenesulfonate or, respectively, 6α-fluoroprednisolone 17-(ethyl carbonate)-21-p-chlorobenzenesulfonate is obtained.

(c) The 6α-fluoroprednisolone diethyl orthocarbonate ($R_f$≈0.6) first required for the reaction is prepared according to German Pat. No. 1,668,079 from 6α-fluoro-prednisolone and tetraethyl orthocarbonate.

Subsequently, the first-mentioned compound is hydrolyzed to 6α-fluoroprednisolone 17-(ethyl carbonate) ($R_f$≈0.4) in the same way as described in Example 1(c).

EXAMPLE 37

(a) 1 g of 16α- or β-methyl-prednisolone 17-(ethyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) 16α- or β-methylprednisolone 17-(ethyl carbonate)-21-(methyl carbonate), (2) 16α- or β-methylprednisolone 17-(ethyl carbonate)-21-(ethyl carbonate), (3) 16α- or β-methylprednisolone 17-(ethyl carbonate)-21-(n-propyl carbonate), (4) 16α- or β-methylprednisolone 17-(ethyl carbonate)-21-(n-butyl carbonate), (5) 16α- or β-methylprednisolone 17-(ethyl carbonate)-21-(isopropyl carbonate), (6) 16α- or β-methylprednisolone 17-(ethyl carbonate)-21-(isobutyl carbonate), (7) 16α- or β-methylprednisolone 17-(ethyl carbonate)-21-acetate, (8) 16α- or β-methylprednisolone 17-(ethyl carbonate)-21-propionate, (9) 16α- or β-methylprednisolone 17-(ethyl carbonate)-21-butyrate, (10) 16α- or β-methylprednisolone 17-(ethyl carbonate)-21-valerate, (11) 16α- or β-methylprednisolone 17-(ethyl carbonate)-21-cyclopropanecarboxylate or (12) 16α- or β-methylprednisolone 17-(ethyl carbonate)-21-cyclopentylpropionate is obtained in each case.

(b) 3 g of 16α- or β-methylprednisolone 17-(ethyl carbonate) are reacted with methanesulfonyl chloride, and the product is worked up, in the same was as described in Example 2(f). After crystallization from ether, 16α- or β-methylprednisolone 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 16α- or β-methylprednisolone 17-(ethyl carbonate)-21-p-toluenesulfonate or, respectively, 16α- or β-methylprednisolone 17-(ethyl carbonate)-21-p-chlorobenzenesulfonate is obtained.

(c) The 16α- or β-methylprednisolone diethyl orthocarbonate ($R_f$≈0.6) first required for the reaction is prepared according to German Pat. No. 1,668,079 from 16α- or β-methylprednisolone and tetra ethyl orthocarbonate.

Subsequently, the first-mentioned compound is hydrolyzed to 16α- or β-methylprednisolone 17-(ethyl carbonate) ($R_f$≈0.4) in the same way as described in Example 1(c).

EXAMPLE 38

(a) 1 g of 6α,16α- or β-dimethylprednisolone 17-(ethyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) 6α,16α- or β-dimethyl-prednisolone 17-(ethyl carbonate)-21-(methyl carbonate), (2) 6α,16α- or β-dimethyl-prednisolone 17-(ethyl carbonate)-21-(ethyl carbonate), (3) 6α,16α- or β-dimethyl-prednisolone 17-(ethyl carbonate)-21-(n-propyl carbonate), (4) 6α,16α- or β-dimethyl-prednisolone 17-(ethyl carbonate)-21-(n-butyl carbonate), (5) 6α,16α- or β-dimethyl-prednisolone 17-(ethyl carbonate)-21-(isopropyl carbonate), (6) 6α,16α- or β-dimethyl-prednisolone 17-(ethyl carbonate)-21-(isobutyl carbonate), (7) 6α,16α- or β-dimethyl-prednisolone 17-(ethyl carbonate)-21-acetate, (8) 6α,16α- or β-dimethyl-prednisolone 17-(ethyl carbonate)-21-propionate, (9) 6α,16α- or β-dimethyl-prednisolone 17-(ethyl carbonate)-21-butyrate, (10) 6α,16α- or β-dimethyl-prednisolone 17-(ethyl carbonate)-21-valerate, (11) 6α,16α- or β-dimethyl-prednisolone 17-(ethyl carbonate)-21-cyclopropanecarboxylate and (12) 6α,16α- or β-dimethyl-prednisolone 17-(ethyl carbonate)-21-cyclopentylpropionate is obtained in each case.

(b) 3 g of 6α,16α- or β-dimethyl-prednisolone 17-(ethyl carbonate) are reacted with methanesulfonyl chloride, and the product is worked up, in the same way as described in Example 2 (f). After crystallization from ether, 6α,16α- or β-dimethyl-prednisolone 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α,16α- or β-dimethyl-prednisolone 17-(ethyl carbonate)-21-p-toluenesulfonate or, respectively, 6α,16α- or β-dimethyl-prednisolone 17-(ethyl carbonate)-21-p-chlorobenzenesulfonate is obtained.

(c) The 6α,16α- or β-dimethyl-prednisolone diethyl orthocarbonate ($R_f \approx 0.6$) first required for the reaction is prepared according to German Pat. No. 1,668,079 from 6α,16α- or β-dimethyl-prednisolone and tetraethyl orthocarbonate.

Subsequently, the first-mentioned compound is hydrolyzed to 6α,16α- or β-dimethyl-prednisolone 17-(ethyl carbonate) ($R_f \approx 0.4$) in the same way as described in Example 1 (c).

EXAMPLE 39

(a) 1 g of 9α-chloro-16α-methyl-prednisolone 17-(ethyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 9α-chloro-16α-methyl-prednisolone 17-(ethyl carbonate)-21-(methyl carbonate), (2) 9α-chloro-16α-methyl-prednisolone 17-(ethyl carbonate)-21-(ethyl carbonate), (3) 9α-chloro-16α-methyl-prednisolone 17-(ethyl carbonate)-21-(n-propyl carbonate), (4) 9α-chloro-16α-methyl-prednisolone 17-(ethyl carbonate)-21-(n-butyl carbonate), (5) 9α-chloro-16α-methyl-prednisolone 17-(ethyl carbonate)-21-(isopropyl carbonate), (6) 9α-chloro-16α-methyl-prednisolone 17-(ethyl carbonate)-21-isobutyl carbonate), (7) 9α-chloro-16α-methyl-prednisolone 17-(ethyl carbonate)-21-acetate, (8) 9α-chloro-16α-methylprednisolone 17-(ethyl carbonate)-21-propionate, (9) 9α-chloro-16α-methyl-prednisolone 17-(ethyl carbonate)-21-butyrate, (10) 9α-chloro-16α-methyl-prednisolone 17-(ethyl carbonate)-21-valerate, (11) 9α-chloro-16α-methyl-prednisolone 17-(ethyl carbonate)-21-cyclopropanecarboxylate and (12) 9α-chloro-16α-methyl-prednisolone 17-(ethyl carbonate)-21-cyclopentylpropionate is obtained in each case.

(b) 3 g of 9α-chloro-16α-methyl-prednisolone 17-(ethyl carbonate), are reacted with methanesulfonyl chloride, and the product is worked up, in the same way as described in Example 2 (f). After crystallization from ether, 9α-chloro-16α-methyl-prednisolone 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α-chloro-16α-methyl-prednisolone 17-(ethyl carbonate)-21-p-toluenesulfonate or, respectively, 6α-chloro-16α-methyl-prednisolone 17-(ethyl carbonate)-21-p-chlorobenzenesulfonate is obtained.

(c) The 6α-chloro-16α-methyl-prednisolone diethyl orthocarbonate ($R_f \approx 0.6$) first required for the reaction is prepared according to German Pat. No. 1,668,079 from 6α-chloro-16α-methyl-prednisolone and tetraethyl orthocarbonate.

Subsequently, the first-mentioned compound is hydrolyzed to 6α-chloro-16α-methyl-prednisolone 17-(ethyl carbonate) ($R_f \approx 0.4$) in the same way as described in Example 1 (c).

EXAMPLE 40

(a) 1 g of 9α-chloro-prednisolone 17-(ethyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 9α-chloro-prednisolone 17-(ethyl carbonate)-21-(methyl carbonate), (2) 9α-chloro-prednisolone 17-(ethyl carbonate)-21-(ethyl carbonate, (3) 9α-chloro-prednisolone 17-(ethyl carbonate)-21-(n-propyl carbonate), (4) 9α-chloroprednisolone 17-(ethyl carbonate)-21-(n-butyl carbonate), (5) 9α-chloro-prednisolone 17-(ethyl carbonate)-21-(isopropylcarbonate), (6) 9α-chloro-prednisolone 17-(ethyl carbonate)-21-(isobutyl carbonate), (7) 9α-chloro-prednisolone 17-(ethyl carbonate)-21-acetate, (8) 9α-chloro-prednisolone 17-(ethyl carbonate)-21-propionate, (9) 9α-chloro-prednisolone 17-(ethyl carbonate)-21-butyrate, (10) 9α-chloro-prednisolone 17-(ethyl carbonate)-21-valerate, (11) 9α-chloro-prednisolone 17-(ethyl carbonate)-21-cyclopropanecarboxylate and (12) 9α-chloroprednisolone 17-(ethyl carbonate)-21-cyclopentylpropionate is obtained in each case.

(b) 3 g of 9α-chloro-prednisolone 17-(ethyl carbonate) are reacted with methanesulfonyl chloride, and the product is worked up, in the same way as described in Example 2 (f). After crystallization from ether, 9α-chloro-prednisolone 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 9α-chloro-prednisolone 17-(ethyl carbonate)-21-p-toluenesulfonate or, respectively, 9α-chloro-prednisolone 17-(ethyl carbonate)-21-p-chlorobenzenesulfonate is obtained.

(c) The 9α-chloro-prednisolone diethyl orthocarbonate ($R_f \approx 0.6$) first required for the reaction is prepared according to German Pat. No. 1,668,079 from 9α-chloroprednisolone and tetraethyl orthocarbonate.

Subsequently, the first-mentioned compound is hydrolyzed to 9α-chloro-prednisolone 17-(ethyl carbonate) ($R_f \approx 0.4$) in the same way as described in Example 1 (c).

EXAMPLE 41

(a) 1 g of prednisolone 17-(n-propyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.9 ml of butyryl chloride, (8) with 1 ml of valeryl chloride, (9) with 1 ml of cyclopropanecarboxylic acid chloride and (10) with 1.3 ml of cyclopentylpropionyl chloride, instead of with methyl chloroformate, and the product is worked up, in the same way as described in Example 4 (a).

The corresponding (1) prednisolone 17-(n-propyl carbonate)-21-(methyl carbonate), (2) prednisolone 17-(n-propyl carbonate)-21-(ethyl carbonate), (3) prednisolone 17-(n-propyl carbonate)-21-(n-propyl carbonate), (4) prednisolone 17-(n-propyl carbonate)-21-(n-butyl carbonate), (5) prednisolone 17-(n-propyl carbonate)-21-(isopropyl carbonate), (6) prednisolone 17-(n-propyl carbonate)-21-(isobutyl carbonate), (7) prednisolone 17-(n-propyl carbonate)-21-butyrate, (8) prednisolone 17-(n-propyl carbonate)-21-valerate, (9) prednisolone 17-(n-propylcarbonate)-21-cyclopropanecarboxylate and (10) prednisolone 17-(n-propyl carbonate)-21-cyclopentylpropionate is obtained in each case.

(b) 3 g of prednisolone 17-(n-propyl-carbonate) are reacted with methanesulfonyl chloride, and the product is worked up, in the same was as described in Example 2 (f). After crystallization from ether, prednisolone 17-(n-propyl carbonate)-21-methanesulfonate is obtained.

If an equimolar amount of p-toluenesulfonyl chloride or of p-chlorobenzenesulfonyl chloride is employed in place of methanesulfonyl chloride, the corresponding prednisolone 17-(n-propyl carbonate)-21-p-toluenesulfonate or, respectively, prednisolone 17-(n-propyl carbonate)-21-p-chlorobenzenesulfonate is obtained.

(c) The prednisolone di-(n-propyl) orthocarbonate ($R_f \approx 0.6$) first required for the reaction is prepared according to German Pat. No. 1,668,079 from prednisolone and tetra-(n-propyl) orthocarbonate.

Subsequently, the first-mentioned compound is hydrolyzed to prednisolone 17-(n-propyl carbonate) ($R_f \approx 0.4$) in the same way as described in Example 1 (c).

EXAMPLE 42

(a) 1 g of prednisone 17-(n-propyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) prednisone 17-(n-propyl carbonate)-21-(methyl carbonate), (2) prednisone 17-(n-propyl carbonate)-21-(ethyl carbonate), (3) prednisone 17-(n-propyl carbonate)-21-(n-propyl carbonate), (4) prednisone 17-(n-propyl carbonate)-21-(n-butyl carbonate), (5) prednisone 17-(n-propyl carbonate)-21-(isopropyl carbonate), (6) prednisone 17-(n-propyl carbonate)-21-(isobutyl carbonate), (7) prednisone 17-(n-propyl carbonate)-21-acetate, (8) prednisone 17-(n-propyl carbonate)-21-propionate, (9) prednisone 17-(n-propyl carbonate)-21-butyrate, (10-prednisone 17-(n-propyl carbonate)-21-valerate, (11) prednisone 17-(n-propyl carbonate)-21-cyclopropanecarboxylate and (12) prednisone 17-(n-propyl carbonate)-21-cyclopentylpropionate is obtained in each case.

(b) 3 g of prednisone 17-(n-propyl carbonate) are reacted with methanesulfonyl chloride, and the product is worked up, in the same way as described in Example 2 (f). After crystallization from ether, prednisone 17-(n-propyl carbonate)-21-methanesulfonate is obtained.

If an equimolar amount of p-toluenesulfonyl chloride or of p-chlorobenzenesulfonyl chloride is employed in place of methanesulfonyl chloride, the corresponding prednisone 17-(n-propyl carbonate)-21-p-toluenesulfonate or, respectively, prednisone 17-(n-propyl carbonate)-21-p-chlorobenzenesulfonate is obtained.

(c) The prednisone di-(n-propyl) orthocarbonate ($R_f \approx 0.6$), first required for the reaction, is prepared according to German Pat. No. 1,668,079 from prednisone and tetra-(n-propyl) orthocarbonate. Subsequently, the first-mentioned compound is hydrolyzed to prednisone 17-(n-propyl carbonate), ($R_f \approx 0.4$) in the same way as described in Example 1 (c).

EXAMPLE 43

(a) 1 g of cortisone 17-(n-propyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) cortisone 17-(n-propyl carbonate)-21-(methyl carbonate), (2) cortisone 17-(n-propyl carbonate)-21-(ethyl carbonate), (3) cortisone 17-(n-propyl carbonate)-21-(n-propyl carbonate), (4) cortisone 17-(n-propyl carbonate)-21-(n-butyl carbonate), (5) cortisone 17-(n-propyl carbonate)-21-(isopropyl carbonate), (6) cortisone 17-(n-propyl carbonate)-21-(isobutyl carbonate), (7) cortisone 17-(n-propyl carbonate)-21-acetate, (8) cortisone 17-(n-propyl carbonate)-21-propionate, (9) cortisone 17-(n-propyl carbonate)-21-butyrate, (10) cortisone 17-(n-propyl carbonate)-21-valerate, (11) cortisone 17-(n-propyl carbonate)-21-cyclopropanecarboxylate and (12) cortisone 17-(n-propyl carbonate-21-cyclopentylpropionate is obtained in each case.

(b) 3 g of cortisone 17-(n-propyl carbonate) are reacted with methanesulfonyl chloride, and the product is worked up, in the same way as described in Example 2 (f). After crystallization from ether, cortisone 17-(n-propylcarbonate)-21-methanesulfonate is obtained.

If an equimolar amount of p-toluenesulfonyl chloride or of p-chlorobenzenesulfonyl chloride is employed in place of methanesulfonyl chloride, the corresponding cortisone 17-(n-propyl carbonate)-21-p-toluenesulfonate or, respectively, cortisone 17-(n-propyl carbonate)-21-p-chlorobenzenesulfonate is obtained.

(c) The cortisone di-(n-propyl) orthocarbonate ($R_f \approx 0.6$) first required for the reaction is prepared according to German Pat. No. 1,668,079 from cortisone and tetra-(n-propyl) orthocarbonate.

Subsequently, the first-mentioned compound is hydrolyzed to cortisone 17-(n-propyl carbonate) ($R_f \approx 0.4$) in the same way as described in Example 1 (c).

EXAMPLE 44

(a) 1 g of cortisol 17-(n-propyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.9 ml of butyryl chloride, (9) with 1 ml of valeryl chloride, (10) with 1 ml of cyclopropanecarboxylic acid chloride and (11) with 1.3 ml of cyclopentylpropionyl chloride, instead of with methyl chloroformate, and the product is worked up, in the same way as described in Example 4 (a).

The corresponding (1) cortisol 17-(n-propyl carbonate)-21-(methyl carbonate), (2) cortisol 17-(n-propyl carbonate)-21-(ethyl carbonate), (3) cortisol 17-(n-propyl carbonate)-21-(n-propyl carbonate), (4) cortisol 17-(n-propyl carbonate)-21-(n-butyl carbonate, (5) cortisol 17-(n-propyl carbonate)-21-(isopropyl carbonate), (6) cortisol 17-(n-propyl carbonate)-21-(isobutyl carbonate), (7) cortisol 17-(n-propyl carbonate)-21-acetate, (8) cortisol 17-(n-propyl carbonate)-21-butyrate, (9) cortisol 17-(n-propyl carbonate)-21-valerate, (10) cortisol 17-(n-propyl carbonate)-21-cyclopropanecarboxylate and (11) cortisol 17-(n-propyl carbonate)-21-cyclopentylpropionate is obtained in each case.

(b) 3 g of cortisol 17-(n-propyl carbonate) are reacted with methanesulfonyl chloride, and the product is worked up, in the same way as described in Example 2 (f). After crystallization from ether, cortisol 17-(n-propyl carbonate)-21-methanesulfonate is obtained.

If an equimolar amount of p-toluenesulfonyl chloride or of p-chlorobenzenesulfonyl chloride is employed in place of methanesulfonyl chloride, the corresponding cortisol 17-(n-propyl carbonate)-21-p-toluenesulfonate or, respectively, cortisol 17-(n-propyl carbonate)-21-p-chlorobenzenesulfonate is obtained.

(c) The cortisol di-(n-propyl) orthocarbonate ($R_f \approx 0.6$) first required for the reaction is prepared according to German Pat. No. 1,668,079 from cortisol and tetra-(n-propyl) orthocarbonate. Subsequently, the first-mentioned compound is hydrolyzed to cortisol 17-(n-propyl carbonate), ($R_f \approx 0.4$) in the same way as described in Example 1 (c).

EXAMPLE 45

(a) 1 g of beclomethasone 17-(n-propyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) 1.3 ml of cyclopentylpropionyl chloride, instead of with methyl chloroformate, and the product is worked up, in the same way as described in Example 4 (a).

The corresponding (1) beclomethasone 17-(n-propyl carbonate)-21-(methyl carbonate), (2) beclomethasone 17-(n-propyl carbonate)-21-(ethyl carbonate), (3) beclomethasone 17-(n-propyl carbonate)-21-(n-propyl carbonate), (4) beclomethasone 17-(n-propyl carbonate)-21-(n-butyl carbonate), (5) beclomethasone 17-(n-propyl carbonate)-21-(isopropyl carbonate), (6) beclomethasone 17-(n-propyl carbonate)-21-(isobutyl carbonate), (7) beclomethasone 17-(n-propyl carbonate)-21-acetate, (8) beclomethasone 17-(n-propyl carbonate)-21-propionate, (9) beclomethasone 17-(n-propyl carbonate)-21-butyrate, (10) beclomethasone 17-(n-propyl carbonate)-21-valerate, (11) beclomethasone 17-(n-propyl carbonate)-21-cyclopropanecarboxylate and (12) beclomethasone 17-(n-propyl carbonate)-21-cyclopentylpropionate is obtained in each case.

(b) 3 g of beclomethasone 17-(n-propyl carbonate) is reacted with methanesulfonyl chloride, and the product is worked up, in the same way as described in Example 2 (f). After crystallization from ether, beclomethasone 17-(n-propyl carbonate)-21-methanesulfonate is obtained.

If an equimolar amount of p-toluenesulfonyl chloride or of p-chlorobenzenesulfonyl chloride is employed in place of methanesulfonyl chloride, the corresponding beclomethasone 17-(n-propyl carbonate)-21-p-toluenesulfonate or, respectively, beclomethasone 17-(n-propyl carbonate)-21-p-chlorobenzenesulfonate is obtained.

(c) The beclomethasone di-(n-propyl) orthocarbonate ($R_f \approx 0.6$) first required for the reaction is prepared according to German Pat. No. 1,668,079 from beclomethasone and tetra-(n-propyl) orthocarbonate.

Subsequently, the first-mentioned compound is hydrolyzed to beclomethasone 17-(n-propyl carbonate) ($R_f \approx 0.4$) in the same way as described in Example 1 (c).

EXAMPLE 46

(a) 1 g of 6α-fluorodexamethasone 17-(n-propyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 6α-fluorodexamethasone 17-(n-propyl carbonate)-21-(methyl carbonate), (2) 6α-fluorodexamethasone 17-(n-propyl carbonate)-21-(ethyl carbonate), (3) 6α-fluorodexamethasone 17-(n-propyl carbonate)-21-n-propyl carbonate), (4) 6α-fluorodexamethasone 17-(n-propyl carbonate)-21-(n-butyl carbonate), (5) 6α-fluorodexamethasone 17-(n-propyl carbonate)-21-(isopropyl carbonate), (6) 6α-fluorodexamethasone 17-(n-propyl carbonate)-21-(isobutyl carbonate), (7) 6α-fluorodexamethasone 17-(n-propyl carbonate)-21-acetate, (8) 6α-fluorodexamethasone 17-(n-propyl carbonate)-21-propionate, (9) 6α-fluorodexamethasone 17-(n-propyl carbonate)-21-butyrate, (10) 6α-fluorodexamethasone 17-(n-propyl carbonate)-21-valerate, (11) 6α-fluorodexamethasone 17-(n-propyl carbonate)-21-cyclopropanecarboxylate and (12) 6α-fluorodexamethasone 17-(n-propyl carbonate)-21-cyclopentylpropionate is obtained is each case.

(b) 3 g of 6α-fluorodexamethasone 17-(n-propyl carbonate) are reacted with methanesulfonyl chloride, and the product is worked up, in the same way as described in Example 2 (f). After crystallization from ether, 6α-fluorodexamethasone 17-(n-propyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α-fluorodexamethasone 17-(n-propyl carbonate)-21-p-toluenesulfonate or, respectively, 6α-fluorodexamethasone 17-(n-propyl carbonate)-21-p-chlorobenzenesulfonate is obtained.

(c) The 6α-fluorodexamethasone di-(n-propyl) orthocarbonate ($R_f \approx 0.6$) first required for the reaction is prepared according to German Pat. No. 1,668,079 from 6α-fluorodexamethasone and tetra-(n-propyl) orthocarbonate.

Subsequently, the first-mentioned compound is hydrolyzed to 6α-fluorodexamethasone 17-(n-propyl carbonate) ($R_f \geq 0.4$) in the same way as described in Example 1 (c).

EXAMPLE 47

(a) 1 g of betamethasone 17-(n-propyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) betamethasone 17-(n-propyl carbonate)-21-(methyl carbonate), (2) betamethasone 17-(n-propyl carbonate)-21-(ethyl carbonate), (3) betamethasone 17-(n-propyl carbonate)-21-(n-propyl carbonate), (4) betamethasone 17-(n-propyl carbonate)-21-(n-butyl carbonate), (5) betamethasone 17-(n-propyl carbonate)-21-(isopropyl carbonate), (6) betamethasone 17-(n-propyl carbonate)-21-(isobutyl carbonate), (7) betamethasone 17-(n-propyl carbonate)-21-acetate, (8) betamethasone 17-(n-propyl carbonate)-21-propionate, (9) betamethasone 17-(n-propyl carbonate)-21-butyrate, (10) betamethasone 17-(n-propyl carbonate)-21-valerate, (11) betamethasone 17-(n-propyl carbonate)-21-cyclopropanecarboxylate and (12) betamethasone 17-(n-propyl carbonate)-21-cyclopentylpropionate is obtained in each case.

(b) 3 g of betamethasone 17-(n-propyl carbonate) are reacted with methanesulfonyl chloride, and the product is worked up, in the same way as described in Example 2 (f). After crystallization from ether, betamethasone 17-(n-propyl carbonate)-21-methanesulfonate is obtained.

If an equimolar amount of p-toluenesulfonyl chloride or of p-chlorobenzenesulfonyl chloride is employed in place of methanesulfonyl chloride, the corresponding betamethasone 17-(n-propyl carbonate)-21-p-toluenesulfonate or, respectively, betamethasone 17-(n-propyl carbonate)-21-p-chlorobenzenesulfonate is obtained.

(c) The betamethasone di-(n-propyl) orthocarbonate ($R_f \approx 0.6$) first required for the reaction is prepared according to German Pat. No. 1,668,079 from betamethasone and tetra (n-propyl) orthocarbonate.

Subsequently, the first-mentioned compound is hydrolyzed to betamethasone 17-(n-propyl carbonate) ($R_f \approx 0.4$) in the same way as described in Example 1 (c).

EXAMPLE 48

(a) 1 g of 6α-fluoro-prednisolone 17-(n-propyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 6α-fluoro-prednisolone 17-(n-propyl carbonate)-21-(methyl carbonate), (2) 6α-fluoro-prednisolone 17-(n-propyl carbonate)-21-(ethyl carbonate), (3) 6α-fluoro-prednisolone 17-(n-propyl carbonate)-21-(n-propyl carbonate), (4) 6α-fluoro-prednisolone 17-(n-propyl carbonate)-21-(n-butyl carbonate), (5) 6α-fluoro-prednisolone 17-(n-propyl carbonate)-21-(isopropyl carbonate), (6) 6α-fluoro-prednisolone 17-(n-propyl carbonate)-21-(isobutyl carbonate), (7) 6α-fluoroprednisolone 17-(n-propyl carbonate)-21-acetate, (8) 6α-fluoroprednisolone 17-(n-propyl carbonate)-21-propionate, (9) 6α-fluoro-prednisolone 17-(n-propyl carbonate)-21-butyrate, (10) 6α-fluoro-prednisolone 17-(n-propyl carbonate)-21-valerate, (11) 6α-fluoro-prednisolone 17-(n-propyl carbonate)-21-cyclopropanecarboxylate and (12) 6α-fluoro-prednisolone 17-(n-propyl carbonate)-21-cyclopentylpropionate is obtained in each case.

(b) 3 g of 6α-fluoro-prednisolone 17-(n-propyl carbonate) are reacted with methanesulfonyl chloride, and the product is worked up, in the same way as described in Example 2(f). After crystallization from ether, 6α-fluoro-prednisolone 17-(n-propyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α-fluoro-prednisolone 17-(n-propyl carbonate)-21-p-toluenesulfonate or, respectively, 6α-fluoro-prednisolone 17-(n-propyl carbonate)-21-p-chlorobenzenesulfonate is obtained.

(c) The 6α-fluoro-prednisolone di-(n-propyl) orthocarbonate ($R_f \approx 0.6$) first required for the reaction is prepared according to German Pat. No. 1,668,079 from 6α-fluoro-prednisolone and tetra-(n-propyl) orthocarbonate.

Subsequently, the first-mentioned compound is hydrolyzed to 6α-fluoro-prednisolone 17-(n-propyl car-

EXAMPLE 49

(a) 1 g of 16α- or β-methyl-prednisolone 17-(n-propyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) 16α- or β-methyl-prednisolone 17-(n-propyl carbonate)-21-(methyl carbonate), (2) 16α- or β-methyl-prednisolone 17-(n-propyl carbonate)-21-(ethyl carbonate), (3) 16α- or β-methyl-prednisolone 17-(n-propyl carbonate)-21-(n-propyl carbonate), (4) 16α- or β-methyl-prednisolone 17-(n-propyl carbonate)-21-(n-butyl carbonate), (5) 16α- or β-methyl-prednisolone 17-(n-propyl carbonate)-21-(isopropyl carbonate), (6) 16α- or β-methyl-prednisolone 17-(n-propyl carbonate)-21-(isobutyl carbonate), (7) 16α- or β-methyl-prednisolone 17-(n-propyl carbonate)-21-acetate, (8) 16α- or β-methyl-prednisolone 17-(n-propyl carbonate)-21-propionate, (9) 16α- or β-methyl-prednisolone 17-(n-propyl carbonate)-21-butyrate, 16α- or β-methyl-prednisolone 17-(n-propyl carbonate)-21-valereate, (11) 16α- or β-methyl-prednisolone 17-(n-propyl carbonate)-21-cyclopropanecarboxylate and (12) 16α- or β-methyl-prednisolone 17-(n-propyl carbonate)-21-cyclopentylpropionate is obtained in each case.

(b) 3 g of 16α- or β-methyl-prednisolone 17-(n-propyl carbonate) are reacted with methanesulfonyl chloride, and the product is worked up, in the same way as described in Example 2(f). After crystallization from ether, 16α- or β-methyl-prednisolone 17-(n-propyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 16α- or β-methyl-prednisolone 17-(n-propyl carbonate)-21-p-toluenesulfonate or, respectively, 16α- or β-methyl-prednisolone 17-(n-propyl carbonate)-21-p-chlorobenzenesulfonate is obtained.

(c) The 16α- or β-methyl-prednisolone di-(n-propyl) ortho-carbonate ($R_f \approx 0.6$) first required for the reaction is prepared according to German Pat. No. 1,668,079 from 16α- or β-methyl-prednisolone and tetra-(n-propyl) orthocarbonate.

Subsequently, the first-mentioned compound is hydrolyzed to 16α- or β-methyl-prednisolone 17-(n-propyl carbonate) ($R_f \approx 0.4$) in the same way as described in Example 1(c).

EXAMPLE 50

(a) 1 g of 6α,16α- or β-dimethyl-prednisolone 17-(n-propyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) 6α,16α- or β-dimethyl-prednisolone 17-(n-propyl carbonate)-21-(methyl carbonate), (2) 6α,16α- or β-dimethyl-prednisolone 17-(n-propyl carbonate)-21-(ethyl carbonate), (3) 6α,16α- or β-dimethyl-prednisolone 17-(n-propyl carbonate)-21-(n-propyl carbonate), (4) 6α,16α- or β-dimethyl-prednisolone 17-(n-propyl carbonate)-21-(n-butyl carbonate), (5) 6α,16α- or β-dimethyl-prednisolone 17-(n-propyl carbonate)-21-(isopropyl carbonate), (6) 6α,16α- or β-dimethyl-prednisolone 17-(n-propyl carbonate)-21-(isobutyl carbonate), (7) 6α,16α- or β-dimethyl-prednisolone 17-(n-propyl carbonate)-21-acetate, (8) 6α,16α- or β-dimethyl-prednisolone 17-(n-propyl carbonate)-21-propionate, (9) 6α,16α- or β-dimethyl-prednisolone 17-(n-propyl carbonate)-21-butyrate, (10) 6α,16α- or β-dimethyl-prednisolone 17-(n-propyl carbonate)-21-valerate, (11) 6α,16α- or β-dimethyl-prednisolone 17-(n-propyl carbonate)-21-cyclopropanecarboxylate and (12) 6α,16α- or β-dimethyl-prednisolone 17-(n-propyl carbonate)-21-cyclopentylpropionate is obtained in each case.

(b) 3 g of 6α,16α- or β-dimethyl-prednisolone 17-(n-propyl carbonate) are reacted with methanesulfonyl chloride, and the product is worked up, in the same way as described in Example 2(f). After crystallization from ether, 6α,16α- or β-dimethyl-prednisolone 17-(n-propyl carbonate)-21-p-methanesulfonate is obtained.

If an equimolar amount of p-toluenesulfonyl chloride or of p-chlorobenzenesulfonyl chloride is employed in place of methanesulfonyl chloride, the corresponding 6α,16α- or β-dimethyl-prednisolone 17-(n-propyl carbonate)-21-p-toluenesulfonate or, respectively, 6α,16α- or β-dimethyl-prednisolone 17-(n-propyl carbonate)-21-p-chlorobenzenesulfonate is obtained.

(c) The 6α,16α- or β-dimethyl-prednisolone di-(n-propyl) orthocarbonate ($R_f \approx 0.6$) first required for the reaction is prepared according to German Pat. No. 1,668,079 from 6α,16α- or β-dimethyl-prednisolone and tetra-(n-propyl) orthocarbonate.

Subsequently, the first-mentioned compound is hydrolyzed to 6α,16α- or β-dimethyl-prednisolone 17-(n-propyl carbonate) ($R_f \approx 0.4$) in the same way as described in Example 1(c).

EXAMPLE 51

(a) 1 g of 9α-chloro-16α-methyl-prednisolone 17-(n-propyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1,3 ml of cyclopentylpropionyl chloride, instead of with methyl chloroformate, and the product is worked up, in the same way as described in Example 4(a).

The corresponding (1) 9α-chloro-16α-methyl-prednisolone 17-(n-propyl carbonate)-21-(methyl carbonate), (2) 9α-chloro-16α-methyl-prednisolone 17-(n-propyl carbonate)-21-(ethyl carbonate), (3) 9α-chloro-16α-methyl-prednisolone 17-(n-propyl) carbonate)-21-(n-propyl carbonate), (4) 9α-chloro-16α-methyl-prednisolone 17-(n-propyl carbonate)-21-(n-butyl carbonate), (5) 9α-chloro-16α-methyl-prednisolone 17-(n-propyl carbonate)-21-(isopropyl carbonate), (6) 9α-chloro-16α-methyl-prednisolone 17-(n-propyl carbonate)-21-(isobutyl carbonate), (7) 9α-chloro-16α-methyl-prednisolone 17-(n-propyl carbonate)-21-acetate, (8) 9α-chloro-16α-methyl-prednisolone 17-(n-propyl carbonate)-21-propionate, (9) 9α-chloro-16α-methyl-prednisolone 17-(n-propyl carbonate)-21-butyrate, (10) 9α-chloro-16α-methyl-prednisolone 17-(n-propyl carbonate)-21-valerate, (11) 9α-chloro-16α-methyl-prednisolone 17-(n-propyl carbonate)-21-cyclopropanecarboxylate and (12) 9α-chloro-16α-methyl-prednisolone 17-(n-propyl carbonate)-21-cyclopentylpropionate is obtained in each case.

(b) 3 g of 9α-chloro-16α-methyl-prednisolone 17-(n-propyl carbonate) are reacted with methanesulfonyl chloride, and the product is worked up, in the same way as described in Example 2(f). After crystallization from ether, 9α-chloro-16α-methyl-prednisolone 17-(n-propyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 9α-chloro-16α-methyl-prednisolone 17-(n-propyl carbonate)-21-p-toluenesulfonate or, respectively, 9α-chloro-16α-methyl-prednisolone 17-(n-propyl carbonate)-21-p-chlorobenzenesulfonate is obtained.

(c) The 9α-chloro-16α-methyl-prednisolone di-(n-propyl) orthocarbonate ($R_f \approx 0.6$) first required for the reaction is prepared according to German Pat. No. 1,668,079 from 9α-chloro-16α-methyl-prednisolone and tetra-(n-propyl) orthocarbonate.

Subsequently, the first-mentioned compound is hydrolyzed to 9α-chloro-16α-methyl-prednisolone 17-(n-propyl carbonate) ($R_f \approx 0.4$) in the same way as described in Example 1(c).

EXAMPLE 52

(a) 1 g of 9α-chloro-prednisolone 17-(n-propyl carbonate) is reacted (1) with 0.8 ml of methyl chloformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecaboxylic acid chloride and (12) with 1.3 ml of cyclopentylpropionyl chloride, instead of with methyl chloroformate, and the product is worked up, in the same way as described in Example 4(a).

The corresponding (1) 9α-chloro-prednisolone 17-(n-propyl carbonate)-21-(methyl carbonate), (2) 9α-chloro-prednisolone 17-(n-propyl carbonate)-21-(ethyl carbonate), (3) 9α-chloro-prednisolone 17-(n-propyl carbonate)-21-(n-propyl carbonate), (4) 9α-chloro-prednisolone 17-(n-propyl carbonate)-21-(n-butyl carbonate), (5) 9α-chloro-prednisolone 17-(n-propyl carbonate)-21-(isopropyl carbonate), (6) 9α-chloro-prednisolone 17-(n-propyl carbonate)-21-(isobutyl carbonate), (7) 9α-chloro-prednisolone 17-(n-propyl carbonate)-21-acetate, (8) 9α-chloro-prednisolone 17-(n-propyl carbonate)-21-propionate, (9) 9α-chloro-prednisolone 17-(n-propyl carbonate)-21-butyrate, (10) 9α-chloro-prednisolone 17-(n-propyl carbonate)-21-valerate, (11) 9α-chloro-prednisolone 17-(n-propyl carbonate)-21-cyclopropanecarboxylate and (12) 9α-chloro-prednisolone 17-(n-propyl carbonate)-21-cyclopentylpropionate is obtained in each case.

(b) 3 g of 9α-chloro -prednisolone 17-(n-propyl carbonate) are reacted with methanesulfonyl chloride, and the product is worked up, in the same way as described in Example 2(f). After crystallization from ether, 9α-chloro-prednisolone 17-(n-propyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 9α-chloro-prednisolone 17-(n-propyl carbonate)-21-p-toluenesulfonate or, respectively, 9α-chloro-prednisolone 17-(n-propyl carbonate)-21-p-chlorobenzenesulfonate is obtained.

(c) The 9α-chloro-prednisolone di-(n-propyl) orthocarbonate ($R_f \approx 0.6$) first required for the reaction is prepared according to German Pat. No. 1,668,079 from 9α-chloro-prednisolone and tetra-(n-propyl) orthocarbonate.

Subsequently, the first-mentioned compound is hydrolyzed to 9α-chloro-prednisolone 17-(n-propyl carbonate) $R_f \approx 0.4$) in the same way as described in Example 1(c).

EXAMPLE 53

(a) 1 g of prednisolone 17-(n-butyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) prednisolone 17-(n-butyl carbonate)-21-(methyl carbonate), (2) prednisolone 17-(n-butyl carbonate)-21-(ethyl carbonate), (3) prednisolone 17-(n-butyl carbonate)-21-(n-propyl carbonate), (4) prednisolone 17-(n-butyl carbonate)-21-(n-butyl carbonate), (5) prednisolone 17-(n-butyl carbonate)-21-(isopropyl carbonate), (6) prednisolone 17-(n-butyl carbonate)-21-(isobutyl carbonate), (7) prednisolone 17-(n-butyl carbonate)-21-acetate, (8) prednisolone 17-(n-butyl carbonate)-21-propionate, (9) prednisolone 17-(n-butyl carbonate)-21-butyrate, (10) prednisolone 17-(n-butyl carbonate)-21-valerate, (11) prednisolone 17-(n-butyl carbonate)-21-cyclopropanecarboxylate and (12) prednisolone 17-(n-butyl carbonate)-21-cyclopentylpropionate is obtained in each case.

(b) 3 g of prednisolone 17-(n-butyl carbonate) are reacted with methanesulfonyl chloride, and the product is worked up, in the same way as described in Example 2(f). After crystallization from ether, prednisolone 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding prednisolone 17-(n-butyl carbonate)-21-p-toluenesulfonate or, respectively, prednisolone 17-(n-butyl carbonate)-21-p-chlorobenzenesulfonate is obtained.

(c) The prednisolone di-(n-butyl) orthocarbonate ($R_f \approx 0.6$), first required for the reaction is prepared according to German Pat. No. 1,668,079 from prednisolone and tetra-(n-butyl) orthocarbonate. Subsequently, the first-mentioned compound is hydrolyzed to prednisolone 17-(n-butyl carbonate) ($R_f \approx 0.4$) in the same way as described in Example 1(c).

EXAMPLE 54

(a) 1 g of prednisone 17-(n-butyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of propionyl chloride, (9) ml of butyryl chloride, (10) with 1 ml of valeryl chloride, (11) with 1 ml of cyclopropanecarboxylic acid chloride (12) with 1.3 ml of cyclopentylpropionyl chloride, instead of with methyl chloroformate, and the product is worked up, in the same way as described in Example 4(a).

The corresponding (1) prednisone 17-(n-butyl carbonate)-21-(methyl carbonate), (2) prednisone 17-(n-butyl carbonate)-21-(ethyl carbonate), (3) prednisone 17-(n-butyl carbonate)-21-(n-propyl carbonate), (4) prednisone 17-(n-butyl carbonate)-21-(n-butyl carbonate), (5) prednisone 17-(n-butyl carbonate)-21-(isopropyl carbonate), (6) prednisone 17-(n-butyl carbonate)-21-acetate, (8) prednisone 17-(n-butyl carbonate)-21-propionate, (9) prednisone 17-(n-butyl carbonate)-21-butyrate, (10) prednisone 17-(n-butyl carbonate)-21-valerate, (11) prednisone 17-(n-butyl carbonate)-21-cyclopropanecarboxylate and (12) prednisone 17-(n-butyl carbonate)-21-cyclopentylpropionate is obtained in each case.

(b) 3 g of prednisone 17-(n-butyl carbonate) are reacted with methanesulfonyl chloride, and the product is worked up, in the same way as described in Example 2(f). After crystallization from ether, prednisone 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding prednisone 17-(n-butyl carbonate)-21-p-toluenesulfonate or, respectively, prednisone 17-(n-butyl carbonate)-21-p-chlorobenzenesulfonate is obtained.

(c) The prednisone di-(n-butyl) orthocarbonate ($R_f \approx 0.6$) first required for the reaction, is prepared according to German Pat. No. 1,668,079 from prednisone and tetra-(n-butyl) ortho-carbonate. Subsequently, the first-mentioned compound is hydrolyzed to prednisone 17-(n-butyl carbonate) ($R_f = 0.4$) in the same way as described in Example 1(c).

EXAMPLE 55

(a) 1 g of cortisone 17-(n-butyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) cortisone 17-(n-butyl carbonate)-21-(methyl carbonate, (2) cortisone 17-(n-butyl carbonate)-21-(ethyl carbonate), (3) cortisone 17-(n-butyl carbonate)-21-(n-propyl carbonate, (4) cortisone 17-(n-butyl carbonate)-21-(n-butyl carbonate), (5) cortisone 17-(n-butyl carbonate)-21-(isopropyl carbonate), (6) cortisone 17-(n-butyl carbonate)-21-(isobutyl carbonate), (7) cortisone 17-(n-butyl carbonate)-21-acetate, (8) cortisone 17-(n-butyl carbonate)-21-propionate, (9) cortisone 17-(n-butyl carbonate)-21-butyrate, (10) cortisone 17-(n-butyl carbonate)-21-valerate, (11) cortisone 17-(n-butyl carbonate)-21-cyclopropanecarboxylate and (12) cortisone 17-(n-butyl carbonate)-21-cyclopentylpropionate is obtained in each case.

(b) 3 g of cortisone 17-(n-butyl carbonate) are reacted with methanesulfonyl chloride, and the product is worked up, in the same way as described in Example 2(f). After crystallization from ether, cortisone 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding cortisone 17-(n-butyl carbonate)-21-p-toluenesulfonate or, respectively, cortisone 17-(n-butyl carbonate)-21-p-chlorobenzenesulfonate is obtained.

(c) The cortisone di-(n-butyl) orthocarbonate ($R_f = 0.6$) first required for the reaction, is prepared according to German Pat. No. 1,668,079 from cortisone and tetra-(n-butyl) orthocarbonate.

Subsequently, the first-mentioned compound is hydrolyzed to cortisone 17-(n-butyl carbonate) ($R_f = 0.4$) in the same way as described in Example 1(c).

EXAMPLE 56

(a) 1 g of cortisol 17-(n-butyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) cortisol 17-(n-butyl carbonate)-21-(methyl carbonate), (2) cortisol 17-(n-butyl carbonate)-21-(ethyl carbonate, (3) cortisol 17-(n-butyl carbonate)-21-(n-propyl carbonate), (4) cortisol 17-(n-butyl carbonate)-21-(n-butyl carbonate), (5) cortisol 17-(n-butyl carbonate)-21-(isopropyl carbonate), (6) cortisol 17-(n-butyl carbonate)-21-(isobutyl carbonate), (7) cortisol 17-(n-butyl carbonate)-21-acetate, (8) cortisol 17-(n-butyl carbonate)-21-propionate, (9) cortisol 17-(n-butyl carbonate)-21-butyrate, (10) cortisol 17-(n-butyl carbonate)-21-valerate, (11) cortisol 17-(n-butyl carbonate)-21-cyclopropanecarboxylate and (12) cortisol 17-(n-butyl carbonate)-21-cyclopentylpropionate is obtained in each case.

(b) 3 g of cortisol 17-(n-butyl carbonate) are reacted with methanesulfonyl chloride, and the product is worked up, in the same way as described in Example 2(f). After crystallization from ether, cortisol 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding cortisol 17-(n-butyl carbonate)-21-p-toluenesulfonate or, respectively, cortisol 17-(n-butyl carbonate)-21-p-chlorobenzenesulfonate is obtained.

(c) The cortisol di-(n-butyl) orthocarbonate ($R_f=0.6$) first required for the reaction, is prepared according to German Pat. No. 1,668,079 from cortisol and tetra-(n-butyl) orthocarbonate. Subsequently, the first-mentioned compound is hydrolyzed to cortisol 17-(n-butyl carbonate) ($R_f=0.4$) in the same way as described in Example 1(c).

EXAMPLE 57

(a) 1 g of beclomethasone 17-(n-butyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1º beclomethasone 17-(n-butyl carbonate)-21-(methyl carbonate), (2º beclomethasone 17-(n-butyl carbonate)-21-(ethyl carbonate), (3) beclomethasone 17-(n-butyl carbonate)-21-(n-propyl carbonate), 4) beclomethasone 17-(n-butyl carbonate)-21-(n-butyl carbonate), (5) beclomethasone 17-(n-butyl carbonate)-21-(isopropyl carbonate), (6) beclomethasone 17-(n-butyl carbonate)-21-(isobutyl carbonate), (7) beclomethasone 17-(n-butyl carbonate)-21-acetate, (8) beclomethasone 17-(n-butyl carbonate)-21-propionate, (9) beclomethasone 17-(n-butyl carbonate)-21-butyrate, (10) beclomethasone 17-(n-butyl carbonate)-21-valerate, (11) beclomethasone 17-(n-butyl carbonate)-21-cyclopropanecarboxylate and (12) beclomethasone 17-(n-butyl carbonate)-cyclopentylpropionate is obtained in each case.

(b) 3 g of beclomethasone 17-(n-butyl carbonate) are reacted with methanesulfonyl chloride, and the product is worked up, in the same way as described in Example 2(f). After crystallization from ether, beclomethasone 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding beclomethasone 17-(n-butyl carbonate)-21-p-toluenesulfonate or, respectively, beclomethasone 17-(n-butyl carbonate)-21-p-chlorobenzenesulfonate is obtained.

(c) The beclomethasone di-(n-butyl) orthocarbonate ($R_f=0.6$) first required for the reaction, is prepared according to German Pat. No. 1,668,079 from beclomethasone and tetra-(n-butyl) orthocarbonate.

Subsequently, the first-mentioned compound is hydrolyzed to beclomethasone 17-(n-butyl carbonate) ($R_f=0.4$) in the same way as described in Example 1(c).

EXAMPLE 58

(a) 1 g of 6α-fluorodexamethasone 17-(n-butyl carbonate) are reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) 6α-fluorodexamethasone 17-(n-butyl carbonate)-21-(methyl carbonate), (2) 6α-fluorodexamethasone 17-(n-butyl carbonate)-21-(ethyl carbonate), (3) 6α-fluorodexamethasone 17-(n-butyl carbonate)-21-(n-propyl carbonate), (4) 6α-fluorodexamethasone 17-(n-butyl carbonate)-21-(n-butyl carbonate), (5) 6α-fluorodexamethasone 17-(n-butyl carbonate)-21-isopropyl carbonate), (6) 6α-fluorodexamethasone 17-(n-butyl carbonate)-21-(isobutyl carbonate), (7) 6α-fluorodexamethasone 17-(n-butyl carbonate)-21-acetate, (8) 6α-fluorodexamethasone 17-(n-butyl carbonate)-21-propionate, (9) 6α-fluorodexamethasone 17-(n-butyl carbonate)-21-butyrate, (10) 6α-fluorodexamethasone 17-(n-butyl carbonate)-21-valerate, (11) 6α-fluorodexamethasone 17-(n-butyl carbonate)-21-cyclopropanecarboxylate and (12) 6α-fluorodexamethasone 17-(n-butyl carbonate)-21-cyclopentylpropionate is obtained in each case.

(b) 3 g of 6α-fluorodexamethasone 17-(n-butyl carbonate) are reacted with methanesulfonyl chloride, and the product is worked up, in the same way as described in Example 2(f). After crystallization from ether, 6α-fluorodexamethasone 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α-fluorodexamethasone 17-(n-butyl carbonate)-21-p-toluenesulfonate or, respectively, 6α-fluorodexamethasone 17-(n-butyl carbonate)-21-p-chlorobenzenesulfonate is obtained.

(c) The 6α-fluorodexamethasone di-(n-butyl) orthocarbonate ($R_f=0.6$) first required for the reaction, is prepared according to German Pat. No. 1,668,079 from 6α-fluorodexamethasone and tetra-(n-butyl) orthocarbonate.

Subsequently, the first-mentioned compound is hydrolyzed to 6α-fluorodexamethasone 17-(n-butyl carbonate) ($R_f=0.4$) in the same way as described in Example 1(c).

EXAMPLE 59

(a) 1 g of betamethasone 17-(n-butyl carbonate) are reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) betamethasone 17-(b-butyl carbonate)-21-(methyl carbonate), (2) betamethasone 17-(n-butyl carbonate)-21-(ethyl carbonate), (3) betamethasone 17-(n-butyl carbonate)-21-(n-propyl carbonate), (4) betamethasone 17-(n-butyl carbonate)-21-(n-butyl carbonate), (5) betamethasone 17-(n-butyl carbonate)-21-(isopropyl carbonate), (6) betamethasone 17-(n-butyl carbonate)-21-(isobutyl carbonate), (7) betamethasone 17-(n-butyl carbonate)-21-acetate, (8) betamethasone 17-(n-butyl carbonate)-21-propionate, (9) betamethasone 17-(n-butyl carbonate)-21-butyrate, (10) betamethasone 17-(n-butyl carbonate)-21-valerate, (11) betamethasone 17-(n-butyl carbonate)-21-cyclopropanecarboxylate and (12) betamethasone 17-(n-butyl carbonate)-21-cyclopentylpropionate is obtained in each case.

(b) 3 g of betamethasone 17-(n-butyl carbonate) are reacted with methanesulfonyl chloride, and the product is worked up, in the same way as described in Example 2(f). After crystallization from ether, betamethasone 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding betamethasone 17-(n-butyl carbonate)-21-p-toluenesulfonate or, respectively, betamethasone 17-(n-butyl carbonate)-21-p-chlorobenzenesulfonate is obtained.

(c) The betamethasone di-(n-butyl) orthocarbonate ($R_f=0.6$) first required for the reaction, is prepared according to German Pat. No. 1,668,079 from betamethasone and tetra-(n-butyl) orthocarbonate.

Subsequently, the first-mentioned compound is hydrolyzed to betamethasone 17-(n-butyl carbonate), ($R_f=0.4$) in the same way as described in Example 1(c).

EXAMPLE 60

(a) 1 g of (6α-fluoroprednisolone 17-(n-butyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) 6α-fluoroprednisolone 17-(n-butyl carbonate)-21-(methyl carbonate), (2) 6α-fluoroprednisolone 17-(n-butyl carbonate)-21-(ethyl carbonate), (3) 6α-fluoroprednisolone 17-(n-butyl carbonate)-21-(n-propyl carbonate), (4) 6α-fluoroprednisolone 17-(n-butyl carbonate)-21-(n-butyl carbonate), (5) 6α-fluoroprednisolone 17-(n-butyl carbonate)-21-(isopropyl carbonate), (6) 6α-fluoroprednisolone 17-(n-butyl carbonate)-21-(isobutyl carbonate), (7) 6α-fluoroprednisolone 17-(n-butyl carbonate)-21-acetate, (8) 6α-fluoroprednisolone 17-(n-butyl carbonate)-21-propionate, (9) 6α-fluoroprednisolone 17-(n-butyl carbonate)-21-butyrate, (10) 6α-fluoroprednisolone 17-(n-butyl carbonate)-21-valerate, (11) 6α-fluoroprednisolone 17-(n-butyl carbonate)-21-cyclopropanecarboxylate and (12) 6α-fluoroprednisolone 17-(n-butyl carbonate)-21-cyclopentylpropionate is obtained in each case.

(b) 3 g of 6α-fluoroprednisolone 17-(n-butyl carbonate) are reacted with methanesulfonyl chloride, and the product is worked up, in the same way as described in Example 2(f). After crystallization from ether, 6α-fluoroprednisolone 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α-fluoroprednisolone 17-(n-butyl carbonate)-21-p-toluenesulfonate or, respectively, 6α-fluoroprednisolone 17-(n-butyl carbonate)-21-p-chlorobenzenesulfonate is obtained.

(c) The 6α-fluoroprednisolone di-(n-butyl) orthocarbonate ($R_f=0.6$) first required for the reaction, is prepared according to German Pat. No. 1,668,079 from 6α-fluoroprednisolone and tetra-(n-butyl) orthocarbonate.

Subsequently, the first-mentioned compound is hydrolyzed to 6α-fluoroprednisolone 17-(n-butyl carbonate) ($R_f=0.4$) in the same way as described in Example 1(c).

EXAMPLE 61

(a) 1 g of 16α- or β-methyl-prednisolone 17-(n-butyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) 16α- or β-methyl-prednisolone 17-(n-butyl carbonate)-21-(methyl carbonate), (2) 16α- or β-methyl-prednisolone 17-(n-butyl carbonate)-21-(ethyl carbonate), (3) 16α- or β-methyl-prednisolone 17-(n-butyl carbonate)-21-(n-propyl carbonate), (4) 16α- or β-methyl-prednisolone 17-(n-butyl carbonate)-21-(n-butyl carbonate), (5) 16α- or β-methyl-prednisolone 17-(n-butyl carbonate)-21-(isopropyl carbonate), (6) 16α- or β-methyl-prednisolone 17-(n-butyl carbonate)-21-(isobutyl carbonate), (7) 16α- or β-methyl-prednisolone 17-(n-butyl carbonate)-21-acetate, (8) 16α- or β-methyl-prednisolone 17-(n-butyl carbonate)-21-propionate, (9) 16α- or β-methyl-prednisolone 17-(n-butyl carbonate)-21-butylrate, (10) 16α- or β-methyl-prednisolone 17-(n-butyl carbonate)-21-valerate, (11) 16α- or β-methyl-prednisolone 17-(n-butyl carbonate)-21-cyclopropanecarboxylate and (12) 16α- or β-methyl-prednisolone 17-(n-butyl carbonate)-21-cyclopentylpropionate is otained in each case.

(b) 3 g of 16α- or β-methyl-prednisolone 17-(n-butyl carbonate) are reacted with methanesulfonyl chloride, and the product is worked up, in the same way as described in Example 2(f). After crystallization from ether, 16α- or β-methyl-prednisolone 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 16α- or β-methyl-prednisolone 17-(n-butyl carbonate)-21-p-toluenesulfonate or, respectively, 16α- or β-methyl-prednisolone 17-(n-butyl carbonate)-21-p-chlorobenzenesulfonate is obtained.

(c) The 16α- or β-methyl-prednisolone di-(n-butyl) orthocarbonate ($R_f=0.6$) first required for the reaction is prepared according to German Pat. No. 1,668,079 from 16α- or β-methyl-prednisolone and tetra-(n-butyl) orthocarbonate.

Subsequently, the first-mentioned compound is hydrolyzed to 16α- or β-methyl-prednisolone 17-(n-butyl carbonate) ($R_f=0.4$) in the same way as described in Example 1(c).

EXAMPLE 62

(a) 1 g of 6α,16α- or β-dimethyl-prednisolone 17-(n-butyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) 6α,16α- or β-dimethyl-prednisolone 17-(n-butyl carbonate)-21-(methyl carbonate), (2) 6α,16α- or β-dimethyl-prednisolone 17-(n-butyl carbonate)-21-(ethyl carbonate), (3) 6α,16α- or β-dimethyl-prednisolone 17-(n-butyl carbonate)-21-(n-propyl carbonate), (4) 6α,16α- or β-dimethyl-prednisolone 17-(n-butyl carbonate)-21-(n-butyl carbonate), (5) 6α,1-6α- or β-dimethyl-prednisolone 17-(n-butyl carbonate)-21-(isopropyl carbonate), (6) 6α,16α- or β-dimethyl-prednisolone 17-(n-butyl carbonate)-21-(isobutyl carbonate), (7) 6α,16α- or β-diemthyl-prednisolone 17-(n-butyl carbonate)-21-acetate, (8) 6α,16α- or β-dimethyl-prednisolone 17-(n-butyl carbonate)-21-propionate, (9) 6α,16α- or β-dimethyl-prednisolone 17-(n-butyl carbonate)-21-butyrate, (10) 6α,16α- or β-dimethyl-prednisolone 17-(n-butyl carbonate)-21-valerate, (11) 6α,1-6α- or β-dimethyl-prednisolone 17-(n-butyl carbonate)-21-cyclopropanecarboxylate and (12) 6α,16α- or β-dimethyl-prednisolone 17-(n-butyl carbonate)-21-cyclopentylpropionate is obtained in each case.

(b) 3 g of 6α,16α- or β-dimethyl-prednisolone 17-(n-butyl carbonate) are reacted with methanesulfonyl chloride, and the product is worked up, in the same way as described in Example 2(f). After crystallization from ether, 6α,16α- or β-dimethyl-prednisolone 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α,16α- or β-dimethyl-prednisolone 17-(n-butyl carbonate)-21-p-toluenesulfonate or, respectively, 6α,16α- or β-dimethyl-prednisolone 17-(n-butyl carbonate)-21-p-chlorobenzenesulfonate is obtained.

(c) The 6α,16α- or β-dimethyl-prednisolone di-(n-butyl) orthocarbonate ($R_f=0.6$) first required for the reaction is prepared according to German Pat. No. 1,668,079 from 6α,16α- or β-dimethyl-prednisolone and tetra-(n-butyl) orthocarbonate.

Subsequently, the first-mentioned compound is hydrolyzed to 6α,16α-or β-dimethyl-prednisolone 17-(n-butyl carbonate) ($R_f=0.4$) in the same way as described in Example 1(c).

EXAMPLE 63

(a) 1 g of 9α-chloro-16α-methyl-prednisolone 17-(n-butyl carbonate) is reacted (1) with 0.8 mol of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1,3 ml of cyclopentylpropionyl chloride, instead of with methyl chloroformate, and the product is worked up, in the same way as described in Example 4(a).

The corresponding (1) 9α-chloro-16α-methyl-prednisolone 17-(n-butyl carbonate)-21-(methyl carbonate), (2) 9α-chloro-16α-methyl-prednisolone 17-(n-butyl carbonate)-21-(ethyl carbonate), (3) 9α-chloro-16α-methyl-prednisolone 17-(n-butyl carbonate)-21-(n-propyl carbonate), (4) 9α-chloro-16α-methyl-prednisolone 17-(n-butyl carbonate)-21-(n-butyl carbonate), (5) 9α-chloro-16α-methyl-prednisolone 17-(n-butyl carbonate)-21-(isopropyl carbonate), (6) 9α-chloro-16α-methyl-prednisolone 17-(n-butyl carbonate)-21-(isobutyl carbonate), (7) 9α-chloro-16α-methyl-prednisolone 17-(n-butyl carbonate)-21-acetate, (8) 9α-chloro-16α-methyl-prednisolone 17-(n-butyl carbonate)-21-propionate, (9) 9α-chloro-16α-methyl-prednisolone 17-(n-butyl carbonate)-21-butyrate, (10) 9α-chloro-16α-methyl-prednisolone 17-(n-butyl carbonate)-21-valerate, (11) 9α-chloro-16α-methyl-prednisolone 17-(n-butyl carbonate)-21-cyclopropanecarboxylate and (12) 9α-chloro-16α-methyl-prednisolone 17-(n-butyl carboate)-21-cyclopentylpropionate is obtained in each case.

(b) 3 g of 9α-chloro-16α-methyl-prednisolone 17-(n-butyl carbonate) are reacted with methanesulfonyl chloride, and the product is worked up, in the same way as described in Example 2(f). After crystallization from ether, 9α-chloro-16α-methyl-prednisolone 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 9α-chloro-16α-methyl-prednisolone 17-(n-butyl carbonate)-21-p-toluenesulfonate or, respectively, 9α-chloro-16α-methyl-prednisolone 17-(n-butyl carbonate)-21-p-chlorobenzenesulfonate is obtained.

(c) The 9α-chloro-16α-methyl-prednisolone di(n-butyl) orthocarbonate ($R_f=0.6$) first required for the reaction is prepared according to German Pat. No. 1,668,079 from 9α-chloro-16α-methyl-prednisolene and tetra-(n-butyl) orthocarbonate.

Subsequently, the first-mentioned compound is hydrolyzed to 9α-chloro-16α-methyl-prednisolone 17-(n-butyl carbonate) ($R_f=0.4$) in the same was as described in Example 1(c).

EXAMPLE 64

(a) 1 g of 9α-chloro-prednisolone 17-(n-butyl carbonate) is reacted (1) with 0.8 ml of methyl chloroformate and (2) with 0.8 ml of ethyl chloroformate, (3) with 0.9 of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate and the product is worked up, in the same way as described in Example 4(a).

The corresponding (1) 9α-chloro-prednisolone 17-(n-butyl carbonate)-21-(methyl carbonate), (2) 9α-chloro-prednisolone 17-(n-butyl carbonate)-21-(ethyl carbonate), (3) 9α-chloro-prednisolone 17-(n-butyl carbonate)-21-(n-propyl carbonate), (4) 9α-chloro-prednisolone 17-(n-butyl carbonate)-21-(n-butyl carbonate), (5) 9α-chloro-prednisolone 17-(n-butyl carbonate)-21-(isopropyl carbonate), (6) 9α-chloro-prednisolone 17-(n-butyl carbonate)-21-(isobutyl carbonate), (7) 9α-chloro-prednisolone 17-(n-butyl carbonate)-21-acetate, (8) 9α-chloro-prednisolone 17-(n-butyl carbonate)-21-propionate, (9) 9α-chloro-prednisolone 17-(n-butyl carbonate)-21-butyrate, (10) 9α-chloro-prednisolone 17-(n-butyl carbonate)-21-valerate, (11) 9α -chloro-prednisolone 17-(n-butyl carbonate)-21-cyclopropane-carboxylate and 12) 9α-chloro-prednisolone 17-(n-butyl carbonate)-21-cyclopentylpropionate is obtained in each case.

(b) 3 g of 9α-chloro-prednisolone 17-(n-butyl carbonate) are reacted with methanesulfonyl chloride, and the product is worked up, in the same way as described in Example 2(f). After crystallization from ether, 9α-chloro-prednisolone 17-(n-butyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 9α-chloro-prednisolone 17-(n-butyl carbonate)-21-p-toluenesulfonate or, respectively, 9α-chloro-prednisolone 17-(n-butyl carbonate)-21-p-chlorobenzenesulfonate is obtained.

(c) The 9α-chloro-prednisolone di-(n-butyl) orthocarbonate ($R_f$=0.6) first required for the reaction is prepared according to German Pat. No. 1,668,079 from 9α-chloro-prednisolone and tetra-(n-butyl) orthocarbonate.

Subsequently, the first-mentioned compound is hydrolyzed to 9α-chloro-prednisolone 17-(n-butyl carbonate) $R_f$=0.4) in the same way as described in Example 1(c).

EXAMPLE 65

(a) 1 g of prednisolone 17-(n-pentyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) prednisolone 17-(n-pentyl carbonate)-21-(methyl carbonate), (2) prednisolone 17-(n-pentyl carbonate)-21-(ethyl carbonate), (3) prednisolone 17-(n-pentyl carbonate)-21-(n-propyl carbonate), (4) prednisolone 17-(n-pentyl carbonate)-21-(n-butyl carbonate), (5) prednisolone 17-(n-pentyl carbonate)-21-(isopropyl carbonate), (6) prednisolone 17-(n-butyl carbonate(-21-(isobutyl carbonate), (7) prednisolone 17-(n-pentyl carbonate)-21-acetate, (8) prednisolone 17-(n-pentyl carbonate)-21-propionate, (9) prednisolone 17-(n-pentyl carbonate)-21-butyrate, (10) prednisolone 17-(n-pentyl carbonate)-21-valerate, (11) prednisolone 17-(n-pentyl carbonate)-21-cyclopropanecarboxylate and (12) prednisolone 17-(n-pentyl carbonate)-21-cyclopentylpropionate is obtained in each case.

(b) 3 g of prednisolone 17-(n-pentyl carbonate) are reacted with methanesulfonyl chloride, and the product is worked up, in the same way as described in Example 2(f). After crystallization from ether, prednisolone 17-(n-pentyl carbonate)-21-methanesulfonate is obtained.

If an equimolar amount of p-toluenesulfonyl chloride or of p-chlorobenzenesulfonyl chloride is employed in place of methanesulfonyl chloride, the corresponding prednisolone 17-(n-pentyl carbonate)-21-p-toluenesulfonate or, respectively, prednisolone 17-(n-pentyl carbonate)-21-p-chlorobenzenesulfonate is obtained.

(c) The prednisolone di-(n-pentyl) orthocarbonate ($R_f$=0.6) first required for the reaction is prepared according to German Pat. No. 1,668,079 from prednisolone and tetra-(n-pentyl) orthocarbonate. Subsequently, the first-mentioned compound is hydrolyzed to prednisolone 17-(n-butyl carbonate) ($R_f$=0.4) in the same way as described in Example 1(c).

EXAMPLE 66

(a) 1 g of prednisone 17-(n-pentyl carbonate) is reacted (1) with 0.8 ml of methyl chloroformate and (2) with 0.8 ml of methyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride instead of with methyl chloroformate, and the product is work up, in the same way as described in Example 4(a).

The corresponding (1) prednisone 17-(n-butyl carbonate)-21-(methyl carbonate), (2) prednisone 17-(n-pentyl carbonate)-21-(ethyl carbonate), (3) prednisone 17-(n-pentyl carbonate)-21-(n-propyl carbonate), (4) prednisone 17-(n-pentyl carbonate)-21-(n-butyl carbonate), (5) prednisone 17-(n-pentyl carbonate)-21-(isopropyl carbonate), (6) prednisone 17-(n-pentyl carbonate)-21-(isobutyl carbonate), (7) prednisone 17-(n-pentyl carbonate)-21-acetate, (8) predisone 17-(n-pentyl carbonate)-21-propionate, (9) prednisone 17-(n-pentyl carbonate)-21-butyrate, (10) prednisone 17-(n-propyl carbonate)-21-valerate, (11) prednisone 17-(n-propyl carbonate)-21-cyclopropanecarboxylate and (12) prednisone 17-(n-pentyl carbonate)-21-cyclopentylpropionate is obtained in each case.

(b) 3 g of prednisone 17-(n-propyl carbonate) are reacted with methanesulfonyl chloride, and the product is worked up, in the same way as described in Example 2(f). After crystallization from ether, prednisone 17-(n-pentyl carbonate)-21-methanesulfonate is obtained.

If an equimolar amount of p-toluenesulfonyl chloride or of p-chlorobenzenesulfonyl chloride is employed in place of methanesulfonyl chloride, the corresponding prednisone 17-(n-pentyl carbonate)-21-p-toluenesulfonate or, respectively, prednisone 17-(n-pentyl carbonate)-21-p-chlorobenzenesulfonate is obtained.

(c) The prednisone di-(n-pentyl) orthocarbonate ($R_f$=0.6) first required for the reaction, is prepared according to German Pat. No. 1,668,079 from prednisone and tetra-(n-pentyl) orthocarbonate. Subsequently, the first-mentioned compound is hydrolyzed to prednisone 17-(n-pentyl carbonate) ($R_f$=0.4) in the same way as described in Example 1(c).

EXAMPLE 67

(a) 1 g of cortisone 17-(n-pentyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) cortisone 17-(n-pentyl carbonate)-21-(methyl carbonate), (2) cortisone 17-(n-pentyl carbonate)-21-(ethyl carbonate), (3) cortisone 17-(n-pentyl carbonate)-21-(n-propyl carbonate), (4) cortisone 17-(n-pentyl carbonate)-21-(n-butyl carbonate), (5) cortisone 17-(n-pentyl carbonate)-21-(isopropyl carbonate), (6) cortisone 17-(n-pentyl carbonate)-21-isobutyl carbonate(, (7) cortisone 17-(n-pentyl carbonate)-21-acetate, (8) cortisone 17-(n-pentyl carbonate)-21-propionate, (9) cortisone 17-(n-pentyl carbonate)-21-butyrate, (10-cortisone 17-(n-pentyl carbonate)-21-valerate, (11) cortisone 17-(n-pentyl carbonate)-21-cyclopropanecarboxylate and (12) cortisone 17-(n-pentyl carbonate)-21-cyclopentylpropionate is obtained in each case.

(b) 3 g of cortisone 17-(n-pentyl carbonate) are reacted with methanesulfonyl chloride, and the product is worked up, in the same way as described in Example 2(f). After crystallization from ether, cortisone 17-(n-pentyl carbonate)-21-methanesulfonate is obtained.

If an equimolar amount of p-toluenesulfonyl chloride or of p-chlorobenzenesulfonyl chloride is employed in place of methanesulfonyl chloride, the corresponding cortisone 17-(n-pentyl carbonate)-21-p-toluenesulfonate or, respectively, cortisone 17-(n-pentyl carbonate)-21-p-chlorobenzenesulfonate is obtained.

(c) The cortisone di-(n-pentyl) orthocarbonate ($R_f \approx 0.6$) first required for the reaction, is prepared according to German Pat. No. 1,668,079 from cortisone and tetra-(n-pentyl) orthocarbonate. Subsequently, the first-mentioned compound is hydrolyzed to cortisone 17-(n-pentyl carbonate) ($R_f \approx 0.4$) in the same way as described in Example 1(c).

EXAMPLE 68

(a) 1 g of cortisol 17-(n-pentyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9ml of butyryl chloride, (10) with 1 ml of valeryl chloride, (11) with 1 ml of cyclopropanecarboxylic acid chloride and (12) with 1.3 ml of cyclopentylpropionyl chloride instead of with methyl chloroformate, and the product is worked up, in the same way as described in Example 4(a).

The corresponding (1) cortisol 17-(n-pentyl carbonate)-21-(methyl carbonate), (2) cortisol 17-(n-pentyl carbonate)-21-(ethyl carbonate), (3) cortisol 17-(n-pentyl carbonate)-21-(n- propyl carbonate), (4) cortisol 17-(n-pentyl carbonate)-21-(n-butyl carbonate), (5) cortisol 17-(n-pentyl carbonate)-21-(isopropyl carbonate), (6) cortisol 17-(n-pentyl carbonate)-21-(isobutyl carbonate), (7) cortisol 17-(n-pentyl carbonate)-21-acetate, (8) cortisol 17-(n-pentyl carbonate)-21-propionate, (9) cortisol 17-(n-pentyl carbonate)-21-butyrate, (10) cortisol 17-(n-pentyl carbonate)-21-valerate, (11) cortisol 17-(n-pentyl carbonate)-21-cyclopropanecarboxylate and (12) cortisol 17-(n-pentyl carbonate)-21-cyclopentylpropionate is obtained in each case.

(b) 3 g of cortisol 17-(n-pentyl carbonate) are reacted with methanesulfonyl chloride, and the product is worked up, in the same way as described in Example 2 (f). After crystallization from ether, cortisol 17-(n-pentyl carbonate)-21-methanesulfonate is obtained.

If an equimolar amount of p-toluenesulfonyl chloride or of p-chlorobenzenesulfonyl chloride is employed in place of methanesulfonyl chloride, the corresponding cortisol 17-(n-pentyl carbonate)-21-p-toluenesulfonate or, respectively, cortisol 17-(n-pentyl carbonate)-21-p-chlorobenzenesulfonate is obtained.

(c) The cortisol di-(n-pentyl) orthocarbonate ($R_f \approx 0.6$) first required for the reaction, is prepared according to German Pat. No. 1,668,079 from cortisol and tetra-(n-pentyl) orthocarbonate. Subsequently, the first-mentioned compound is hydrolyzed to cortisol 17-(n-pentyl carbonate) ($R_f \approx 0.4$) in the same way as described in Example 1 (c).

EXAMPLE 69

(a) 1 g of beclomethasone 17-(n-pentylcarbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of n-pentylchloride, (11) with 1 ml of cyclopropanecarboxylic acid chloride and (12) with 1.3 ml of cyclopentylpropionyl chloride, instead of with methyl chloroformate, and the prouct is worked up, in the same way as described in Example 4(a).

The corresponding (1) beclomethasone 17-(n-pentyl carbonate)-21-(methyl carbonate), (2) beclomethasone 17-(n-pentyl carbonate)-21-(ethyl carbonate), (3) beclomethasone 17-(n-pentyl carbonate)-21-(n-propyl carbonate), (4) beclomethasone 17-(n-pentyl carbonate)-21-(n-butyl carbonate), (5) beclomethasone 17-(n-pentyl carbonate)-21-(isopropyl carbonate), (6) beclomethasone 17-(n-pentyl carbonate)-21-(isobutyl carbonate), (7) beclomethasone 17-(n-pentyl carbonate)-21-acetate, (8) beclomethasone 17-(n-pentylcarbonate)-21-propionate, (9) beclomethasone 17-(n-pentyl carbonate)-21-butyrate, (10) beclomethasone 17-(n-pentyl carbonate)-21-valerate, (11) beclomethasone 17-(n-pentyl carbonate)-21-cyclopropanecarboxylate and (12) beclomethasone 17-(n-pentyl carbonate)-21-cyclopentylpropionate is obtained in each case.

(b) 3 g of beclomethasone 17-(n-pentyl carbonate) are reacted with methanesulfonyl chloride, and the product is worked up, in the same way as described in Example 2 (f). After crystallization from ether, beclomethasone 17-(n-pentyl carbonate)-21-methanesulfonate is obtained.

If an equimolar amount of p-toluenesulfonyl chloride or of p-chlorobenzenesulfonyl chloride is employed in place of methanesulfonyl chloride, the corresponding beclomethasone 17-(n-pentyl carbonate)-21-p-toluenesulfonate or, respectively, beclomethasone 17-(n-pentylcarbonate)-21-p-chlorobenzenesulfonate is obtained.

(c) The beclomethasone di-(n-pentyl) orthocarbonate ($R_f \approx 0.6$) first required for the reaction, is prepared according to German Pat. No. 1,668,079 from beclomethasone and tetra-(n-pentyl) orthocarbonate.

Subsequently, the first-mentioned compound is hydrolyzed to beclomethasone 17-(n-pentyl carbonate) ($R_f \approx 0.4$) in the same way as described in Example 1 (c).

EXAMPLE 70

(a) 1 g of 6α-fluorodexamethasone 17-(n-pentyl carbonate) are reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 6α-fluorodexamethasone 17-(n-pentyl carbonate)-21-(methyl carbonate), (2) 6α-fluorodexamethasone 17-(n-pentyl carbonate)-21-(ethyl carbonate), (3) 6α-fluorodexamethasone 17-(n-pentyl carbonate)-21-(n-propyl carbonate), (4) 6α-fluorodexamethasone 17-(n-pentyl carbonate)-21-(n-butyl carbonate), (5) 6α-fluorodexamethasone 17-(n-pentyl carbonate)-21-(isopropyl carbonate), (6) 6α-fluorodexamethasone 17-(n-pentyl carbonate)-21-(isobutyl carbonate), (7) 6α-fluorodexamethasone 17-(n-pentyl carbonate)-21-acetate, (8) 6α-fluorodexamethasone 17-(n-pentyl carbonate)-21-propionate, (9) 6α-fluorodexamethasone 17-(n-pentyl carbonate)-21-butyrate, (10) 6α-fluorodexamethasone 17-(n-pentyl carbonate)-21-valerate, (11) 6α-fluorodexamethasone 17-(n-pentyl carbonate)-21-cyclopropanecarboxylate and (12) 6α-fluorodexamethasone 17-(n-pentyl carbonate)-21-cyclopentylpropionate is obtained in each case.

(b) 3 g of 6α-fluorodexamethasone 17-(n-pentyl carbonate) are reacted with methanesulfonyl chloride, and the product is worked up, in the same way as described in Example 2 (f). After crystallization from ether, 6α-fluorodexamethasone 17-(n-pentyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α-fluorodexamethasone 17-(n-pentyl carbonate)-21-p-toluenesulfonate or, respectively, 6α-fluorodexamethasone 17-(n-pentyl carbonate)-21-p-chlorobenzenesulfonate is obtained.

(c) The 6α-fluorodexamethasone di-(n-pentyl) orthocarbonate ($R_f \approx 0.6$) first required for the reaction, is prepared according to German Pat. No. 1,668,079 from 6α-fluorodexamethasone and tetra-(n-pentyl)orthocarbonate.

Subsequently, the first-mentioned compound is hydrolyzed to 6α-fluorodexamethasone 17-(n-pentyl carbonate) ($R_f \approx 0.4$) in the same way as described in Example 1 (c).

EXAMPLE 71

(a) 1 g of betamethasone 17-(n-pentyl carbonate) are reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) betamethasone 17-(n-pentyl carbonate)-21-(methyl carbonate), (2) betamethasone 17-(n-pentyl carbonate)-21-(ethyl carbonate), (3) betamethasone 17-(n-pentyl carbonate)-21-(n-propyl carbonate), (4) betamethasone 17-(n-pentyl carbonate)-21-(n-butyl carbonate), (5) betamethasone 17-(n-pentyl carbonate)-21-(isopropyl carbonate), (6) betamethasone 17-(n-pentyl carbonate)-21-(isobutyl carbonate), (7) betamethasone 17-(n-pentyl carbonate)-21-acetate, (8) betamethasone 17-(n-pentyl carbonate)-21-propionate, (9) betamethasone 17-(n-pentyl carbonate)-21-butyrate, (10) betamethasone 17-(n-pentyl carbonate)-21-valerate, (11) betamethasone 17-(n-pentyl carbonate)-21-cyclopropanecarboxylate and (12) betamethasone 17-(n-pentyl carbonate)-21-cyclopentylpropionate is obtained in each case.

(b) 3 g of betamethasone 17-(n-pentyl carbonate) are reacted with methanesulfonyl chloride, and the product is worked up, in the same way as described in Example 2 (f). After crystallization from ether, betamethasone 17-(n-pentyl carbonate)21-methanesulfonate is obtained.

If an equimolar amount of p-toluenesulfonyl chloride or of p-chlorobenzenesulfonyl chloride is employed in place of methanesulfonyl chloride, the corresponding betamethasone 17-(n-pentyl carbonate)-21-p-toluenesulfonate or, respectively, betamethasone 17-(n-pentyl carbonate)-21-p-chlorobenzenesulfonate is obtained.

(c) The betamethasone di-(n-pentyl) orthocarbonate ($R_f \approx 0.6$) first required for the reaction, is prepared according to German Pat. No. 1,668,079 from betamethasone and tetra-(n-pentyl) orthocarbonate.

Subsequently, the first-mentioned compound is hydrolyzed to betamethasone 17-(n-pentyl carbonate) ($R_f \approx 0.4$) in the same way as described in Example 1 (c).

EXAMPLE 72

(a) 1 g of 6α-fluoro-prednisolone 17-(n-pentyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 6α-fluoro-prednisolone 17-(n-pentyl carbonate)-21-(methyl carbonate), (2) 6α-fluoro-prednisolone 17-(n-pentyl carbonate)-21-(ethyl carbonate), (3) 6α-fluoro-prednisolone 17-(n-pentyl carbonate)-21-(n-propyl carbonate), (4) 6α-fluoro-prednisolone 17-(n-pentyl carbonate)-21-(n-butyl carbonate), (5) 6α-fluoro-prednisolone 17-(n-pentyl carbonate)-21-(isopropyl carbonate), (6) 6α-fluoro-prednisolone 17-(n-pentyl carbonate)-21-(isobutyl carbonate), (7) 6α-fluoro-prednisolone 17-(n-pentyl carbonate)-21-acetate, (8) 6α-fluoro-prednisolone 17-(n-pentyl carbonate)-21-propionate, (9) 6α-fluoro-prednisolone 17-(n-pentyl carbonate)-21-butyrate, (10) 6α-fluoro-prednisolone 17-(n-pentyl carbonate)-21-valerate, (11) 6α-fluoro-prednisolone 17-(n-pentyl carbonate)-21-cyclopropanecarboxylate and (12) 6α-fluoro-prednisolone 17-(n-pentyl carbonate)-21-cyclopentylpropionate is obtained in each case.

(b) 3 g of 6α-fluoro-prednisolone 17-(n-pentyl carbonate) are reacted with methanesulfonyl chloride, and the product is worked up, in the same way as described in Example 2 (f). After crystallization from ether, 6α-fluoro-prednisolone 17-(n-pentyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α-fluoro-prednisolone 17-(n-pentyl carbonate)-21-p-toluenesulfonate or, respectively, 6α-fluoro-prednisolone 17-(n-pentyl carbonate)-21-p-chlorobenzenesulfonate is obtained.

(c) The 6α-fluoro-prednisolone di-(n-pentyl) orthocarbonate ($R_f \approx 0.6$) first required for the reaction, is prepared according to German Pat. No. 1,668,079 from 6α-fluoro-prednisolone and tetra-(n-pentyl) orthocarbonate.

Subsequently, the first-mentioned compound is hydrolyzed to 6α-fluoro-prednisolone 17-(n-pentyl carbonate) ($R_f \approx 0.4$) in the same way as described in Example 1 (c).

EXAMPLE 73

(a) 1 g of 16α- or β-methyl-prednisolone 17-(n-pentyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 16α- or β-methyl-prednisolone 17-(n-pentyl carbonate)-21-(methyl carbonate), (2) 16α- or β-methyl-prednisolone 17-(n-pentyl carbonate)-21-(ethyl carbonate), (3) 16α- or β-methyl-prednisolone 17-(n-pentyl carbonate)-21-(n-propyl carbonate), (4) 16α- or β-methyl-prednisolone 17-(n-pentyl carbonate)-21-(n-butyl carbonate), (5) 16α- or β-methyl-prednisolone 17-(n-pentyl carbonate)-21-(isopropyl carbonate), (6) 16α- or β-methyl-prednisolone 17-(n-pentyl carbonate)-21-(isobutyl carbonate), (7) 16α- or β-methyl-prednisolone 17-(n-pentyl carbonate)-21-acetate, (8) 16α-or β-methyl-prednisolone 17-(n-pentyl carbonate)-21-propionate, (9) 16α- or β-methyl-prednisolone 17-(n-pentyl carbonate)-21-butyrate, (10) 16α- or β-methyl-prednisolone 17-(n-pentyl carbonate)-21-valerate, (11) 16α- or β-methyl-prednisolone 17-(n-pentyl carbonate)-21-cyclopropanecarboxylate and (12) 16α- or β-methyl-prednisolone 17-(n-pentyl carbonate)-21-cyclopentylpropionate is obtained in each case.

(b) 3 g of 16α- or β-methyl-prednisolone 17-(n-pentyl carbonate) are reacted with methanesulfonyl chloride, and the product is worked up, in the same way as described in Example 2 (f). After crystallization from ether, 16α- or β-methyl-prednisolone 17-(n-pentyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 16α- or β-methyl-prednisolone 17-(n-pentylcarbonate)-21-p-toluenesulfonate or, respectively, 16α- or β-methyl-prednisolone 17-(n-pentyl carbonate)-21-p-chlorobenzenesulfonate is obtained.

(c) The 16α- or β-methyl-prednisolone di-(n-pentyl)orthocarbonate ($R_f \approx 0.6$) first required for the reaction is prepared according to German Pat. No. 1,668,079 from 16α- or β-methyl-prednisolone and tetra-(n-pentyl) orthocarbonate.

Subsequently, the first-mentioned compound is hydrolyzed to 16α- or β-methyl-prednisolone 17-(n-pentyl carbonate) ($R_f \approx 0.4$) in the same way as described in Example 1 (c).

EXAMPLE 74

(a) 1 g of 6α,16α- or β-dimethyl-prednisolone 17-(n-pentyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with metyl chloroformate, and the product is worked up, in the same way as described in Example 4 (a).

The corresponding (1) 6α,16α- or β-dimethyl-prednisolone 17-(n-pentyl carbonate)-21-(methyl carbonate), (2) 6α,16α- or β-dimethyl-prednisolone 17-(n-pentyl carbonate)-21-(ethyl carbonate), (3) 6α,16α- or β-dimethyl-prednisolone 17-(n-pentyl carbonate)-21-(n-propyl carbonate), (4) 6α,16α- or β-diethyl-prednisolone 17-(n-pentyl carbonate)-21-(n-butyl carbonate), (5) 6α,16α- or β-dimethyl-prednisolone 17-(n-pentyl carbonate)-21-(isopropyl carbonate), (6) 6α,16α- or β-dimethyl-prednisolone 17-(n-pentyl carbonate)-21-(isobutyl carbonate), (7) 6α,16α- or β-dimethyl-prednisolone 17-(n-pentyl carbonate)-21-acetate, (8) 6α,16α- or β-dimethyl-prednisolone 17-(n-pentyl carbonate)-21-propionate, (9) 6α,16α- or β-dimethyl-prednisolone 17-(n-pentyl carbonate)-21-butyrate, (10) 6α,16α- or β-dimethyl-prednisolone 17-(n-pentyl carbonate)-21-valerate, (11) 6α,16α- or β-dimethyl-prednisolone 17-(n-pentyl carbonate)-21-cyclopropanecarboxylate and (12) 6α,16α- or β-dimethyl-prednisolone 17-(n-pentyl carbonate)-21-cyclopentylpropionate is obtained in each case.

(b) 3 g of 6α,16α- or β-dimethyl-prednisolone 17-(n-pentyl carbonate) are reacted with methanesulfonyl chloride, and the product is worked up, in the same way as described in Example 2 (f). After crystallization from ether, 6α,16α- or β-dimethyl-prednisolone 17-(n-pentyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 6α,16α- or β-dimethyl-prednisolone 17-(n-pentyl carbonate)-21-p-toluenesulfonate or, respectively, 6α,16α- or β-dimethyl-prednisolone 17-(n-pentyl carbonate)-21-p-chlorobenzenesulfonate is obtained.

(c) The 6α,16α- or β-dimethyl-prednisolone di-(n-pentyl orthocarbonate ($R_f \approx 0.6$) first required for the reaction is prepared according to German Pat. No. 1,668,079 from 6α,16α- or β-dimethyl-prednisolone and tetra-(n-pentyl) orthocarbonate.

Subsequently, the first-mentioned compound is hydrolyzed to 6α,16α- or β-dimethyl-prednisolone 17-(n-pentyl carbonate) ($R_f \approx 0.4$) in the same way as described in Example 1 (c).

EXAMPLE 75

(a) 1 g of 9α-chloro-16α-methyl-prednisolone 17-(n-pentyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 9α-chloro-16α-methyl-prednisolone 17-(n-pentyl carbonate)-21-(methyl carbonate), (2) 9α-chloro-16α-methyl-prednisolone 17-(n-pentyl carbonate)-21-(ethyl carbonate), (3) 9α-chloro-16α-methyl-prednisolone 17-(n-pentyl carbonate)-21-(n-propyl carbonate), (4) 9α-chloro-16α-methyl-prednisolone 17-(n-pentyl carbonate)-21-(n-butyl carbonate), (5) 9α-chloro-16α-methyl-prednisolone 17-(n-pentyl carbonate)-21-(isopropyl carbonate), (6) 9α-chloro-16α-metyl-prednisolone 17-(n-pentyl carbonate)-21-(isobutyl carbonate), (7) 9α-chloro-16α-methyl-prednisolone 17-(n-pentyl carbonate)-21-acetate, (8) 9α-chloro-16α-methyl-prednisolone 17-(n-pentyl carbonate)-21-propionate, (9) 9α-chloro-16α-methyl-prednisolone 17-(n-pentyl carbonate)-21-butyrate, (10) 9α-chloro-16α-methyl-prednisolone 17-(n-pentyl carbonate)-21-valerate, (11) 9α-chloro-16α-methyl-prednisolone 17-(n-pentyl carbonate)-21-cyclopropanecarboxylate and (12) 9α-chloro-16α-methyl-prednisolone 17-(n-pentyl carbonate) 21-cyclopentylpropionate is obtained in each case.

(b) 3 g of 9α-chloro-16α-methyl-prednisolone 17-(n-pentyl carbonate) are reacted with methanesulfonyl chloride, and the product is worked up, in the same way as described in Example 2 (f). After crystallization from ether, 9α-chloro-16α-methyl-prednisolone 17-(n-pentyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 9α-chloro-16α-methyl-prednisolone 17-(n-pentyl carbonate)-21-p-toluenesulfonate or, respectively, 9α-chloro-16α-methyl-prednisolone 17-(n-pentyl carbonate)-21-p-chlorobenzenesulfonate is obtained.

(c) The 9α-chloro-16α-methyl-prednisolone di-(n-pentyl orthocarbonate ($R_f \approx 0.6$) first required for the reaction is prepared according to German Pat. No. 1,668,079 from 9α-chloro-16α-methyl-prednisolone and tetra-(n-pentyl) orthocarbonate.

Subsequently, the first-mentioned compound is hydrolyzed to 9α-chloro-16α-methyl-prednisolone 17-(n-pentyl carbonate) ($R_f \approx 0.4$) in the same way as described in Example 1 (c).

EXAMPLE 76

(a) 1 g of 9α-chloro-prednisolone 17-(n-pentyl carbonate) is reacted (1) with 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4 (a).

The corresponding (1) 9α-chloro-prednisolone 17-(n-pentyl carbonate)-21-(methyl carbonate), (2) 9α-chloro-prednisolone 17-(n-pentyl carbonate)-21-(ethyl carbonate), (3) 9α-chloro-prednisolone 17-(n-pentyl carbonate)-21-(n-propyl carbonate), (4) 9α-chloro-prednisolone 17-(n-pentyl carbonate)-21-(n-butyl carbonate), (5) 9α-chloro-prednisolone 17-(n-pentyl carbonate)-21-(isopropyl carbonate), (6) 9α-chloro-prednisolone 17-(n-pentyl carbonate)-21-(isobutyl carbonate, (7) 9α-chloro-prednisolone 17-(n-pentyl carbonate)-21-acetate, (8) 9α-chloro-prednisolone 17-(n-pentyl carbonate)-21-propionate, (9) 9α-chloro-prednisolone 17-(n-pentyl carbonate)-21-butyrate, (10) 9α-chloro-prednisolone 17-(n-pentyl carbonate)-21-valerate, (11) 9α-chloro-prednisolone 17-(n-pentyl carbonate)-21-cyclopropanecarboxylate and (12) 9α-chloro-prednisolone 17-(n-pentyl carbonate)21-cyclopentylpropionate is obtained in each case.

(b) 3 g of 9α-chloro-prednisolone 17-(n-pentyl carbonate) are reacted with methanesulfonyl chloride, and the product is worked up, in the same way as described in Example 2 (f). After crystallization from ether, 9α-chloro-prednisolone 17-(n-pentyl carbonate)-21-methanesulfonate is obtained.

If an equimolar amount of p-toluenesulfonyl chloride or of p-chlorobenzenesulfonyl chloride is employed in place of methanesulfonyl chloride, the corresponding 9α-chloro-prednisolone 17-(n-pentyl carbonate)-21-p-toluenesulfonate or, respectively, 9α-chloro-prednisolone 17-(n-pentyl carbonate)-21-p-chlorobenzenesulfonate is obtained.

(c) The 9α-chloro-prednisolone di-(n-pentyl orthocarbonate ($R_f \approx 0.6$) first required for the reaction is prepared according to German Pat. No. 1,668,079 from 9α-chloro-prednisolone and tetra-(valeryl) orthocarbonate.

Subsequently, the first-mentioned compound is hydrolyzed to 9α-chloro-prednisolone 17-(n-pentyl carbonate) ($R_f \approx 0.4$) in the same way as described in Example 1 (c).

EXAMPLE 77

6 g of 6,16α-dimethyl-4,6-pregnadiene-11β,17α,21-triol-3,2-c-2-phenylpyrazole (= bimedrazole, this abbreviation is also used in the text which follows for this complete nomenclature) are dissolved in 125 g of absolute dioxane and 500 mg of p-toluenesulfonic acid and 16.5 ml of tetraethyl orthocarbonate are added successively. After stirring for 6 hours at 20° C., a few drops of pyridine are added in order to neutralize the acid and the reaction mixture is poured into water, whereupon an oil precipitates; this is filtered off through a fluted filter. The oil is taken up in methylene choride and the extract is washed in water, dried and distilled to dryness in vacuo. 7.9 g of bimedrazole 17,21-(diethyl carbonate) are obtained in the form of a foam.

IR (KBr): 3,560, 3,400, 2,980, 2,930, 2,880, 1,720, 1,595, 1,500, 1,200, 1,130, 1,035 and 755 cm$^{-1}$ UV (CH$_3$OH): $\lambda_{max1}=312$ m$\mu$ ($\epsilon=20,600$); $\lambda_{max2}=280$ m$\mu$ ($\epsilon=17,100$)

TLC: (solvent: methylene chloride/methanol=19:1, developed once) R$_f$=0.45 (reaction product) and R$_f$=0.10 starting material, bimedrazole).

EXAMPLE 78

(a) A solution of 3 g of bimedrazole 17,21-(diethyl) orthocarbonate in 120 ml of glacial acetic acid and 0.6 ml of water is left to stand for 5 hours at 22° C. Monitoring by TLC showed that an optimum amount of the desired bimedrazole 17-(ethyl carbonate) was present after this time. The reaction mixture is poured into 1.5 l of water, the pH of which has been brought to 5 with ammonia solution, and an amorphous precipitate separates out. After filtering off, washing with water and drying, 2.8 g of amorphous bimedrazole 17-(ethyl carbonate) are obtained after digesting.

IR: 3,420–3,500 (broad), 2,940, 2,880, 1,735, 1,715 1,595, 1,500, 1,265 and 760 cm$^{-1}$ TLC: R$_f$=0.25

UV: $\lambda_{max1}=312$ m$\mu$ ($\epsilon=20,600$); $\lambda_{max2}=280$ m$\mu$ ($\epsilon=17,100$)

EXAMPLE 79

(a) 1 g of bimedrazole 17-(ethyl carbonate) is reacted with (1) 0.8 ml of methyl chloroformate and (2) with 0.8 ml of ethyl chloroformate, (3) with 0.9 ml of n-propyl chloroformate, (4) with 0.9 ml of n-butyl chloroformate, (5) with 1.0 ml of isopropyl chloroformate, (6) with 1.0 ml of isobutyl chloroformate, (7) with 0.8 ml of acetyl chloride, (8) with 0.8 ml of propionyl chloride, (9) with 0.9 ml of butyryl chloride, (10) with 1 ml of valeryl chloride, (11) with 1 ml of cyclopropanecarboxylic acid chloride and (12) with 1.3 ml of cyclopentylpropionyl chloride, instead of with methyl chloroformate, and the product is worked up, in the same way as described in Example 4(a).

The corresponding (1) bimedrazole 17-(ethyl carbonate)-21-(methyl carbonate), (2) bimedrazole 17-(ethyl carbonate)-21-(ethyl carbonate), (3) bimedrazole 17-(ethyl carbonate)-21-(n-propyl carbonate), (4) bimedrazole 17-(ethyl carbonate)-21-(n-butyl carbonate), (5) bimedrazole 17-(ethyl carbonate)-21-(isopropyl carbonate), (6) bimedrazole 17-(ethyl carbonate)-21-(isobutyl carbonate), (7) bimedrazole 17-(ethyl carbonate)-21-(acetate, (8) bimedrazole 17-(ethyl carbonate)-21-propionate, (9) bimedrazole 17-(ethyl carbonate)-21-butyrate, (10) bimedrazole 17-(ethyl carbonate)-21-valerate, (11) bimedrazole 17-(ethyl carbonate)-21-cyclopropanecarboxylate and (12) bimedrazole 17-(ethyl carbonate)-21-cyclopentylpropionate is obtained in each case.

(b) 3 g of bimedrazole 17-(ethyl carbonate) are reacted with methanesulfonyl chloride, and the product is worked up, in the same way as described in Example 2(f). After crystallization from ether, bimedrazole 17-(ethyl carbonate)-21-methanesulfonate is obtained.

If an equimolar amount of p-toluenesulfonyl chloride or of p-chlorobenzenesulfonyl chloride is employed in place of methanesulfonyl chloride, the corresponding bimedrazole 17-(ethyl carbonate)-21-p-toluenesulfonate or, respectively, bimedrazole 17-(ethyl carbonate)-21-p-chlorobenzenesulfonate is obtained.

EXAMPLE 80

The corresponding bimedrazole 17-(n-propyl carbonate)-21-carboxylates, bimedrazole 17-(n-propyl carbonate)-21-carbonates and bimedrazole 17-(n-propyl carbonate)-21-sulfonates are prepared in a manner the same as that which has just been described, from bimedrazole 17-(n-propyl carbonate) (preparation: bimedrazole+tetra-(n-propyl) orthocarbonate instead of tetraethyl orthocarbonate first gives amorphous bimedrazole 17,21-(di-(n-propyl) orthocarbonate), which is then analogously selectively solvolyzed in glacial acetic acid/water).

EXAMPLE 81:

1 ml of chloroacetic anhydride is added at 20° C. to a solution of 1 g of dexamethasone 17-(ethyl carbonate) in 30 ml of absolute tetrahydrofuran and 8 ml of absolute pyridine. After stirring for about 3 days at room temperature, the reaction mixture is poured into water containing sodium chloride, the resulting mixture is extracted with methylene chloride and the extract is washed with water, dried and concentrated in vacuo. After recrystallization from acetone/ether, the resulting foam gives dexamethasone 17-(ethyl carbonate)-21-chloroacetate with a melting point of 209° C.

IR: 3,460, 1,730, 1,660, 1,615, 1,600 and 1,260 cm$^{-1}$

MS: M$^+$=540

If cortisol 17-(ethyl carbonate), cortisone 17-(ethyl carbonate), prednisolone 17-(ethyl carbonate), prednisone 17-(ethyl carbonate), 6α-methylprednisolone 17-(ethyl carbonate), 6α-fluoro-prednisolone 17-(ethyl carbonate), betamethasone 17-(ethyl carbonate), beclomethasone 17-(ethyl carbonate), 9α-chloro-16α-methyl-prednisolone 17-(ethyl carbonate) and 9α-fluoro-dexamethasone 17-(ethyl carbonate) are employed in the reaction in place of dexamethasone 17-(ethyl carbonate), the corresponding 21-chloroacetates of the corticoid 17-(ethyl carbonate)s which have just been listed are obtained after an analogous course of reaction and working-up.

If the homologous corticoid 17-(n-propyl carbonate)s are employed in the reaction in place of dexamethasone 17-(ethyl carbonate)s and the other corticoid 17-(ethyl carbonate)s which have just been listed, the corresponding corticoid 17-(n-propyl carbonate)-21-chloroacetates are obtained after an analogous course of reaction and working-up.

EXAMPLE 82

2 ml of a CrO$_3$ oxidizing solution (preparation: 13.36 g of CrO$_3$ are dissolved in 30 ml of water; 11.5 ml of concentrated sulfuric acid are allowed to run in dropwise, with ice-cooling; the mixture is then made up to 50 ml) are added dropwise to a solution of 2.5 g of dexamethasone 17,21-bis-[ethyl carbonate] (prepared according to Example 2) in 75 ml of analytical grade acetone, at 0° C. and while stirring. After stirring for 1 hour at 0° C. and for 1.5 hours at 20° C., the reaction mixture is poured into water which contains the amount of pyridine or alkali metal bicarbonate required for neutralization, the resulting mixture is extracted repeatedly with methylene chloride and the extracts are washed with water, dried and concentrated in vacuo. The resulting foam is recrystallized from acetone/diisopropyl ether and gives 2.1 g of 11-dehydro-dexamethasone 17,21-bis-[ethyl carbonate] with a melting point of 212° C.

IR: 1,720–1,735, 1,660, 1,625, 1,280 and 1,260 cm$^{-1}$; no further bands present in the region of 3,420 cm$^{-1}$ (OH)!

MS: M$^+$ = 533.5

If, in each case, the corticoid 17-(alkyl carbonate)s which have been prepared in the preceding examples and which contain a hydroxyl group in the 11-position and either an (alkyl carbonate) group or alkylcarboxylate group or alkyl- or aryl-sulfonate group in the 21-position are employed in place of dexamethasone 17,21-bis-[ethyl carbonate] in the oxidation reaction which has just been described, the corresponding 11-dehydro-corticoid 17-(alkyl carbonate)-21-(alkyl carbonate)s, 11-dehydro-corticoid 17-(alkyl carbonate)-21-alkylcarboxylates, 11-dehydro-corticoid 17-(alkyl carbonate)-21-alkylsulfonates and 11-dehydro-corticoid 17-(alkyl carbonate)-21-arylsulfonates respectively are obtained after an analogous course of reaction and working-up.

EXAMPLE 83

1.71 g of propionic acid chloride are added dropwise while stirring at 0° C. to a solution of 6.85 g of prednisolon-17-ethyl-carbonate in 68 ml of pyridine. After stirring for 0.5 hour at 0° C. and 2 hours at 22° C., the solution is poured into 2 liters of water containing 100 g of dissolved sodium chloride, the precipitate is filtered off, washed with water and dried in vacuo over P$_2$O$_5$. 6.3 g of prednisolone-17-ethylcarbonate-21-propionate are obtained which in TLC still shows some secondary spots in a minor amount. In order to prepare the product in a very pure form, it is chromatographed on 300 g of silica gel (column diameter 3 cm) with toluene/ethyl acetate 8:2. The fractions showing in TLC at R$_F$=0.27 (toluene/ethyl acetate 65:35) one single spot are combined, the eluents are distilled off and the reaction product is crystallized from diisopropyl ether. 4.9 g of prednisolon-17-ethyl-carbonate-21-propionate melting at 112° C. are obtained.

UV: $\lambda_{max}$ = 241 nm, $\epsilon$ = 15800
IR: 3430, 1730, 1650, 1610, 1270, 1235 cm$^{-1}$.
$[\alpha]_D^{20°}$ = +57° (c=0.1; chloroform)

EXAMPLE 84

In the manner described in Example 83, 6.85 g of prednisolon-17-ethyl-carbonate in 68 ml of pyridine are reacted with 1.7 g of acetic anhydride, the reaction product is worked up and purified by chromatography. 4.8 g of prednisolon-17-ethyl-carbonate-21-acetate are obtained melting at 102° C.

UV: $\lambda_{max}$ = 240 nm, $\epsilon$ = 15400
IR: 3440, 1725, 1655, 1620, 1270, 1230 cm$^{-1}$

EXAMPLE 85:

In the manner described in Example 83, 6.85 g of prednisolon-17-n-propyl-carbonate in 68 ml of pyridine are reacted with 2 g of propionic acid chloride, the reaction product is worked up and purified by chromatography. 5.2 g of prednisolon-17-n-propyl carbonate-21-propionate melting at 108° C. are obtained.

UV: $\lambda_{max}$ = 241 nm, $\epsilon$ = 15500
IR: 3450, 1730, 1650, 1610, 1270, 1230 cm$^{-1}$

EXAMPLE 86:

In the manner described in Example 83, 6.85 g of prednisolon-17-n-propyl-carbonate in 68 ml of pyridine are reacted with 1.7 g of acetic anhydride, the reaction product is worked up and purified by chromatography. 5.0 g of prednisolon-17-n-propyl-carbonate-21-acetate melting at 98° C. are obtained.

UV: $\lambda_{max}$ = 242 nm, $\epsilon$ = 15300
IR: 3440, 1730, 1660, 1620, 1270, 1230 cm$^{-1}$

EXAMPLE 87:

In the manner described in Example 83, 6.85 g of cortisol-17-ethyl-carbonate in 68 ml of pyridine are reacted with 1.7 g of propionic acid chloride, the reaction product is worked up and purified by chromatography. 4.9 g of cortisol-17-ethyl-carbonate-21-propionate melting at 104° C. are obtained.

UV: $\lambda_{max}$ = 242 nm, $\epsilon$ = 15600
IR: 3440, 1730, 1655, 1610, 1270, 1230 cm$^{-1}$

EXAMPLE 88:

In the manner described in Example 83, 6.85 g of cortisol-17-n-propyl-carbonate in 68 ml of pyridine are reacted with 1.8 g of propionic acid chloride, the reaction product is worked up and purified by chromatography. 5.1 g of cortisol-17-n-propyl-carbonate-21-propionate melting at 110° C. are obtained.

UV: $\lambda_{max}$ = 242 nm, $\epsilon$ = 15400
IR: 3440, 1730, 1660, 1615, 1270, 1230 cm$^{-1}$

EXAMPLE 89

A solution of 12.5 g of prednisolon-17,21-diethyl-orthocarbonate (prepared from prednisolon and tetra-ethyl-orthocarbonate according to German Pat. No. 1,668,079) in 150 ml of glacial acetic acid containing 1 ml of water is left to stand for 2 hours at 20° C. and then poured into 2 liters of water containing 100 g of sodium chloride. The precipitate formed is filtered off, washed with water and dried in a high vacuum over P$_2$O$_5$. It is used for further reactions without aftertreatment. 7.2 g of prednisolon-17-ethyl carbonate are obtained.

By the usual extraction with methylene chloride, washing with water, distilling off and crystallization from diisopropyl ether another 3.6 g of prednisolon-17-ethyl-carbonate are obtained.

UV: $\lambda$ = 241 nm, $\epsilon$ = 15300
IR: 3450, 1730, 1650, 1610, 1265 cm$^{-1}$

EXAMPLE 90:

In the manner described in Example 89, 12.5 g of prednisolon-17,21-di-n-propyl-orthocarbonate (prepared from prednisolon and tetra-n-propyl-orthocarbonate according to German Pat. No. 1,668,079) are reacted, the reaction product is worked up and isolated. A total amount of 10.7 g of prednisolon-17-n-propylcarbonate is obtained.

UV: $\lambda_{max}$ = 241 nm, $\epsilon$ = 15400
IR: 3440, 1730, 1650, 1610, 1270 cm$^{-1}$

EXAMPLE 91:

In the manner described in Example 89, 12.5 g of cortisol-17,21-diethyl-orthocarbonate (prepared from cortisol and tetra-ethyl-orthocarbonate according to German Pat. No. 1,668,079) are reacted, the reaction product is worked up and isolated. 10.2 g of cortisol-17-ethyl-carbonate are obtained.

UV: $\lambda_{max}$ = 242 nm, $\epsilon$ = 15600
IR: 3450, 1730, 1655, 1615, 1270 cm$^{-1}$

EXAMPLE 92:

In the manner described in Example 89, 12.5 g of cortisol-17,21-di-n-propyl-orthocarbonate (prepared from cortisol and tetra-n-propyl-orthocarbonate according to German Pat. No. 1,668,079), are reacted, the reaction product is worked up and isolated. 10 g of cortisol-17-n-propyl-carbonate are obtained.

UV: $\lambda_{max} = 242$ nm, $\epsilon = 15400$
IR: 3450, 1730, 1655, 1615, 1270 cm$^{-1}$

We claim:

1. A compound selected from the group consisting of compounds of the formula

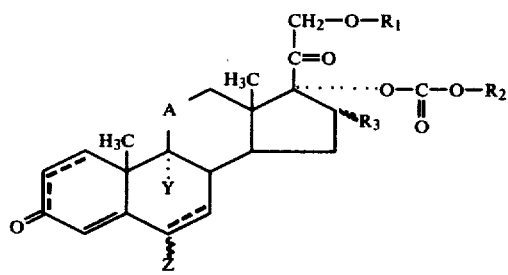

wherein A is

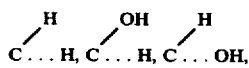

or C=O, and compounds of the formula

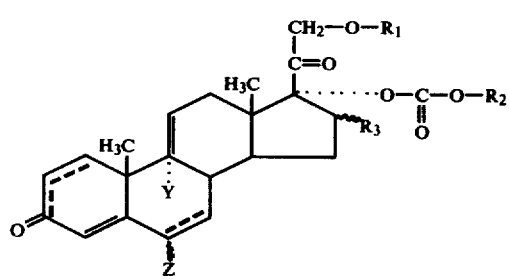

wherein
Y is hydrogen, fluorine, or chlorine;
Z is hydrogen, chlorine, fluorine, or methyl;
$R_3$ is hydrogen, fluorine, α-methyl, monofluoromethyl, or difluoromethyl;
$R_2$ is alkyl having 1 to 8 carbon atoms; and
$R_1$ is acyl of the formula

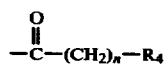

wherein $R_4$ is hydrogen, alkyl having 1 to 10 carbon atoms, or cycloalkyl having 3 to 8 carbon atoms and n is a number from 0 to 4, or
$R_1$ is carbonyloxyalkyl of the formula

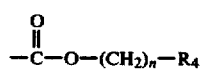

wherein n is 0 or 1 and $R_4$ is as earlier defined except that $R_4$ is other than hydrogen when n is 0, or $R_1$ is

wherein $R_5$ is alkyl having 1 to 4 carbon atoms, phenyl, methylphenyl, ethylphenyl, fluorophenyl, bromophenyl, or chlorophenyl.

2. A compound as in claim 1 wherein $R_1$ is

and $R_4$ is hydrogen.

3. A compound as in claim 1 wherein $R_1$ is

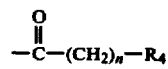

and $R_4$ is alkyl having 1 to 10 carbon atoms.

4. A compound as in claim 1 of the formula

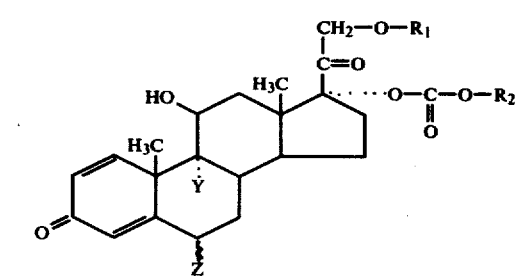

5. A compound as in claim 1 of the formula

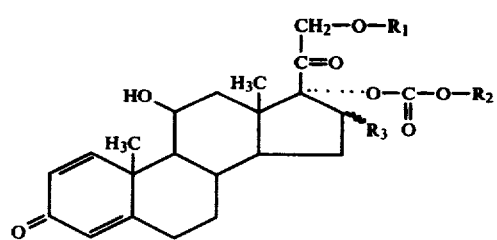

6. A compound as in claim 1 of the formula

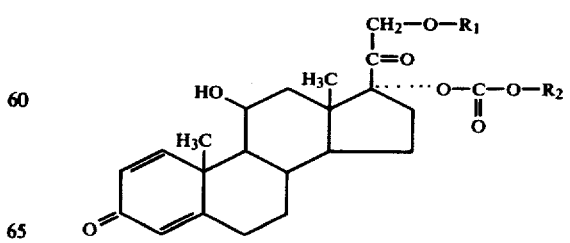

7. A compound as in claim 1 which is prednisolon-17-ethyl-carbonate-21-propionate.

8. A compound as in claim 1 which is prednisolon-17-ethyl-carbonate-21-acetate.

9. A compound as in claim 1 which is prednisolon-17-n-propyl-carbonate-21-propionate.

10. A compound as in claim 1 which is prednisolon-17-n-propyl-carbonate-21-acetate.

11. A compound as in claim 1 which is cortisol-17-ethyl-carbonate-21-propionate.

12. A compound as in claim 2 which is cortisol-17-n-propyl-carbonate-21-propionate.

13. A pharmaceutical composition for the treatment of inflammatory dermatosis which comprises an effective amount of a compound as in claim 1 and a pharmaceutically-acceptable carrier therefor.

14. The method of treating inflammatory dermatosis in a human or animal suffering therefrom which method comprises locally or topically administering an effective amount of a compound as in claim 1.

15. A method for making a compound selected from the group consisting of compounds of the formula

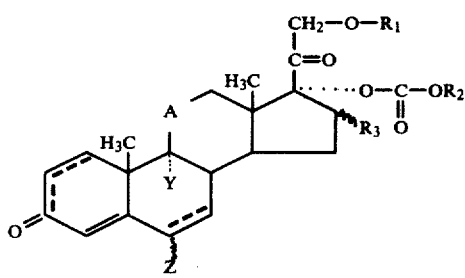

and compounds of the formula

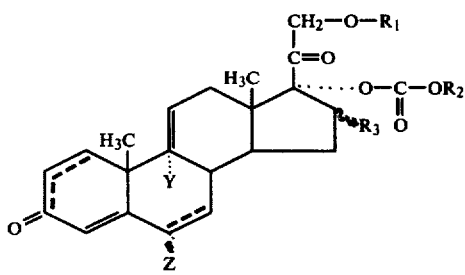

wherein

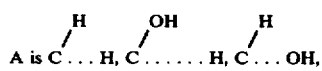

or C=O;
Y is hydrogen, fluorine, or methyl;
Z is hydrogen, chlorine, fluorine, or methyl
$R_3$ is hydrogen, fluorine, α-methyl, monofluoromethyl, or difluoromethyl;
$R_2$ is alkyl having 1 to 8 carbon atoms; and
$R_1$ is acyl of the formula

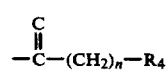

wherein $R_4$ is hydrogen, alkyl having 1 to 10 carbon atoms, or cycloalkyl having 3 to 8 carbon atoms and n is a number from 0 to 4, which method comprises hydrolyzing with weak acid a corticosteroid 17,21-(dialkyl-orthocarbonate) of the formula

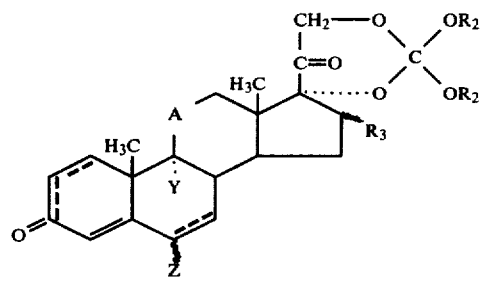

or

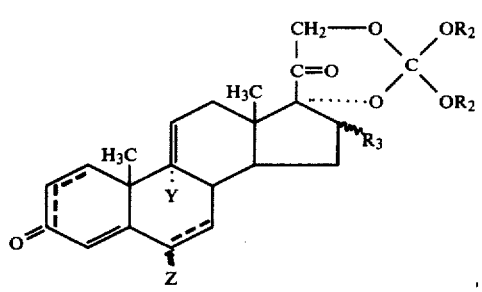

respectively, to form the corresponding 17-(monoalkyl carbonate)-21-hydroxy compound, and then esterifying the 21-hydroxy group by reaction thereof with a halide or anhydride of a carboxylic acid of the formula

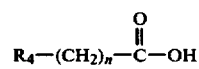

16. A method as in claim 15 wherein A is

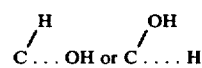

and the hydroxy group thereof is then oxidized to a keto group.

17. A method for making a compound selected from the group consisting of the compounds of the formula

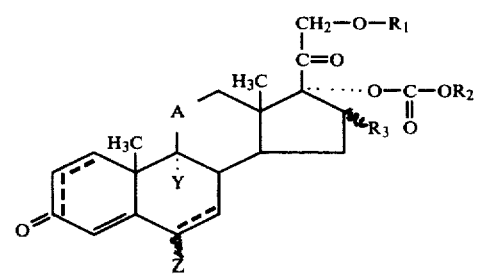

and compounds of the formula

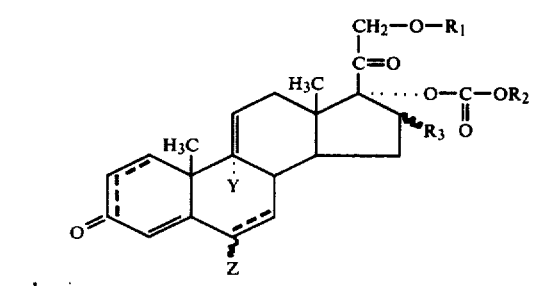

wherein

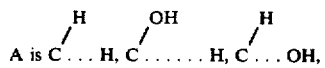

or C=O;
Y is hydrogen, fluorine, or methyl;
Z is hydrogen, chlorine, fluorine, or methyl
$R_3$ is hydrogen, fluorine, α-methyl, monofluoromethyl, or difluoromethyl;
$R_2$ is alkyl having 1 to 8 carbon atoms; and
$R_1$ is carbonyloxyalkyl of the formula

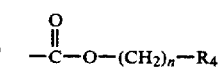

wherein n is 0 or 1 and $R_4$ is hydrogen, alkyl having 1 to 10 carbon atoms, or cycloalkyl having 3 to 8 carbon atoms except that $R_4$ is other than hydrogen if n is 0, which method comprises hydrolyzing with weak acid a corticosteroid 17, 21-(dialkylorthocarbonate) of the formula

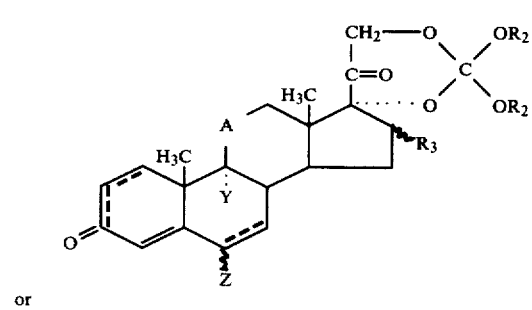

or

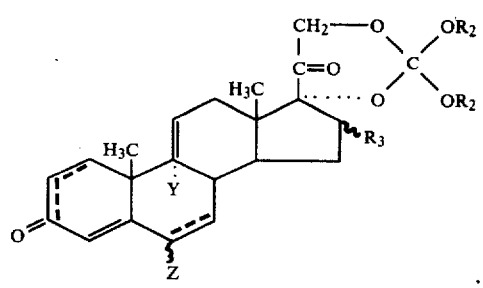

respectively, to form the corresponding 17-(monoalkyl carbonate)-21-hydroxy compound, and then esterifying the 21-hydroxy group by reaction thereof with a halogenoformate of the formula

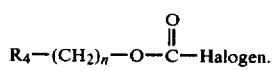

18. A method as in claim 17 wherein A is

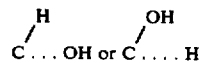

and the hydroxy group thereof is then oxidized to a keto group.

19. A method for making a compound selected from the group consisting of compounds of the formula

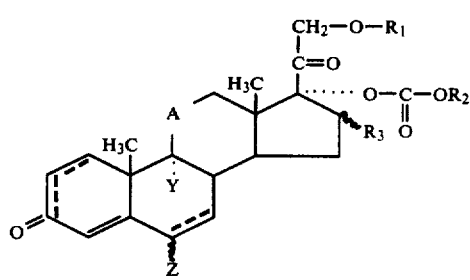

and compounds of the formula

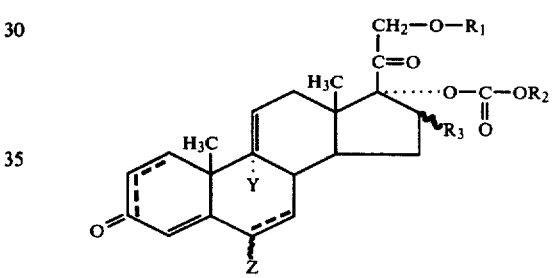

wherein

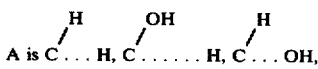

or C=O;
Y is hydrogen, fluorine, or methyl;
Z is hydrogen, chlorine, fluorine, or methyl
$R_3$ is hydrogen, fluorine, α-methyl, monofluoromethyl, or difluoromethyl;
$R_2$ is alkyl having 1 to 8 carbon atoms; and $R_1$ is

wherein $R_5$ is alkyl having 1 to 4 carbon atoms, phenyl, methylphenyl, ethylphenyl, fluorophenyl, bromophenyl, or chlorophenyl, which method comprises hydrolyzing with weak acid a corticosteroid 17,21-(dialkyl-orthocarbonate) of the formula

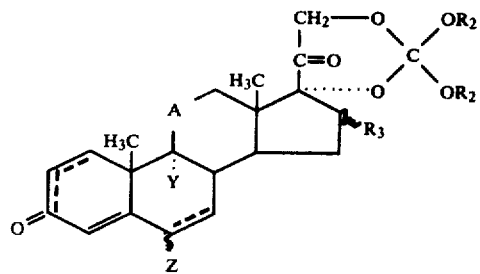

or

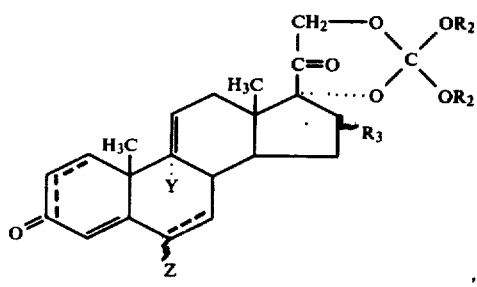

respectively, to form the corresponding 17-(monoalkyl carbonate)-21-hydroxy compound, and then esterifying the 21-hydroxy group by reaction thereof with a sulfonic acid halide of the formula

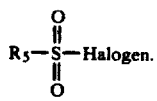

20. A method as in claim 19 wherein A is

and the hydroxy group thereof is then oxidized to a keto group.

21. A compound as in claim 1 wherein $R_1$ is carbonyloxyalkyl of the formula

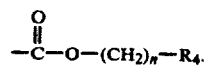

22. A compound as in claim 1 wherein $R_1$ is

* * * * *